United States Patent
Yamasaki et al.

(10) Patent No.: US 9,475,903 B2
(45) Date of Patent: *Oct. 25, 2016

(54) 1,4-BIS(ISOCYANATOMETHYL) CYCLOHEXANE, POLYISOCYANATE COMPOSITION, POLYURETHANE RESIN, MOLDED ARTICLE, EYEWEAR MATERIAL, EYEWEAR FRAME, AND LENS

(71) Applicant: MITSUI CHEMICALS, INC., Tokyo (JP)

(72) Inventors: Satoshi Yamasaki, Chiba (JP); Hirokazu Morita, Chiba (JP); Goro Kuwamura, Chiba (JP); Daisuke Nishiguchi, Sakai (JP); Toshihiko Nakagawa, Ichihara (JP); Daisuke Hasegawa, Yokohama (JP); Tetsuya Hamada, Ichihara (JP); Shinji Kiyono, Kimitsu (JP); Takeshi Fukuda, Kurume (JP); Kazuhiro Kosumi, Omuta (JP); Hidetaka Tsukada, Omuta (JP); Kenichi Goto, Chiba (JP); Shinsuke Ito, Omuta (JP); Naoyuki Kakinuma, Omuta (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/443,774
(22) PCT Filed: Sep. 25, 2014
(86) PCT No.: PCT/JP2014/075511
§ 371 (c)(1),
(2) Date: May 19, 2015
(87) PCT Pub. No.: WO2015/046369
PCT Pub. Date: Apr. 2, 2015
(65) Prior Publication Data
US 2015/0342276 A1 Dec. 3, 2015

(30) Foreign Application Priority Data

Sep. 26, 2013 (JP) .................. 2013-200500
Jun. 19, 2014 (JP) .................. 2014-126296

(51) Int. Cl.
*C08G 18/75* (2006.01)
*C08G 18/78* (2006.01)
(Continued)

(52) U.S. Cl.
CPC .............. *C08G 18/757* (2013.01); *A41B 9/00* (2013.01); *A41B 17/00* (2013.01); *A41D 1/00* (2013.01); *A41D 7/00* (2013.01); *A41D 31/00* (2013.01); *C07C 263/20* (2013.01); *C07C 265/04* (2013.01); *C07C 265/14* (2013.01); *C07D 295/06* (2013.01); *C07D 295/067* (2013.01); *C07D 295/10* (2013.01); *C07D 295/104* (2013.01); *C07D 295/108* (2013.01); *C07D 295/16* (2013.01); *C07D 295/185* (2013.01); *C08G 18/283* (2013.01); *C08G 18/3275* (2013.01); *C08G 18/3855* (2013.01); *C08G 18/4018* (2013.01); *C08G 18/4202* (2013.01); *C08G 18/4277* (2013.01); *C08G 18/44* (2013.01); *C08G 18/4854* (2013.01); *C08G 18/73* (2013.01); *C08G 18/758* (2013.01); *C08G 18/7818* (2013.01); *C08G 18/7831* (2013.01); *C08G 18/7837* (2013.01);
(Continued)

(58) Field of Classification Search
CPC . C07C 265/04; C07C 265/14; C07D 295/06; C07D 295/067; C07D 295/10; C07D 295/104; C07D 295/108; C07D 295/16; C07D 295/185; C08G 18/757; C08G 18/7818; C08G 18/7831; C08G 18/7837; C08G 18/7843; C08G 18/792; C08K 5/3412
See application file for complete search history.

(56) References Cited

U.S. PATENT DOCUMENTS 5,523,467 A 6/1996 Okazaki
8,722,752 B2 * 5/2014 Kuwamura ............. B29C 41/18
521/170

(Continued)

FOREIGN PATENT DOCUMENTS

CN 101821311 A 9/2010
CN 103153940 A 6/2013
(Continued)

OTHER PUBLICATIONS

International Search Report dated Dec. 9, 2014 filed in PCT/JP2014/075511.
National Standard of People's Republic of China; Determination of Hydrolyzable Chlorine Content in Isocyanates, GB12009.2-89 (Issued on Dec. 25, 1989 and effective on Nov. 1, 1990) and its English translation of the relevant parts.; Cited in Notice of Allowance issued on Aug. 25, 2016 in connection with Chinese Patent Application No. 201510367329.6.
(Continued)

*Primary Examiner* — Rabon Sergent
(74) *Attorney, Agent, or Firm* — Rankin, Hill & Clark LLP

(57) ABSTRACT

1,4-bis(isocyanatomethyl)cyclohexane contains 70 mol % or more and 95 mol % or less of a trans isomer relative to a total amount of a cis isomer and the trans isomer, and 0.1 ppm or more and 300 ppm or less of the compound represented by formula (1) below:

[Chemical Formula 1]

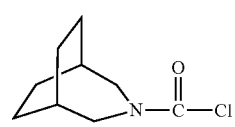

(1)

20 Claims, 8 Drawing Sheets

(51) Int. Cl.

| | | |
|---|---|---|
| C08K 5/3412 | (2006.01) |
| A41D 31/00 | (2006.01) |
| G02B 1/04 | (2006.01) |
| C08J 5/18 | (2006.01) |
| D04H 1/4358 | (2012.01) |
| D04H 3/009 | (2012.01) |
| D04B 9/00 | (2006.01) |
| A41D 7/00 | (2006.01) |
| A41B 9/00 | (2006.01) |
| A41D 1/00 | (2006.01) |
| A41B 17/00 | (2006.01) |
| G02C 5/00 | (2006.01) |
| C08G 18/79 | (2006.01) |
| C07C 265/04 | (2006.01) |
| C07C 265/14 | (2006.01) |
| C07D 295/06 | (2006.01) |
| C07D 295/067 | (2006.01) |
| C07D 295/10 | (2006.01) |
| C07D 295/104 | (2006.01) |
| C07D 295/108 | (2006.01) |
| C07D 295/16 | (2006.01) |
| C07D 295/185 | (2006.01) |
| C08G 18/48 | (2006.01) |
| C08G 18/73 | (2006.01) |
| C08G 18/28 | (2006.01) |
| C08G 18/32 | (2006.01) |
| C08G 18/38 | (2006.01) |
| C08G 18/40 | (2006.01) |
| C08G 18/42 | (2006.01) |
| C08G 18/44 | (2006.01) |
| C07C 263/20 | (2006.01) |
| C08G 101/00 | (2006.01) |
| D01F 6/70 | (2006.01) |

(52) U.S. Cl.
CPC ....... *C08G 18/7843* (2013.01); *C08G 18/792* (2013.01); *C08J 5/18* (2013.01); *C08K 5/3412* (2013.01); *D04B 9/00* (2013.01); *D04H 1/4358* (2013.01); *D04H 3/009* (2013.01); *G02B 1/04* (2013.01); *G02B 1/041* (2013.01); *G02C 5/00* (2013.01); *A41B 2500/50* (2013.01); *C08G 2101/00* (2013.01); *C08G 2170/20* (2013.01); *C08G 2190/00* (2013.01); *C08J 2375/04* (2013.01); *D01F 6/70* (2013.01); *Y10T 428/249921* (2015.04); *Y10T 442/60* (2015.04)

(56) References Cited

U.S. PATENT DOCUMENTS

| | | | |
|---|---|---|---|
| 2004/0087754 A1* | 5/2004 | Foley | C08G 18/664 528/59 |
| 2006/0058453 A1* | 3/2006 | Argyropoulos | C08G 18/4277 524/589 |
| 2010/0129646 A1 | 5/2010 | Vreys | |
| 2010/0184938 A1 | 7/2010 | Warakomski | |
| 2010/0216905 A1 | 8/2010 | Kuwamura et al. | |
| 2010/0227985 A1 | 9/2010 | Nishiguchi | |
| 2013/0197269 A1 | 8/2013 | Kiyono | |
| 2013/0197270 A1 | 8/2013 | Sawada | |
| 2013/0338330 A1 | 12/2013 | Yamasaki | |
| 2014/0303150 A1 | 10/2014 | Högberg | |

FOREIGN PATENT DOCUMENTS

| | | |
|---|---|---|
| GB | 1042910 A | 9/1966 |
| JP | 354218 | 3/1991 |
| JP | 2001187765 A2 | 7/2001 |
| JP | 2009149848 A2 | 7/2009 |
| JP | 201376076 | 4/2013 |
| JP | 2013213222 A2 | 10/2013 |
| WO | 2009051114 A1 | 4/2009 |
| WO | 2012083953 A1 | 6/2012 |
| WO | 2012121291 A1 | 9/2012 |
| WO | WO 2013/089137 A1 * | 6/2013 |

OTHER PUBLICATIONS

Polyurethane Industry, No. 2, 1992; Issues to be Concerned in Determination of Hydrolyzable Chlorine in Isocyanates Yuru DAI (Jiangsu Chemical Industry Institute, Nanjing, 210024) and its English translation of the relevant parts.; Cited in Notice of Allowance issued on Aug. 25, 2016 in connection with Chinese Patent Application No. 201510367329.6.
Illustration for Application of Determination of Hydrolyzable Chlorine Content in Isocyanates Ziqing Zhou (Jiangsu Chemical Industry Institute), Nov. 1, 1990 and its English translation of the relevant parts.; Cited in Notice of Allowance issued on Aug. 25, 2016 in connection with Chinese Patent Application No. 201510367329.6.
PCT International Preliminary Report on Patentability (Form PCT/IB/373) and (Form PCT/ISA/237) issued on Dec. 9, 2014 with PCT Notification Concerning Transmittal of International Preliminary Report on Patentability (form PCT/IB/326), 5 pages.
PCT International Preliminary Report on Patentability (Form PCT/IB/373) and (Form PCT/ISA/237) issued on Dec. 9, 2014 with PCT Notification of Transmittal of Translation of the International Preliminary Report on Patentability (form PCT/IB/338), 6 pages.

* cited by examiner

1,4-BIS(ISOCYANATOMETHYL) CYCLOHEXANE, POLYISOCYANATE COMPOSITION, POLYURETHANE RESIN, MOLDED ARTICLE, EYEWEAR MATERIAL, EYEWEAR FRAME, AND LENS

TECHNICAL FIELD

The present invention relates to 1,4-bis(isocyanatomethyl)cyclohexane, a polyisocyanate composition, a polyurethane resin, a molded article, an eyewear material, an eyewear frame, and a lens.

BACKGROUND ART

Heretofore, 1,4-bis(aminomethyl)cyclohexane has been well known for a raw material of polyamide used for fiber, film, etc.

Furthermore, 1,4-bis(isocyanatomethyl)cyclohexane derived from 1,4-bis(aminomethyl)cyclohexane is useful as, for example, a polyurethane material used for paints, adhesives, and eyewear frames and lenses for eyewear (corrective glasses, protection glasses, sunglasses, goggles, etc.), and for example, a polyisocyanate composition material used for a curing agent for paints.

1,4-bis(aminomethyl)cyclohexane has two stereo isomers of trans-1,4-bis(aminomethyl)cyclohexane (hereinafter may be referred to as trans isomer) and cis-1,4-bis(aminomethyl) cyclohexane (hereinafter may be referred to as cis isomer), and it has been known that the ratio between the cis isomer and the trans isomer in 1,4-bis(aminomethyl)cyclohexane affect various physical properties of polyamides and polyurethanes produced by using 1,4-bis(aminomethyl)cyclohexane.

To be specific, for example, a proposal has been made to produce a polyurethane resin having various excellent physical properties by reaction of a polyisocyanate component containing 1,4-bis(isocyanatomethyl)cyclohexane including 80 mol % or more of trans 1,4-bis(isocyanatomethyl)cyclohexane with an active hydrogen compound component (e.g., see Patent Document 1).

CITATION LIST

Patent Document

Patent document 1 International Patent Publication WO2009/051114

SUMMARY OF THE INVENTION

Problem to be Solved by the Invention

Meanwhile, in production of a polyurethane resin, it is desired that material components are selected to further improve required physical properties in accordance with various uses.

An object of the present invention is to provide 1,4-bis (isocyanatomethyl)cyclohexane that can improve required physical properties in various uses, a polyisocyanate composition and a polyurethane resin produced by using the 1,4-bis(isocyanatomethyl)cyclohexane, and furthermore, a molded article, an eyewear material, an eyewear frame, and a lens produced from the polyurethane resin.

Means for Solving the Problem

To achieve the above object, 1,4-bis(isocyanatomethyl) cyclohexane of the present invention contains 70 mol % or more and 95 mol % or less of a trans isomer relative to a total amount of a cis isomer and the trans isomer, and contains 0.1 ppm or more and 300 ppm or less of a compound represented by formula (1) below:

[Chemical Formula 1]

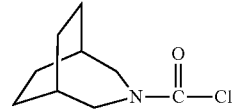

(1)

It is preferable that the 1,4-bis(isocyanatomethyl)cyclohexane of the present invention contains 80 mol % or more and 93 mol % or less of the trans isomer relative to a total amount of the cis isomer and the trans isomer.

A polyisocyanate composition of the present invention is produced by modifying the above-described 1,4-bis(isocyanatomethyl)cyclohexane, and contains at least one functional group of (a) to (e) below:

(a) an isocyanurate group,
(b) an allophanate group,
(c) a biuret group,
(d) a urethane group, and
(e) a urea group.

A polyurethane resin of the present invention is produced by allowing a polyisocyanate component containing the above-described 1,4-bis(isocyanatomethyl)cyclohexane to react with an active hydrogen group-containing component.

A polyurethane resin of the present invention is produced by allowing a polyisocyanate component containing the above-described polyisocyanate composition to react with an active hydrogen group-containing component.

A molded article of the present invention is produced from the above-described polyurethane resin.

An eyewear material of the present invention includes a polyurethane resin produced by allowing a polyisocyanate component containing 1,4-bis(isocyanatomethyl)cyclohexane to react with an active hydrogen group-containing component, wherein the 1,4-bis(isocyanatomethyl)cyclohexane contains 70 mol % or more and 95 mol % or less of a trans isomer relative to a total amount of a cis isomer and the trans isomer, and contains 0.1 ppm or more and 300 ppm or less of a compound represented by formula (1) below:

[Chemical Formula 2]

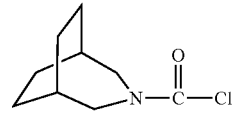

(1)

In the eyewear material of the present invention, it is preferable that the 1,4-bis(isocyanatomethyl)cyclohexane contains 80 mol % or more and 93 mol % or less of the trans isomer relative to a total amount of the cis isomer and the trans isomer.

An eyewear frame of the present invention is produced from the above-described eyewear material, A lens of the present invention is produced from the above-described eyewear material.

Effects of the Invention 1,4-bis(isocyanatomethyl)cyclohexane of the present invention contains the trans isomer and the above-described compound represented by formula (1) above in the above-described specific range, and therefore a polyurethane resin having various excellent physical properties can be produced.

The polyisocyanate composition of the present invention is produced by using the 1,4-bis(isocyanatomethyl)cyclohexane of the present invention, and therefore by using the polyisocyanate composition, a polyurethane resin having various excellent physical properties can be produced.

The polyurethane resin, molded article, eyewear material, eyewear frame, and lens of the present invention are produced by using the 1,4-bis(isocyanatomethyl)cyclohexane of the present invention or the polyisocyanate composition of the present invention, and therefore are excellent in various physical properties.

Figure 1:
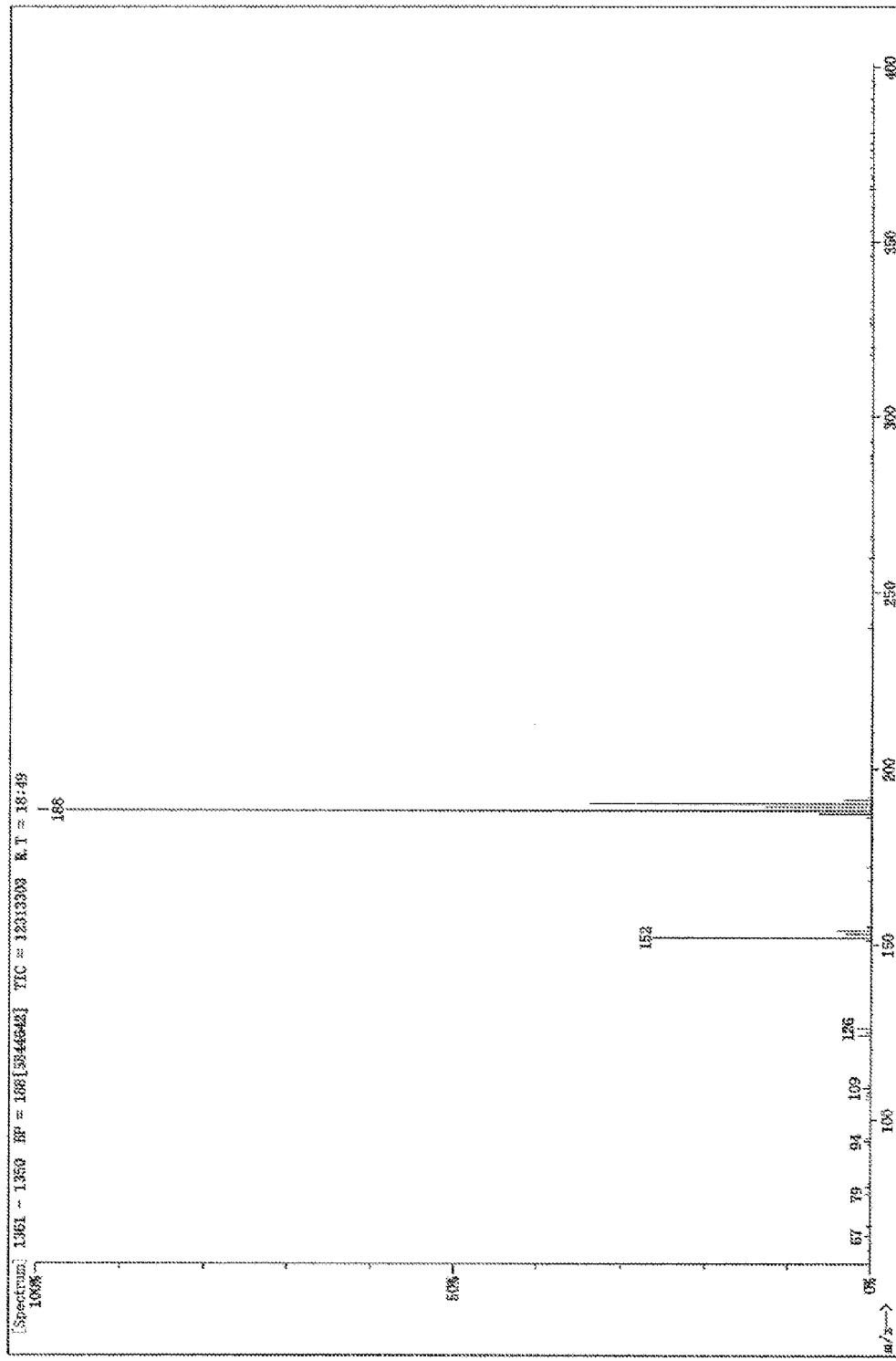
FIG. 1 shows a CI mass spectrum of GC-MS analysis on the compound represented by formula (1).

DESCRIPTION OF EMBODIMENTS 1,4-bis(isocyanatomethyl)cyclohexane of the present invention contains trans-1,4-bis(isocyanatomethyl)cyclohexane (hereinafter trans isomer) and cis-1,4-bis(isocyanatomethyl)cyclohexane (hereinafter cis isomer).

The 1,4-bis(isocyanatomethyl)cyclohexane contains 70 mol % or more, preferably 75 mol % or more, more preferably 80 mol % or more, and 95 mol % or less, preferably 93 mol % or less, more preferably 90 mol % or less of the trans isomer.

The trans isomer content can be determined by analysis with a gas chromatograph in conformity with Examples to be described later (the same applies in the following).

The 1,4-bis(isocyanatomethyl)cyclohexane of the present invention contains a compound represented by formula (1) below.

[Chemical Formula 3]

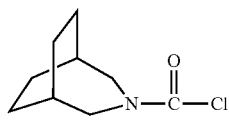

(1)

The 1,4-bis(isocyanatomethyl)cyclohexane contains 0.1 ppm or more, preferably 0.4 ppm or more, more preferably 1 ppm or more and 300 ppm or less, preferably 200 ppm or less, more preferably 100 ppm or less of the above-described compound represented by formula (1) above relative to a total amount thereof.

The amount of the compound represented by formula (1) contained can be determined by analysis with a gas chromatograph in conformity with Examples to be described later (the same applies in the following), When the amounts of the trans isomer and compound represented by formula (1) above in 1,4-bis(isocyanatomethyl)cyclohexane are in the above-described specific ranges, a polyurethane resin having various excellent physical properties can be produced.

Such 1,4-bis(isocyanatomethyl)cyclohexane can be produced, for example, by isocyanization of 1,4-bis(aminomethyl)cyclohexane.

1,4-bis(aminomethyl)cyclohexane used for production of the above-described 1,4-bis(isocyanatomethyl)cyclohexane contains, for example, trans-1,4-bis(aminomethyl)cyclohexane (hereinafter trans isomer) and cis-1,4-bis(aminomethyl)cyclohexane (hereinafter cis isomer).

The 1,4-bis(aminomethyl)cyclohexane has a trans isomer content of, for example, 70 mol % or more, preferably 75 mol % or more, more preferably 80 mol % or more, and for example, 95 mol % or less, preferably 93 mol % or less, more preferably 90 mol % or less.

The trans isomer content can be determined by analysis with a gas chromatograph in conformity with Examples to be described later (the same applies in the following).

The 1,4-bis(aminomethyl)cyclohexane contains a compound represented by formula (2) (3-azabicyclo[3,2,2]nonane) below.

[Chemical Formula 4]

(2)

The 1,4-bis(aminomethyl)cyclohexane contains the above-described compound represented by formula (2) relative to a total amount thereof of, for example, 0.005 mass % or more, preferably 0.01 mass % or more, more preferably 0.1 mass % or more, and for example, 3 mass % or less, preferably 1.5 mass % or less.

The amount of the above-described compound represented by formula (2) contained can be determined by analysis with a gas chromatograph in conformity with Examples to be described later (the same applies in the following).

When the 1,4-bis(aminomethyl)cyclohexane contains the trans isomer and the above-described compound represented by formula (2) in the above-described specific ranges, 1,4-bis(isocyanatomethyl)cyclohexane of the present invention can be produced efficiently.

In the following, a method of producing the above-described 1,4-bis(aminomethyl)cyclohexane is described.

In this method, for example, first, terephthalic acid or a derivative thereof of at least one selected from the group consisting of terephthalic acid, terephthalic acid ester, and terephthalic acid amide is subjected to nuclear hydrogenation to produce hydrogenated terephthalic acid or a derivative thereof (nuclear hydrogenation step).

To be specific, in the nuclear hydrogenation step, terephthalic acid or a derivative thereof of at least one selected from the group consisting of terephthalic acid, terephthalic acid ester, and terephthalic acid amide is subjected to nuclear hydrogenation to produce a corresponding hydrogenated terephthalic acid (that is, at least one hydrogenated terephthalic acid or a derivative thereof selected from the group consisting of cyclohexane-1,4-dicarboxylic acid, cyclohexane-1,4-dicarboxylic acid ester, and cyclohexane-1,4-dicarboxylic acid amide).

In the nuclear hydrogenation step, for example, the method described in Japanese Unexamined Patent Publication No. 2001-181223 can be used.

The terephthalic acid or terephthalic acid derivative used as a raw material in the present invention may be one having quality of industrially available products, and also undried (containing water) terephthalic acid or terephthalic acid derivative that has undergone the purification in the hydrogenation step generally performed in production of terephthalic acid may be used.

The reaction in the nuclear hydrogenation step is exothermic reaction, and therefore to suitably suppress the temperature increase due to the heat of reaction, and also to increase conversion, it is preferable that a solvent that is inactive in such a reaction is added as a diluent to the raw material terephthalic acid or terephthalic acid derivative so that the terephthalic acid or terephthalic acid derivative concentration in the reaction solution is, for example, 1 to 50 mass %, preferably 2 to 30 mass %. When the concentration in the reaction solution is within the range, it is advantageous in that the reaction rate is not reduced, and the temperature increase in the reactor is small.

Examples of such a solvent include aqueous solvents such as water, methanol, isopropanol, and 1,4-dioxane.

Use of such an aqueous solvent is advantageous in that the reaction mixture in the nuclear hydrogenation step can be cooled as necessary, and re-circulated for use.

In this case, water is used preferably because it can be recovered by separation operation thereafter; it does not allow unwanted components to be mixed into the reaction system; and undried terephthalic acid that underwent the purification step of terephthalic acid can be used.

In the nuclear hydrogenation step, hydrogen used in the nuclear hydrogenation may be of industrial use quality. For example, the hydrogen may contain inactive gas (e.g., nitrogen, methane, etc.) but its hydrogen concentration is preferably 50% or more.

The hydrogen amount is preferably about 3 to 50 times the raw material terephthalic acid or terephthalic acid derivative in molar ratio.

When the hydrogen amount is within such a range, the amount of unreacted materials is small, the reaction rate is sufficient, and it is advantageous economically.

In the nuclear hydrogenation step, a known catalyst may be added.

The catalyst used in the nuclear hydrogenation step is a general noble metal catalyst for nuclear hydrogenation. To be specific, examples of such a catalyst include palladium, platinum, ruthenium, and rhodium, and preferably, palladium or ruthenium is used.

These catalysts are preferably prepared as a supported catalyst. Examples of carriers for such catalysts include activated carbon, alumina, silica, and kieselguhr, and preferably, activated carbon or silica is used.

The amount of metal (e.g., palladium, platinum, ruthenium, rhodium, etc.) supported is in the range of, for example, 0.1 to 10 mass %, preferably 0.5 to 10 mass %, of the total amount including the catalyst carrier.

When the amount of metal supported is within such a range, it is preferable because the activity of catalyst per weight is high.

The catalyst is used in the form of, for example, powder, granular, or may be supported on a pellet carrier. Preferably, the catalyst is in the form of powder. When the catalyst has an appropriate size, for example, when the catalyst is powder catalyst, the catalyst contains an internal portion that effectively contributes to reaction in a large amount, and therefore the reaction rate does not easily decrease.

The catalyst amount relative to 100 parts by mass of terephthalic acid or terephthalic acid derivative is in the range of, for example, 0.1 to 50 parts by mass, preferably 0.5 to 20 parts by mass.

The terephthalic acid or terephthalic acid derivative is not highly soluble in general solvents such as water, and therefore is prepared as a dispersion liquid. The reaction is preferably liquid-phase slurry reaction.

The reactor is preferably a pressure-resistant vessel.

A dispersion liquid of terephthalic acid or a derivative thereof, and hydrogen are introduced from the reactor top or bottom, and brought into contact with the catalyst in a suspension. After the reaction, the product, i.e., hydrogenated terephthalic acid or terephthalic acid derivative, is highly soluble in a general solvent such as water at high temperature, and therefore separation from the catalyst can be performed by filtration.

In the filtration, the above-described product is dissolved in, for example, a known alkaline solution (e.g., aqueous sodium hydroxide solution, etc.), and after the solution is filtered, the solution can be neutralized by a known acid solution (e.g., aqueous hydrogen chloride solution, etc.).

Thereafter, by drying or concentrating the product, or by crystallizing the product by cooling, hydrogenated terephthalic acid or terephthalic acid derivative can be produced.

The reaction temperature is usually in the range of 50 to 200° C., and preferably 100 to 160° C.

The reaction temperature within such a range is advantageous in that the amount of unreacted materials and by-products is less, hydrogenolysis does not occur easily, and as a result, the yield increases.

The reaction pressure is usually in the range of 0.5 to 15 MPa (gauge pressure), preferably 2 to 15 MPa (gauge pressure), more preferably 2 to 8 MPa (gauge pressure), even more preferably 2 to 5 MPa (gauge pressure).

The reaction pressure within such a range is advantageous in that the reaction rate does not easily decrease, and the amount of by-products is less.

The conversion of terephthalic acid or terephthalic acid derivative is usually 90% or more, preferably 95% or more, and more preferably 98% or more.

When the amount of the unreacted terephthalic acid or terephthalic acid derivative is small as described above, it is advantageous in that post-treatments become not so complicated.

The hydrogenated terephthalic acid or terephthalic acid derivative obtained in the nuclear hydrogenation step is a mixture of a cis isomer (that is, cis-1,4-cyclohexane dicarboxylic acid, cis-1,4-cyclohexane dicarboxylic acid ester, and/or cis-1,4-cyclohexane dicarboxylic acid amide) and a trans isomer (that is, trans-1,4-cyclohexane dicarboxylic acid, trans-1,4-cyclohexane dicarboxylic acid ester, and/or trans-1,4-cyclohexane dicarboxylic acid amide).

Next, in this method, the above-described hydrogenated terephthalic acid or derivative thereof produced in the nuclear hydrogenation step is treated with ammonia to produce 1,4-dicyanocyclohexane (cyanation step).

In the cyanation step, for example, the method described in Japanese Unexamined Patent Publication No. S63-10752 may be used.

To be more specific, in the cyanation step, the hydrogenated terephthalic acid or terephthalic acid derivative obtained in the nuclear hydrogenation step is allowed to react with a compound capable of serving as an ammonia source (e.g., ammonia, urea, ammonium carbonate, etc.) (hereinafter may be referred to as an ammonia source) by heating at, usually 200° C. or more and below 350° C., preferably 230° C. or more and below 320° C.

The reaction temperature within such a range is advantageous in that the reaction rate does not decrease, and decomposition due to excessive heating occurs less.

In this method, metal oxide can be used as a catalyst in the cyanation step.

Examples of the metal oxide include silica, alumina, phosphorus pentoxide, tin oxide, titanium oxide, zinc oxide, iron oxide, zirconium oxide, and cobalt oxide.

Of these metal oxides, in view of easy separation after reaction, silica, alumina, tin oxide, titanium oxide, zinc oxide, iron oxide, zirconium oxide, or cobalt oxide is preferably used.

In this step, furthermore, metal oxide and other catalysts can be used in combination, and examples of such a catalyst include mineral acids such as hydrochloric acid, phosphoric acid, and sulfuric acid, and organic acids such as acetic acid, propionic acid, and benzoic acid.

When metal oxide and other catalyst are used in combination, the mixing ratio of these is not particularly limited, and is set suitably in accordance with the purpose and application.

The catalyst is used in the form of, for example, powder, granular, or may be supported on a pellet carrier. Preferably, the catalyst is in the form of powder.

When the catalyst has an appropriate size, for example, when the catalyst is powder catalyst, the catalyst contains an internal portion that effectively contributes to reaction in a large amount, and therefore the reaction rate does not easily decrease.

The amount of catalyst relative to 100 parts by mass of hydrogenated terephthalic acid or terephthalic acid derivative is in the range of, for example, 0.1 to 50 parts by mass, preferably 0.5 to 20 parts by mass.

In the reaction, a solvent is preferably used as appropriate.

Examples of the solvent include, although any solvent that does not inhibit the purpose of the method of the present invention can be used, aliphatic or alicyclic hydrocarbons such as decane, undecane, dodecane, tridecane, tetradecane, pentadecane, and decalin; aromatic hydrocarbons such as mesitylene, tetralin, butylbenzene, p-cymene, diethylbenzene, diisopropylbenzene, triethylbenzene, cyclohexylbenzene, dipentylbenzene, and dodecylbenzene; alcohols such as hexanol, 2-ethylhexanol, octanol, decanol, dodecanol, ethylene glycol, diethylene glycol, and triethylene glycol; ethers such as diethyleneglycol dimethylether, triethyleneglycol dimethylether, tetraethyleneglycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; polar aprotic solvents such as dimethyl sulfoxide, N,N-dimethylformamnide, N,N-dimethylacetamide, hexamethylphosphoramide, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea; and the product in this step, i.e., 1,4-dicyanocyclohexane. These solvents may be used singly or in combination of two or more, As the solvent, in view of suppressing crystallization of 1,4-dicyanocyclohexane to the gas purge line of the reactor, and to apparatuses at downstream of the reactor such as a condenser, the solvent is preferably selected from, for example, ethers such as diethyleneglycol dimethylether, triethyleneglycol dimethylether, tetraethyleneglycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; and polar aprotic solvents such as dimethyl sulfoxide, N,N-dimethylformamide, N,N-dimethylacetamide, hexamethylphosphoramide, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

Of the above-described solvents, those solvents having a boiling point of 180° C. to 350° C. is preferably used. Use of the solvent having a boiling point lower than 180° C. is not preferable because the energy load on the reactor increases. Use of the solvent having a boiling point higher than 350° C. is not preferable because the effects of suppressing the crystallization of 1,4-dicyanocyclohexane to the reactor gas purge line and to apparatuses at downstream of the reactor such as a condenser decreases.

In view of the above, of the above-described solvents, selection is made preferably from o-dichlorobenzene, triethyleneglycol dimethylether, tetraethyleneglycol dimethylether, N,N'-dimethylimidazolidinone, N,N'-diethylimidazolidinone, N,N'-dipropylimidazolidinone, N,N',4-trimethylimidazolidinone, and N,N'-dimethylpropyleneurea.

The amount of solvent used is not particularly limited, and usually is 10 times or less by mass the reactant (including the above-described hydrogenated terephthalic acid or terephthalic acid derivative obtained in the nuclear hydrogenation step), preferably 1 time or less by mass the reactant, and more preferably 3 to 50 parts by mass relative to 100 parts by mass of the hydrogenated terephthalic acid or terephthalic acid derivative. When the amount of the solvent is small, or when no solvent is used, suppression of crystallization of 1,4-dicyanocyclohexane to the gas purge line of the reactor and to apparatuses at downstream of the reactor such as a condenser becomes difficult, and when the amount of the solvent is large, it is not preferable because energy load on the reactor increases.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, a hydrogenated terephthalic acid or terephthalic acid derivative, and a catalyst are introduced from the reactor top or bottom, and the hydrogenated terephthalic acid or terephthalic acid derivative is dissolved by heating to be suspended; and an ammonia supply source compound such as ammonia is fed intermittently or continuously to the reactor, to allow reaction at a predetermined temperature.

The amount of the ammonia supply source compound to be fed is, in view of making easy the treatment and recovery of ammonia after reaction, for example, 1 to 20 mol, preferably 2 to 20 mol relative to 1 mol of hydrogenated terephthalic acid or terephthalic acid derivative.

The rate of the feeding of the ammonia source is not particularly limited, and preferably 0.1 mol to 2 mol relative to 1 mol of hydrogenated terephthalic acid or terephthalic acid derivative per 1 hour, and more preferably, more than 0.5 mol and 2 mol or less (that is, more than 0.5 mol equivalent/hydrogenated terephthalic acid or terephthalic acid derivative/hr and 2 mol equivalent/hydrogenated terephthalic acid or terephthalic acid derivative/hr or less).

The feeding rate lower than 0.5 mol relative to 1 mol of hydrogenated terephthalic acid or terephthalic acid derivative per 1 hour is not preferable because the reaction requires a long time. The feeding rate higher than 2 mol relative to 1 mol of hydrogenated terephthalic acid or terephthalic acid derivative per 1 hour is disadvantageous economically in that the unreacted ammonia source increase in volume, and therefore, for example, when ammonia is to be recovered and reused, the burden is substantial.

The feeding time is suitably selected depending on the feeding rate. For example, the feeding time is 1 to 80 hours, preferably 2 to 50 hours.

Water is produced as a by-product in this reaction, and therefore in view of accelerating the reaction, water is preferably removed out of the system. To remove water out of the system, for example, an inactive gas such as nitrogen can be fed to the reactor.

The reaction may be performed under any pressure condition, for example, under elevated pressure, ambient pressure, and reduced pressure, which is suitably selected.

After the reaction, the product, i.e., 1,4-dicyanocyclohexane, is produced as a mixture (stereo isomers) of cis-1,4-dicyanocyclohexane (cis isomer) and trans-1,4-dicyanocyclohexane (trans isomer).

The cis isomer/trans isomer ratio of the 1,4-dicyanocyclohexane obtained converges to the equilibrium composition ratio of 1,4-dicyanocyclohexane at the reaction temperature, approximately, to cis isomer/trans isomer=40/60 to 60/40, regardless of the stereo isomer ratio of the hydrogenated terephthalic acid or terephthalic acid derivative.

The unreacted ammonia source compound is, as necessary, recovered and reused.

In the above-described cyanation step, 1,4-dicyanocyclohexane is produced as a mixture containing, for example, a catalyst such as metal oxide, and furthermore, a reaction intermediate in the cyanation reaction, and a high boiling point component such as by-products.

Thus, in this method, as necessary, catalysts and high boiling point components are separated and recovered.

To be specific, first, from the mixture (mixture containing 1,4-dicyanocyclohexane, catalyst, and high boiling point component) produced in the above-described cyanation step, the catalyst is separated by, for example, a known separation method such as distillation, filtration, and extraction. The separated catalyst is recovered, and as necessary, reused.

Meanwhile, the high boiling point component is separated from the mixture (mixture containing 1,4-dicyanocyclohexane and high boiling point component) from which the catalyst is removed by, for example, distillation.

The distillation conditions when the high boiling point component is separated by distillation are, to be specific, as follows: a column top pressure of the distillation column of, for example, 2 kPa or more, preferably 3 kPa or more, and for example, 10 kPa or less, preferably 5 kPa or less.

Furthermore, the column top temperature of the distillation column is, for example, 130° C. or more, preferably 140° C. or more, and for example, 200° C. or less, preferably 190° C. or less. The column bottom temperature is, for example, 160° C. or more, preferably 180° C. or more, and for example, 280° C. or less, preferably 260° C. or less.

The column bottom residence time is, for example, 0.01 hours or more, preferably 0.1 hours or more, and for example, 50 hours or less, preferably 25 hours or less.

With the above conditions, the high boiling point component is separated as a column bottom component from the above-described mixture, and recovered.

Furthermore, as necessary, the mixture (mixture of stereo isomers of 1,4-dicyanocyclohexane) from which the high boiling point component is separated (removed) is, for example, subjected to distillation and purification so that the trans-1,4-dicyanocyclohexane (trans isomer) content can be increased.

The distillation conditions when the trans isomer is purified by distillation are as follows: the column top pressure of the distillation column is, for example, 3 kPa or more, preferably 4 kPa or more, and for example, 30 kPa or less, preferably 15 kPa or less.

The column top temperature of the distillation column is, for example, 130° C. or more, preferably 140° C. or more, and for example, 200° C. or less, preferably 190° C. or less. Furthermore, the column bottom temperature is, for example, 160° C. or more, preferably 180° C. or more, and for example, 280° C. or less, preferably 260° C. or less.

The column bottom residence time is, for example, 0.1 hours or more, preferably 0.2 hours or more, and for example, 50 hours or less, preferably 25 hours or less.

When the distillation conditions are within the above-described range, trans-1,4-dicyanocyclohexane in the mixture of stereo isomers can be purified.

Purity of the produced trans-1,4-dicyanocyclohexane (trans isomer ratio) can be suitably controlled based on the separation conditions.

In such distillation, the organic solvent used in the cyanation step can be recovered as a column top component. The recovered organic solvent can be reused as necessary.

Next, in this method, 1,4-dicyanocyclohexane produced in the above-described cyanation step is treated with hydrogen to produce 1,4-bis(aminomethyl)cyclohexane (aminomethylation step).

In the aminomethylation step, for example, the method described in, for example, Japanese Unexamined Patent Publication No. 2001-187765 can be used.

In the aminomethylation step, the hydrogen used in the aminomethylation may be of industrial use quality, and the hydrogen may contain inactive gas (e.g., nitrogen, methane, etc.). The hydrogen concentration is preferably 50% or more.

As the hydrogenation catalyst used in the aminomethylation step, a known hydrogenation catalyst, for example, any of a cobalt catalyst, a nickel catalyst, a copper catalyst, and a noble metal catalyst can be used.

In view of reactivity and selectivity, a catalyst mainly composed of nickel, cobalt and/or ruthenium is preferably used, and more preferably, Raney catalyst or a catalyst supported on porous metal oxides such as silica, alumina, silica alumina, kieselguhr, and activated carbon is preferably used.

The catalyst may further contain metals such as aluminum, zinc, and silicon.

These hydrogenation catalysts may contain, as a reaction accelerator, a metal selected from chromium, iron, cobalt, manganese, tungsten, and molybdenum.

The hydrogenation catalyst can be used as a perfect solid catalyst, or can be used as a supported solid catalyst, for example, nickel, cobalt, or ruthenium supported on aluminum oxide, titanium oxide, zirconium oxide, magnesia/alumina, etc.

The catalyst is used in the form of, for example, powder, granular, or may be supported on a pellet carrier. Preferably, the catalyst is in the form of powder. When the catalyst has an appropriate size, for example, when the catalyst is powder catalyst, the catalyst contains an internal portion that effectively contributes to reaction in a large amount, and therefore the reaction rate does not easily decrease.

The amount of catalyst used is, in view of reactivity and selectivity, for example, 0.1 to 20 parts by mass, preferably 0.5 to 15 parts by mass relative to 100 parts by mass of 1,4-dicyanocyclohexane.

For the reaction, a solvent can be used suitably, and examples of such a solvent include aqueous solvents such as water; alcohols such as methanol, ethanol, 1-propanol, isopropanol, 1-butanol, 2-butanol, and t-butanol; and 1,4-dioxane.

The reaction solution has a 1,4-dicyanocyclohexane concentration of, for example, 1 to 50 mass %, preferably 2 to 40 mass %.

When the reaction solution has a 1,4-dicyanocyclohexane concentration in the above range, it is advantageous in that the reaction rate does not decrease, and the temperature increase in the reactor is small.

The reaction is preferably performed in the presence of ammonia.

Ammonia works to suppress production of by-products such as secondary amines, tertiary amines, and polyamines other than the target 1,4-bis(aminomethyl)cyclohexane, that is, functions to improve reaction selectivity.

The amount of ammonia used is, in view of suppressing the above-described production of by-products, preventing decrease in hydrogenation rate, and making easy the treatment and recovery of ammonia after reaction, for example, 0.05 to 5 mol, preferably 0.1 to 2.5 mol relative to 1 mol of 1,4-dicyanocyclohexane.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, 1,4-dicyanocyclohexane, a catalyst, a hydrogen, and as necessary a solvent and ammonia are introduced from the reactor top or bottom, and are allowed to react at a predetermined temperature.

The reaction pressure is generally 0.1 to 20 MPa (gauge pressure), preferably 0.5 to 10 MPa (gauge pressure), even more preferably 0.5 to 8 MPa (gauge pressure), particularly preferably 0.5 to 5 MPa (gauge pressure).

The reaction temperature is, in view of reactivity and selectivity, for example, 50 to 250° C., preferably 50 to 200° C., more preferably 70 to 150° C., and preferably, the reaction temperature is increased continuously or stepwise during the hydrogenation reaction.

After the reaction, 1,4-bis(aminomethyl)cyclohexane can be separated from the reaction mixture by a known method, for example, by filtration, distillation, etc.

The thus produced 1,4-bis(aminomethyl)cyclohexane contains a cis isomer and a trans isomer.

The 1,4-bis(aminomethyl)cyclohexane has a trans isomer content of, for example, 20 mol % or more, preferably 30 mol % or more, more preferably 40 mol % or more, and for example, 90 mol % or less, preferably 80 mol % or less, more preferably 70 mol % or less.

Next, in this method, the produced 1,4-bis(aminomethyl)cyclohexane as described above is heated along with a catalyst under a hydrogen atmosphere, and the cis isomer in the 1,4-bis(aminomethyl)cyclohexane is isomerized to trans isomer, thereby increasing the trans isomer content.

The catalyst used in the isomerization step includes, for example, palladium, platinum, ruthenium, and rhodium, and preferably, palladium, and ruthenium are used.

These catalysts are preferably prepared as a supported catalyst. Examples of carriers for such catalysts include activated carbon, alumina, titania, silica, and diatomite, and preferably, activated carbon, alumina, titania, and silica is used. Particularly, in view of industrial handling, an alumina-supported catalyst of ruthenium is used.

The amount of metal (e.g., palladium, platinum, ruthenium, rhodium, etc.) supported is in the range of, for example, 0.05 to 30 mass %, preferably 0.1 to 20 mass %, of the total amount including the catalyst carrier.

The mixing ratio of the isomerization catalyst is set suitably in accordance with the purpose and application.

In the isomerization step, hydrogen used in the isomerization may be of industrial quality, and hydrogen may contain inert gas (e.g., nitrogen, methane, etc.), but the hydrogen concentration is preferable 50% or more.

The heating conditions in the isomerization reaction are as follows: the heating temperature is, for example, 120° C. or more, preferably 150° C. or more, and for example, 270° C. or less, preferably 240° C. or less. The pressure conditions are, for example, 1 MPa (gauge pressure) or more, preferably 2 MPa (gauge pressure) or more, and for example, 20 MPa (gauge pressure) or less, preferably 10 MPa (gauge pressure) or less.

The heating time is, for example, 0.5 hours or more, preferably 1 hour or more, and for example, 20 hours or less, preferably 10 hours or less.

Furthermore, as necessary, a solvent can also be added.

Examples of the solvent include aliphatic hydrocarbons such as hexane, heptane, and octane; alicyclic hydrocarbons such as cyclohexane, and methylcyclohexane; ethers such as tetrahydrofuran, and dioxane; aromatic hydrocarbons such as toluene, xylene, and ethylbenzene; and alcohols such as methanol, and ethanol.

Of these solvents, aliphatic hydrocarbons such as hexane, heptane, and octane; alicyclic hydrocarbons such as cyclohexane, and methylcyclohexane; and ethers such as tetrahydrofuran, and dioxane, which are stable under reaction conditions, are preferable.

The mixing ratio of the solvent is set suitably in accordance with the purpose and application.

With the above conditions, cis isomer of 1,4-bis(aminomethyl)cyclohexane can be isomerized to trans isomer, and the trans isomer content can be increased.

The 1,4-bis(aminomethyl)cyclohexane after the isomerization reaction has a trans isomer content of, for example, 70 mol % or more, preferably 75 mol % or more, more preferably 79 mol % or more, and for example, 95 mol % or less, preferably 93 mol % or less, more preferably 90 mol % or less.

It is assumed that the above-described isomerization reaction causes cyclization of 1,4-bis(aminomethyl)cyclohexane, generating the above-described compound represented by formula (2).

The 1,4-bis(aminomethyl)cyclohexane after isomerization reaction contains the above-described compound represented by formula (2) of, for example, 0.005 mass % or more, preferably 0.01 mass % or more, more preferably, 0.1 mass % or more, and for example, 3 mass % or less, preferably 1.5 mass % or less relative to a total amount thereof.

In this method, as necessary, 1,4-bis(aminomethyl)cyclohexane is subjected to distillation and purification so that the amounts of the trans isomer and the above-described compound represented by formula (2) contained can be adjusted.

The purification method is not particularly limited, and an industrial separation technique, for example, distillation and crystallization can be used.

When purification is performed by distillation, distillation column can be performed with a plate column or packed column. The number of stages in the rectifying column, the reflux ratio, and the distillation rate can be set suitably based on the trans isomer content that is necessary for 1,4-bis(aminomethyl)cyclohexane after purification, and are not limited particularly. The distillation conditions include, to be specific, the following: the theoretical plate number of the distillation column (packed column) of, for example, 2 or more, preferably 5 or more, and for example, 60 or less, preferably 40 or less.

The operation pressure of the distillation column is not particularly limited, but because 1,4-bis(aminomethyl)cyclohexane may undergo undesirable changes such as transformation into a high boiling component at high temperature, reduced pressure conditions are preferable to set the operation temperature of the distillation column lower.

The column top pressure of the distillation column is, for example, 2 kPa or more, preferably 3 kPa or more, and for example, 10 kPa or less, preferably 5 kPa or less.

The reflux ratio of the column top side is, for example, 0.01 or more, preferably 0.1 or more, and for example, 60 or less, preferably 40 or less.

The column top temperature of the distillation column is, for example, 130° C. or more, preferably 140° C. or more, and for example, 200° C. or less, preferably 190° C. or less. The column bottom temperature is, for example, 130° C. or more, preferably 180° C. or more, and for example, 280° C. or less, preferably 260° C. or less.

With the above conditions, the amounts of the trans isomer and the above-described compound represented by formula (2) of 1,4-bis(aminomethyl)cyclohexane can be adjusted.

The 1,4-bis(aminomethyl)cyclohexane has a trans isomer content of, as described above, for example, 70 mol % or more, preferably 75 mol % or more, more preferably 80 mol % or more, and for example, 95 mol % or less, preferably 93 mol % or less, more preferably 90 mol % or less.

The 1,4-bis(aminomethyl)cyclohexane contains the above-described compound represented by formula (2) of, as described above, for example, 0.005 mass % or more, preferably 0.01 mass % or more, more preferably 0.1 mass % or more, and for example, 3 mass % or less, preferably 1.5 mass % or less relative to a total amount thereof.

The method for producing 1,4-bis(aminomethyl)cyclohexane is not particularly limited as long as the amounts of the trans isomer and the above-described compound represented by formula (2) contained can be adjusted to the amounts as described above, and various methods can be used. For example, 1,4-bis(aminomethyl)cyclohexane can be heated as described above to cause isomerization reaction, and subjected to distillation and purification for use. Furthermore, commercially available para-xylylenediamine may be subjected to nuclear hydrogenation reaction by general methods to produce 1,4-bis(aminomethyl)cyclohexane in which the trans isomer and the cis isomer are mixed, and then as described above may be subjected to isomerization reaction by heating, and distillation and purification for use.

Then, in this method, 1,4-bis(aminomethyl)cyclohexane is subjected to isocyanization by phosgenation method.

The phosgenation method can be performed, to be more specific, by a method (hereinafter may be referred to as cold/hot two-stage phosgenation method) in which 1,4-bis(aminomethyl)cyclohexane is directly allowed to react with phosgene; or a method (hereinafter may be referred to as amine hydrochloride phosgenation method) in which hydrochloride, which is produced by allowing 1,4-bis(aminomethyl)cyclohexane to react with hydrochloric acid, is allowed to react with phosgene in an inactive solvent (described later).

In the cold/hot two-stage phosgenation method, for example, first, an inactive solvent is introduced to a reactor capable of stirring and provided with a phosgene inlet tube, and then the pressure in the reaction system is set to, for example, normal pressure to 1 MPa (gauge pressure), preferably normal pressure to 0.5 MPa (gauge pressure), and the temperature is set to, for example, 0 to 80° C., preferably 0 to 60° C.

Examples of the inactive solvent include aromatic hydrocarbons such as benzene, toluene, xylene, ethylbenzene, etc.; aliphatic acid esters such as ethyl acetate, butyl acetate, amyl acetate, etc.; aromatic carboxylic acid esters such as methyl salicylate, dimethyl phthalate, dibutyl phthalate, methyl benzoate, etc.; chlorinated aromatic hydrocarbons such as monochlorobenzene, orthodichlorobenzene, paradichlorobenzene, trichlorobenzene, etc.; and chlorinated hydrocarbons such as chloroform, carbon tetrachloride, etc.

These inactive solvents may be used singly or in combination of two or more. Furthermore, these inactive solvents can be recovered, and purified, for example, by distillation after reaction with phosgene, and can be reused.

The amount of the inactive solvent blended (total amount) relative to 100 parts by mass of material 1,4-bis(aminomethyl)cyclohexane is, for example, 400 to 3000 parts by mass, preferably 500 to 2000 parts by mass.

Next, in this method, 1 to 10 times mol, preferably 1 to 6 times mol of phosgene is introduced relative to one amino group of 1,4-bis(aminomethyl)cyclohexane, and 1,4-bis(aminomethyl)cyclohexane dissolved in the above-described inactive solvent is added. During this time, the reaction liquid is kept at, for example, 0 to 80° C., preferably 0 to 60° C., and at the same time, generated hydrogen chloride is released outside of the reaction system via the reflux condenser (cold phosgenation reaction). The contents of the reactor are thus formed into a slurry.

In the cold phosgenation reaction, a carbamoyl chloride compound and amine hydrochloride are produced.

Next, in this method, the pressure in the reaction system is set to, for example, normal pressure to 1 MPa (gauge pressure), preferably 0.05 to 0.5 MPa (gauge pressure), and the temperature is increased, for example, in a temperature range of 80 to 180° C. in, for example, 30 minutes to 5 hours. After the temperature increase, for example, the reaction is allowed to continue for 30 minutes to 8 hours, thereby dissolving the slurry liquid completely (hot phosgenation reaction).

In the hot phosgenation reaction, at the time of temperature increase and the high temperature reaction, the dissolved phosgene is evaporated and escapes outside the reaction system via the reflux condenser, and therefore phosgene is introduced appropriately until the reflux amount from the reflux condenser can be confirmed.

After the termination of the hot phosgenation reaction, an inactive gas such as nitrogen gas is introduced into the reaction system at, for example, 80 to 180° C., preferably 90 to 160° C., thereby purging dissolved excessive phosgene and hydrogen chloride.

At this time, excessively introduced phosgene can be recovered, purified, and reused. The hydrogen chloride can also be recovered, and allowed to react with oxygen in air to allow oxidation of hydrochloric acid for example, by a known method, to produce chlorine. The chlorine is allowed to react with carbon monoxide so that it can be reused as phosgene.

In the hot phosgenation reaction, carbamoyl chloride compound produced in the cold phosgenation reaction is thermally decomposed, 1,4-bis(isocyanatomethyl)cyclohexane is produced, and furthermore, amine hydrochloride of 1,4-bis(isocyanatomethyl)cyclohexane is phosgenated, thereby producing 1,4-bis(isocyanatomethyl)cyclohexane, and the above-described compound represented by formula (2) is phosgenated, thereby producing the above-described compound represented by formula (1).

Meanwhile, in phosgenation of amine hydrochloride, first, hydrochloride of 1,4-bis(aminomethyl)cyclohexane is synthesized.

To be specific, for example, an inactive solvent and 1,4-bis(aminomethyl)cyclohexane are introduced to a reactor capable of stirring and provided with a hydrochloric acid gas inlet tube, and a phosgene inlet tube, and then the pressure in the reaction system is set to, for example, normal pressure to 1 MPa (gauge pressure), preferably normal pressure to 0.5 MPa (gauge pressure), and the temperature is set to, for example, 0 to 120° C., preferably 0 to 100° C. The amount of the inactive solvent blended (total amount) relative to 100 parts by mass of material 1,4-bis(aminomethyl)cyclohexane is, for example, 400 to 3000 parts by mass, preferably 500 to 2000 parts by mass.

Then, for example, 1 to 5 times mol, preferably 1 to 3 times mol of hydrochloric acid gas relative to one mol of amino group of 1,4-bis(aminomethyl)cyclohexane is introduced. Hydrochloride of 1,4-bis(aminomethyl)cyclohexane is synthesized in this manner. Excessive hydrogen chloride used at this time is as necessary purified, and can be reused in the hydrochloride preparation step.

Next, in this method, the reaction temperature is maintained at, for example, 80 to 180° C., preferably 90 to 160° C., and the reaction pressure is maintained at, for example, normal pressure to 1.0 MPa (gauge pressure), preferably 0.05 to 0.5 MPa (gauge pressure), and phosgene is introduced for 1 to 10 hours so that the total phosgene amount is 1 to 10 times the stoichiometric amount.

With the above conditions, 1,4-bis(aminomethyl)cyclohexane is isocyanized, 1,4-bis(isocyanatomethyl)cyclohexane is produced, and the above-described compound represented by formula (2) is phosgenated, and the above-described compound represented by formula (1) is produced.

The reaction progress can be assumed based on the amount of the hydrogen chloride gas generated, and when the undissolved slurry in the above-described inactive solvent disappeared and the reaction liquid became clear and homogeneous. The generated hydrogen chloride is released, for example, outside the reaction system via the reflux condenser. At the time of reaction termination, the dissolved excessive phosgene and hydrogen chloride are purged by the above-described method. Thereafter, cooling is performed, and the inactive solvent is distilled off under reduced pressure. In this method as well, inactive reaction solvent, hydrogen chloride, and phosgene can be recovered, purified, and reused.

Furthermore, after production of 1,4-bis(isocyanatomethyl)cyclohexane by either method by isocyanization of 1,4-bis(aminomethyl)cyclohexane, 1,4-bis(aminomethyl)cyclohexane can be recovered from tar, i.e., reaction residue. Tar can be recovered by, for example, a known method, by allowing to react with supercritical water or carbon dioxide, or subcritical water or carbon dioxide to produce 1,4-bis(aminomethyl)cyclohexane.

The thus produced 1,4-bis(isocyanatomethyl)cyclohexane has a trans isomer content of, for example, 70 mol % or more, preferably 75 mol % or more, more preferably 80 mol % or more, and for example, 95 mol % or less, preferably 93 mol % or less, more preferably 90 mol % or less.

The 1,4-bis(isocyanatomethyl)cyclohexane contains, for example, 0.1 ppm or more, preferably 0.4 ppm or more, more preferably 1 ppm or more, and for example, 1000 ppm or less, preferably 500 ppm or less, more preferably 300 ppm or less of the above-described compound represented by formula (1).

In this method, as necessary, the 1,4-bis(isocyanatomethyl)cyclohexane produced as described above is heated to adjust the amount of the above-described compound represented by formula (1) contained.

The heating conditions are as follows: the heating temperature is, for example, 160° C. or more, preferably 180° C. or more, and for example, 220° C. or less, preferably 200° C. or less. The heating time is, for example, 1 hour or more, preferably 2 hours or more, and for example, 24 hours or less, preferably 12 hours or less.

In this method, as necessary, 1,4-bis(isocyanatomethyl)cyclohexane is distilled and purified so that the amount of the above-described compound represented by formula (1) can be adjusted. The purification method is not particularly limited, and an industrial separation technique, for example, distillation and crystallization can be used.

When purification is performed by distillation, distillation column can be a plate column or a packed column. The distillation conditions can be set suitably in accordance with the amount of the above-described compound represented by formula (1) contained necessary for 1,4-bis(isocyanatomethyl)cyclohexane after purification, and to be specific, the theoretical plate number of distillation column (packed column) is, for example, 2 or more, preferably 5 or more, and for example, 60 or less, preferably 40 or less.

The column top pressure of the distillation column is, for example, 0.1 kPa or more, preferably 0.15 kPa or more, and for example, 4 kPa or less, preferably 2.5 kPa or less.

The reflux ratio is, for example, 0.01 or more, preferably 0.1 or more, and 60 or less, preferably 40 or less.

The column top temperature of the distillation column is, for example, 110° C. or more, preferably 120° C. or more, and for example, 180° C. or less, preferably 170° C. or less.

The column bottom temperature is, for example, 120° C. or more, preferably 130° C. or more, and for example, 190° C. or less, preferably 180° C. or less.

In this method, the distillation rate, i.e., a fraction to be recovered, is in the range of, for example, 1 mass % or more, preferably 5 mass % or more, and for example, 99 mass % or less, preferably 95 mass % or less.

With the above conditions, the amount of the above-described compound represented by formula (1) contained can be adjusted.

The 1,4-bis(isocyanatomethyl)cyclohexane has a trans isomer content of, as described above, for example, 70 mol % or more, preferably 75 mol % or more, more preferably 80 mol % or more, and for example, 95 mol % or less, preferably 93 mol % or less, more preferably 90 mol % or less.

The 1,4-bis(isocyanatomethyl)cyclohexane contains the above-described compound represented by formula (1) in an amount of, as described above, for example, 0.1 ppm or more, preferably 0.4 ppm or more, more preferably 1 ppm or more, and for example, 300 ppm or less, preferably 200 ppm or less, more preferably 100 ppm or less.

The bottom portion (tar portion) and the high boiling point component containing 1,4-bis(isocyanatomethyl)cyclohexane produced in the distillation step can be recovered and then thereafter 1,4-bis(isocyanatomethyl)cyclohexane contained therein can be recovered by using, for example, a thin-film evaporator. Furthermore, a portion of these can be returned into the distillation step to purify 1,4-bis(isocyanatomethyl)cyclohexane to be recovered.

When the 1,4-bis(isocyanatomethyl)cyclohexane contains the trans isomer and the above-described compound represented by formula (1) in amounts in the above-described specific ranges, storage stability is excellent. Furthermore, when the 1,4-bis(isocyanatomethyl)cyclohexane contains the trans isomer and the above-described compound represented by formula (1) in amounts in the above-described specific ranges, a polyurethane resin having various excellent physical properties can be produced.

To the 1,4-bis(isocyanatomethyl)cyclohexane, for example, a stabilizer can be added.

Examples of the stabilizer include antioxidants, acidic compounds, compounds containing sulfonamide groups, and organic phosphite.

Examples of the antioxidant include hindered phenolic antioxidants, and specific examples include 2,6-di(t-butyl)-4-methylphenol, 2,4,6-tri-t-butylphenol, 2,2'-methylenebis-(4-methyl-6-t-butylphenol), 2,2'-thio-bis-(4-methyl-6-t-butylphenol), 4,4'-thio-bis(3-methy-6-t-butylphenol), 4,4'-butylidene-bis-(6-t-butyl-3-methylphenol), 4,4'-methylidyne-bis-(2,6-di-t-butylphenol), 2,2'-methylene-bis-[4-methyl-6-(1-methylcyclohexyl)-phenol], tetrakis-[methylene-3-(3,5-di-t-butyl-4-hydroxyphenyl)-propionyl]-methane, 1,3,5-trimethyl-2,4,6-tris-(3,5-di-t-butyl-4-hydroxyphenyl)-propionyl-methane, 1,3,5-trimethyl-2,4,6-tris-(3,5-di-t-butyl-4-hydroxybenzyl)-benzene, N,N'-hexamethylene-bis-(3,5-di-t-butyl-4-hydroxyhydrocinnamic acid amide, 1,3,5-tris-(3,5-di-t-butyl-4-hydroxybenzyl)-isocyanurate, 1,1,3-tris-(5-t-butyl-4-hydroxy-2-methylphenyl)-butane, 1,3,5-tris-(3,5-di-t-butyl-4-hydroxybenzyl)-mesitylene, ethylene glycol-bis-[3,3-bis-(3'-t-butyl-4'-hydroxyphenyl)-butyrate, 2,2'-thiodiethyl-bis-3-(3,5-di-t-butyl-4-hydroxyphenyl)-propionate, di-(3-t-butyl-4'-hydroxy-5-methylphenyl)-dicyclopentadiene, 2,2'-methylene-bis-(4-methyl-6-cyclohexylphenol), 1,6-hexanediol-bis-(3,5-di-t-butyl-4-hydroxyphenyl)-propionate, 2,4-bis-(n-octylthio)-6-(4-hydroxy-3,5-di-t-butylanilino)-1,3,5-triazine, diethyl-3,5-di-t-butyl-4-hydroxybenzylphosphonate, triethylene glycol-bis-3-(t-butyl-4-hydroxy-5-methylphenyl)-propionate, 3,9-bis[2-[3-(3-tert-butyl-4-hydroxy-5-methylphenyl)propionyloxy]-1,1-dimethylethyl]-2,4,8,10-tetraoxaspiro[5.5]undecane, 1,3,5-tris(4-tert-butyl-3-hydroxy-2,6 dimethylbenzyl)-1,3,5-tri azine-2,4,6-(1H,3H,5H)-trione, and also include, for example, IRGANOX1010, IRGANOX1076, IRGANOX1098, IRGANOX1135, IRGANOX1726, IRGANOX245, IRGANOX3114, and IRGANOX3790 (all manufactured by BASF Japan Ltd., trade name), and SUMILAZER GA-80 (Manufactured by Sumitomo Chemical Co., Ltd.), and Lowinox 1790 (manufactured by Chemtura Corporation).

These antioxidants may be used singly or in combination of two or more.

Examples of the acidic compound include organic acidic compounds, to be specific, phosphoric acid, phosphate, phosphite, hypophosphite, formic acid, acetic acid, propionic acid, hydroxyacetic acid, oxalic acid, lactic acid, citric acid, malic acid, sulfonic acid, sulfonate, phenol, enol, imide, and oxime.

These acidic compounds may be used singly or in combination of two or more.

Examples of the compound containing sulfonamide groups include aromatic sulfonamides and aliphatic sulfonamides.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in combination of two or more.

Examples of organic phosphites include organic diester phosphonate, and organic triester phosphonate, to be more specific, for example, monophosphites such as triethyl phosphite, tributyl phosphite, tris(2-ethylhexyl)phosphite, tridecyl phosphite, trilauryl phosphite, tris(tridecyl)phosphite, tristearyl phosphite, triphenyl phosphite, tris(nonylphenyl) phosphite, tris(2,4-di-t-butylphenyl)phosphite, diphenyldecyl phosphite, and diphenyl(tridecyl)phosphite; di, tri, or tetra phosphites derived from polyhydric alcohols such as distearyl.pentaerythrityl.diphosphite, di.dodecyl.pentaerythritol.diphosphite, di.tridecyl.pentaerythritol.diphosphite, dinonylphenyl.pentaerythritol.diphosphite, tetraphenyl.tetra.tridecyl.pentaerythrityl.tetra phosphite, tetraphenyl.dipropylene glycol.diphosphite, and tripentaerythritol.tri phosphite; and diphosphites derived from bisphenol compounds such as di.alkyl.bisphenol A.diphosphite having 1 to 20 carbons, and 4,4'-butylidene-bis(3-methyl-6-t-butylphenyl-di.tridecyl)phosphite; poly phosphites such as hydrogenated bisphenol A phosphite polymers (molecular weight 2400 to 3000); and tris(2,3-dichloropropyl)phosphate.

These organic phosphites may be used singly or in combination of two or more.

As the stabilizer, preferably, antioxidants, acidic compounds, or a compound containing a sulfonamide group is used. More preferably, to 1,4-bis(isocyanatomethyl)cyclohexane, an antioxidant and an acidic compound and/or a compound containing a sulfonamide group are blended so that 1,4-bis(isocyanatomethyl)cyclohexane contains these.

By adding these stabilizers, improvement in storage stability of 1,4-bis(isocyanatomethyl)cyclohexane, and an isocyanate-modified product (described later) produced by using 1,4-bis(isocyanatomethyl)cyclohexane can be achieved.

The mixing ratio of the stabilizer is not particularly limited, and is appropriately selected according to necessity and its application.

To be specific, the mixing ratio of the antioxidant is, for example, 0.0005 to 0.05 parts by mass relative to 100 parts by mass of 1,4-bis(isocyanatomethyl)cyclohexane.

The mixing ratio of the acidic compound and/or the compound containing a sulfonamide group (when used in combination, a total thereof) is, for example, 0.0005 to 0.05 parts by mass relative to 100 parts by mass of 1,4-bis(isocyanatomethyl)cyclohexane.

The present invention further includes a polyisocyanate composition produced by using the above-described 1,4-bis(isocyanatomethyl)cyclohexane.

The polyisocyanate composition is produced, to be more specific, by modifying the 1,4-bis(isocyanatomethyl)cyclohexane, and contains at least one of the functional group of (a) to (e) below.

(a) an isocyanurate group,
(b) an allophanate group,
(c) a biuret group,
(d) a urethane group, and
(e) a urea group.

The polyisocyanate composition containing the above-described functional group of (a) (isocyanurate group) is a trimer of 1,4-bis(isocyanatomethyl)cyclohexane, and for example, can be produced by allowing 1,4-bis(isocyanatomethyl)cyclohexane to react in the presence of a known isocyanurate-forming catalyst, thereby allowing trimerization.

The polyisocyanate composition containing the above-described functional group of (b)(allophanate group) is an allophanate-modified product of 1,4-bis(isocyanatomethyl)cyclohexane, and for example, can be produced by allowing 1,4-bis(isocyanatomethyl)cyclohexane and a monoalcohol to react, and then further allowing them to react in the presence of a known allophanate-forming catalyst.

The polyisocyanate composition containing the above-described functional group of (c) (biuret group) is a biuret-modified product of 1,4-bis(isocyanatomethyl)cyclohexane, and for example, can be produced by allowing 1,4-bis(isocyanatomethyl)cyclohexane to react with, for example, water, tertiary alcohol (e.g., t-butylalcohol, etc.), or secondary amine (e.g., dimethylamine, diethylamine, etc.), and then further allowing them to react in the presence of a known biuretizing catalyst.

The polyisocyanate composition containing the above-described functional group of (d) (urethane group) is a polyol modified product of 1,4-bis(isocyanatomethyl)cyclohexane, and can be produced, for example, by reaction between 1,4-bis(isocyanatomethyl)cyclohexane and a polyol component (e.g., dihydric alcohol and trihydric alcohol to be described later, and preferably, trimethylolpropane).

The polyisocyanate composition containing the above-described functional group of (e) (urea group) is a polyamine modified product of 1,4-bis(isocyanatomethyl)cyclohexane, and can be produced, for example, by reaction between 1,4-bis(isocyanatomethyl)cyclohexane, and water, or a polyamine component (described later).

The polyisocyanate composition containing at least one of the functional groups of the above-described (a) to (e) is sufficient, and can contain two or more of the functional groups of the above-described (a) to (e). Such a polyisocyanate composition is produced by suitably combining the above-described reactions.

As the polyisocyanate composition, preferably, a trimer (polyisocyanate composition containing an isocyanurate group) of 1,4-bis(isocyanatomethyl)cyclohexane is used.

The trimer of 1,4-bis(isocyanatomethyl)cyclohexane may further contain, in addition to the isocyanurate group, a polyisocyanate having an iminooxadiazinedione group.

The above-described 1,4-bis(isocyanatomethyl)cyclohexane contains the trans isomer and the above-described compound represented by formula (1) in amounts in the above-described specific ranges, and therefore polyurethane resin having various excellent physical properties can be produced.

The above-described polyisocyanate composition is produced by using the above-described 1,4-bis(isocyanatomethyl)cyclohexane, and therefore by using the polyisocyanate composition, a polyurethane resin having various excellent physical properties can be produced.

The present invention includes a polyurethane resin produced by using the above-described 1,4-bis(isocyanatomethyl)cyclohexane and/or the above-described polyisocyanate composition.

To be specific, the polyurethane resin of the present invention can be produced by allowing a polyisocyanate component containing the above-described 1,4-bis(isocyanatomethyl)cyclohexane and/or the above-described polyisocyanate composition to react with an active hydrogen group-containing component.

The polyisocyanate component contains, as essential components, the above-described 1,4-bis(isocyanatomethyl)cyclohexane and/or the above-described polyisocyanate composition.

The polyisocyanate component may contain, as an optional component, other polyisocyanates, such as for example, aliphatic polyisocyanate, alicyclic polyisocyanate (excluding 1,4-bis(isocyanatomethyl)cyclohexane), aralkyl polyisocyanate, and aromatic polyisocyanate in the range that does not damage the excellent effects of the present invention.

Examples of the aliphatic polyisocyanate include aliphatic diisocyanates such as trimethylene diisocyanate, tetramethylene diisocyanate, pentamethylene diisocyanate, hexamethylene diisocyanate, 1,2-propylene diisocyanate, 1,2-butylene diisocyanate, 2,3-butylene diisocyanate, 1,3-butylene diisocyanate, 2,4,4- or 2,2,4-trimethylhexamethylene diisocyanate, and 2,6-diisocyanatomethylcaproate.

Examples of the alicyclic polyisocyanate (excluding 1,4-bis(isocyanatomethyl)cyclohexane) include alicyclic diisocyanates such as 1,3-cyclopentane diisocyanate, 1,4-cyclohexane diisocyanate, 1,3-cyclohexane diisocyanate, 3-isocyanatomethyl-3,5,5-trimethylcyclohexyl isocyanate (also called: isophorone diisocyanate), 4,4'-methylenebis (cyclohexyl isocyanate), methyl-2,4-cyclohexane diisocyanate, methyl-2,6-cyclohexane diisocyanate, 1,3-bis(isocyanatomethyl)cyclohexane, 1,3-bis(isocyanato ethyl) cyclohexane, 1,4-bis(isocyanato ethyl)cyclohexane, 2,5- or 2,6-bis(isocyanatomethyl) norbornane (NBDI), and a mixture thereof.

Examples of the aralkyl polyisocyanate include aralkyl diisocyanates such as 1,3- or 1,4-xylylene diisocyanate or a mixture thereof, 1,3- or 1,4-tetramethylxylylene diisocyanate or a mixture thereof, and ω,ω'-diisocyanato-1,4-diethylbenzene.

Examples of the aromatic polyisocyanate include aromatic diisocyanates such as 2,4-tolylene diisocyanate, 2,6-tolylene diisocyanate, and a mixture of isomers of these tolylene diisocyanates; 4,4'-diphenylmethane diisocyanate, 2,4'-diphenylmethane diisocyanate, 2,2'-diphenylmethane diisocyanate, and a mixture of any isomers of these diphenylmethane diisocyanates; toluylene diisocyanate; p-phenylene diisocyanate; and naphthalene diisocyanate.

Furthermore, derivatives of these polyisocyanates can also be used in combination. To be more specific, multimers (dimers or trimers (e.g., isocyanurate-modified products)) of these polyisocyanates; a biuret-modified polyisocyanate, an allophanate-modified polyisocyanate, a polyol-modified polyisocyanate, an oxadiazinetrione-modified polyisocyanate, a carbodiimide-modified polyisocyanate, or an urethodione-modified polyisocyanate may be used in combination.

When the above-described 1,4-bis(isocyanatomethyl)cyclohexane and/or the above-described polyisocyanate composition are used in combination with other polyisocyanates, their mixing ratios relative to a total amount of the polyisocyanate component are as follows. The above-described 1,4-bis(isocyanatomethyl)cyclohexane and/or the above-described polyisocyanate composition are contained in an amount of 10 mol % or more, preferably 30 mol % or more, and for example, 90 mol % or less, preferably 70 mol % or less. Furthermore, other polyisocyanate is contained in an amount of 10 mol % or more, preferably 30 mol % or more, and for example, 90 mol % or less, preferably 70 mol % or less.

In the present invention, examples of the active hydrogen group-containing component include polyol components (component mainly containing polyol having two or more hydroxyl groups), polythiol components (component mainly containing polythiol having two or more mercapto groups (thiol group)), and polyamine components (compound mainly containing polyamine having two or more amino groups).

Examples of the polyol component in the present invention include low-molecular-weight polyols and high-molecular weight polyols.

Low-molecular-weight polyols are compounds having two or more hydroxyl groups and a number average molecular weight of below 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, alkane (7 to 22) diol, diethylene glycol, triethylene glycol, dipropylene glycol, 3-methyl-1,5-pentanediol, alkane-1,2-diol (C17 to 20), isosorbide, 1,3- or 1,4-cyclohexanedimethanol, and a mixture thereof, 1,4-cyclohexanediol, hydrogenation bisphenol A, 1,4-dihydroxy-2-butene, 2,6-dimethyl-1-octene-3,8-diol, and bisphenol A; trihydric alcohols such as glycerin and trimethylolpropane; tetrahydric alcohols such as tetramethylolmethane (pentaerythritol) and diglycerol; pentahydric alcohols such as xylitol; hexahydric alcohols such as sorbitol, mannitol, allitol, iditol, dulcitol, altritol, inositol, and dipentaerythritol; heptahydric alcohol such as perseitol; and octahydric alcohols such as sucrose.

The low molecular-weight polyol also include a polyalkylene oxide (random and/or block copolymer of two types or more of alkylene oxide) produced by adding alkylene oxides such as ethylene oxide and propylene oxide with those low molecular-weight polyols as initiators, and having a number average molecular weight of less than 400.

High-molecular weight polyols are compounds having two or more hydroxyl groups and having a number average molecular weight of 400 or more, and examples thereof include polyether polyol, polyester polyol, polycarbonate polyol, polyurethane polyol, epoxy polyol, vegetable oil polyol, polyolefin polyol, acrylic polyol, and vinyl monomer-modified polyol.

Examples of the polyether polyol include polyalkylene polyol, polytetramethylene ether glycol, and polytrimethylene ether glycol.

Examples of the polyalkylene polyol include addition polymers of alkylene oxide (including a random and/or block copolymer of two or more kinds of alkylene oxide), such as ethylene oxide and propylene oxide, using the above-described low molecular-weight polyol or the aromatic/aliphatic polyamine (described later) as an initiator. Furthermore, polyethylene glycol can also be used. The CPR (controlled polymerization rate) of the polyalkylene polyol including polyethylene glycol is 5 or less, even more preferably 3 or less, and most preferably 2 or less. The CPR is measured in accordance with the method described in JIS K 1557-1. By using polyoxyalkylene polyol having a CPR in such a range, side reactions based on the isocyanate group in reaction with 1,4-bis(isocyanatomethyl)cyclohexane of the present invention can be suppressed.

Examples of polytetramethylene ether glycols include ring-opening polymerized product obtained by cation polymerization of tetrahydrofuran, and noncrystalline polytetramethylene ether glycol obtained by copolymerizing polymerization unit of tetrahydrofuran and the above-described dihydric alcohol.

Furthermore, plants derived polytetramethylene ether glycol, which is produced using tetrahydrofuran produced based on vegetable oil material such as furfural as a starting material, can also be used.

Examples of polytrimethylene ether glycol include a polyol produced by polycondensation reaction of plants derived 1,3-propanediol.

Examples of polyester polyols include a polycondensation product obtained by allowing the above-described low-molecular-weight polyol (preferably, dihydric alcohol) to react with polybasic acid under known conditions.

Examples of polybasic acids include saturated aliphatic dicarboxylic acids (C11 to 13) such as oxalic acid, malonic acid, succinic acid, methylsuccinic acid, glutaric acid, adipic acid, 1,1-dimethyl-1,3-dicarboxypropane, 3-methyl-3-ethylglutaric acid, azelaic acid, sebacic acid, etc.; unsaturated aliphatic dicarboxylic acids such as maleic acid, fumaric acid, itaconic acid, etc.; aromatic dicarboxylic acids such as orthophthalic acid, isophthalic acid, terephthalic acid, toluenedicarboxylic acid, naphthalenedicarboxylic acid, etc.; alicyclic dicarboxylic acids such as hexahydrophthalic acid, etc.; other carboxylic acids such as dimer acid, hydrogenated dimer acid, het acid, etc. and acid anhydrides derived from these carboxylic acids such as oxalic anhydride, succinic anhydride, maleic anhydride, phthalic anhydride, 2-alkyl (C12 to C18) succinic anhydride, tetrahydrophthalic anhydride, trimellitic anhydride, and hallides derived from these carboxylic acids such as oxalyl dichloride, adipoyl dichloride, and sebacoyl dichloride.

Examples of polyester polyols include plants derived polyester polyol obtained by condensation reaction of hydroxycarboxylic acid such as hydroxyl group-containing vegetable oil fatty acid (e.g., castor oil fatty acid containing ricinoleic acid, hydrogenated castor oil fatty acid containing 12-hydroxystearic acid, etc.) with the above-described low-molecular-weight polyol under known conditions.

Examples of polyester polyols include polycaprolactone polyol, and polyvalerolactone polyol obtained by ring-opening polymerization of lactones such as ε-caprolactone, γ-valerolactone, etc. using the above-described low-molecular-weight polyols (preferably, dihydric alcohol) as an initiator; and further lactone-based polyester polyols obtained by copolymerizing such a polycaprolactone polyol or polyvalerolactone polyol with the above-described dihydric alcohol.

Examples of polycarbonate polyols include ring-opening polymerization product of ethylene carbonate using the above-described low-molecular-weight polyols (preferably, dihydric alcohol) as an initiator, and noncrystalline polycarbonate polyols obtained by copolymerization of dihydric alcohols such as 1,4-butanediol, 1,5-pentanediol, 3-methyl-1,5-pentanediol, and 1,6-hexanediol with ring-opening polymerization product.

Polyurethane polyols can be produced as polyester polyurethane polyol, polyether polyurethane polyol, polycarbonate polyurethane polyol, or polyester polyether polyurethane polyol, by allowing polyester polyol, polyether polyol and/or polycarbonate polyol obtained as described above to react with the polyisocyanate (including 1,4-bis(isocyanatomethyl)cyclohexane. The same applies in the following) at an equivalent ratio (OH/NCO) of hydroxyl group to isocyanate group of more than 1.

Examples of epoxy polyols include epoxy polyols obtained by reaction of the above-described low-molecular-weight polyols with polyfunctional halohydrin such as epichlorohydrin, β-methylepichlorohydrin, etc.

Examples of vegetable oil polyols include hydroxyl group-containing vegetable oil such as castor oil, palm oil, etc. Examples thereof include castor oil polyol, and ester-modified castor oil polyol obtained by reaction of castor oil polyol with polypropylene polyol.

Examples of polyolefin polyols include polybutadiene polyol, and a partially saponified ethylene-vinyl acetate copolymer.

Examples of acrylic polyol include copolymers obtained by copolymerizing hydroxyl group-containing acrylate with a copolymerizable vinyl monomer that is copolymerizable with hydroxyl group-containing acrylate.

Examples of hydroxyl group-containing acrylates include 2-hydroxyethyl(meth)acrylate, hydroxypropyl(meth)acrylate, hydroxybutyl(meth)acrylate, 2,2-dihydroxymethylbutyl(meth)acrylate, polyhydroxyalkylmaleate, and polyhydroxyalkylfumarate. Preferably, 2-hydroxyethyl(meth)acrylate is used.

Examples of copolymerizable vinyl monomers include alkyl(meth)acrylate (1 to 12 carbon atoms) such as methyl (meth)acrylate, ethyl(meth)acrylate, propyl(meth)acrylate, isopropyl(meth)acrylate, butyl(meth)acrylate, isobutyl (meth)acrylate, s-butyl(meth)acrylate, t-butyl(meth)acrylate, pentyl(meth)acrylate, isopentyl(meth)acrylate, hexyl (meth)acrylate, isononyl(meth)acrylate, 2-ethylhexyl(meth) acrylate, cyclohexylacrylate, and isobornyl(meth)acrylate; aromatic vinyl monomers such as styrene, vinyltoluene, and ex-methylstyrene; vinyl cyanide such as (meth)acrylonitrile; vinyl monomers containing carboxyl groups such as (meth) acrylic acid, fumaric acid, maleic acid, and itaconic acid or their alkyl esters; alkanepolyol poly (meth)acrylate such as ethylene glycol di(meth)acrylate, butyleneglycol di(meth) acrylate, hexanediol di(meth)acrylate, oligoethylene glycol di(meth)acrylate, trimethylolpropane di(meth)acrylate, and trimethylolpropane tri(meth)acrylate; and vinyl monomers containing isocyanate groups such as 3-(2-isocyanato-2-propyl)-a-methylstyrene.

Acrylic polyol can be produced by copolymerizing these hydroxyl group-containing acrylates, and copolymerizable vinyl monomers in the presence of an appropriate solvent and a polymerization initiator.

Examples of acrylic polyol include silicone polyol and fluorine polyol.

Examples of silicone polyols include acrylic polyol in which as the copolymerizable vinyl monomer, for example, a silicone compound containing a vinyl group such as γ-methacryloxypropyltrimethoxy silane is blended in the above-described copolymerization of acrylic polyol.

Examples of fluorine polyols include acrylic polyol in which as the copolymerizable vinyl monomer, for example, a fluorine compound containing a vinyl group such as tetrafluoroethylene, or chlorotrifluoroethylene is blended in the above-described copolymerization of acrylic polyol.

The vinyl monomer-modified polyol can be produced by allowing the above-described high-molecular weight polyol to react with a vinyl monomer.

As the high-molecular weight polyol, preferably, a high-molecular weight polyol selected from polyether polyol, polyester polyol, and polycarbonate polyol is used.

Examples of vinyl monomers include the above-described alkyl(meth)acrylate, vinyl cyanide, and vinylidene cyanide. These vinyl monomers may be used singly or in combination of two or more. Of these vinyl monomers, preferably, alkyl(meth)acrylate is used.

The vinyl monomer-modified polyol can be produced by allowing these high-molecular weight polyols to react with vinyl monomers in the presence of, for example, a radical polymerization initiator (e.g., persulfate, organic peroxide, azo compound, etc.).

These polyol components may be used singly or in combination of two or more.

Examples of the polythiol component include aliphatic polythiols, aromatic polythiols, heterocyclic ring-containing polythiols, aliphatic polythiols containing a sulfur atom other than the mercapto group, aromatic polythiols containing a sulfur atom other than the mercapto group, and heterocyclic ring-containing polythiols containing a sulfur atom other than the mercapto group.

Examples of the aliphatic polythiol include methanedithiol, 1,2-ethanedithiol, 1,1-propanedithiol, 1,2-propanedithiol, 1,3-propanedithiol, 1,4-butanedithiol, 1,5-pentanedithiol, 2,2-propanedithiol, 1,6-hexanedithiol, 1,2,3-propanetrithiol, 1,1-cyclohexane dithiol, 1,2-cyclohexanedithiol, 2,2-dimethylpropane-1,3-dithiol, 3,4-dimethoxybutane-1,2-dithiol, 2-methylcyclohexane-2,3-dithiol, 1-methylcyclohexane-2,3-dithiol, bicyclo[2,2,1] hepta-exo-cis-2,3-dithiol, tetrakis(mercaptomethyl) methane, 1,1-bis(mercaptomethyl)cyclohexane, bis(2-mercaptoethyl)thiomalate, 2,3-dimercaptosuccinic acid (2-mercaptoethylester), 2,3-dimercapto-1-propanol (2-mercaptoacetate), 2,3-dimercapto-1-propanol (3-mercaptopropionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethylene glycol bis(2-mercaptoacetate), ethylene glycol bis (3-mercaptopropionate), trimethylolpropane bis(2-mercaptoacetate), trimethylolpropane bis(3-mercaptopropionate), 3-mercapto-1,2-propanediolbis(2-mercaptoacetate), 3-mercapto-1,2-propanedioldi(3-mercaptopropionate), trimethylolpropanetris(2-mercaptoacetate), trimethylolpropane (3-mercaptopropionate), trimethyloletanetris(2-mercaptoacetate), trimethyloletanetris(3-mercaptopropionate), pentaerythritol tetrakis(2-mercaptoacetate), pentaerythritol tetrakis(3-mercaptopropionate), glycerintris(2-mercaptoacetate), glycerintris(3-mercaptopropionate), 1,4-cyclohexanediolbis(2-mercaptoacetate), and 1,4-cyclohexanediolbis(3-mercaptopropionate).

Examples of the aromatic polythiol include 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2-bis(mercapto methyleneoxy)benzene, 1,3-bis(mercaptomethyleneoxy)benzene, 1,4-bis(mercaptomethyleneoxy)benzene, 1,2-bis(mercaptoethyleneoxy)benzene, 1,3-bis(mercaptoethyleneoxy)benzene, 1,4-bis(mercaptoethyleneoxy)benzene, 1,2,3-trimercapto benzene, 1,2,4-trimercapto benzene, 1,3,5-trimercapto benzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 1,2,3-tris(mercaptomethyleneoxy)benzene, 1,2,4-tris(mercaptomethyleneoxy)benzene, 1,3,5-tris(mercaptomethyleneoxy)benzene, 1,2,3-tris(mercaptoethyleneoxy)benzene, 1,2,4-tris(mercaptoethyleneoxy)benzene, 1,3,5-tris(mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 1,2,3,4-tetrakis(mercaptomethyleneoxy)benzene, 1,2,3,5-tetrakis(mercaptomethyleneoxy)benzene, 1,2,4,5-tetrakis(mercaptoethyleneoxy)benzene, 1,2,3,4-tetrakis(mercaptoethyleneoxy)benzene, 1,2,3,5-tetrakis(mercaptoethyleneoxy)benzene, 1,2,4,5-tetrakis(mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-di(p-methoxyphenyl)propane-2,2-dithiol, 1,3-diphenylpropane-2,2-dithiol, phenylmethane-1,1-dithiol, and 2,4-di(p-mercaptophenyl)pentane.

Examples of the heterocyclic ring-containing polythiol include 2-methylamino-4,6-dithiol-sym-triazine, 2-ethylamino-4,6-dithiol-sym-triazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine, and 2-thiobutyloxy-4,6-dithiol-sym-triazine.

Examples of the aliphatic polythiols containing a sulfur atom other than the mercapto group include bis(mercaptomethyl)sulfide, bis(mercaptoethyl)sulfide, bis(mercaptopropyl)sulfide, bis(mercaptomethylthio)methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, tetrakis(mercaptomehyithyliomethyl)methane, tetrakis(2-mercaptoethylthiomethyl)methane, tetrakis(3-mercaptopropylthiomethyl)methane, bis(2,3-dimercaptopropyl)sulfide, 2,5-dimercapto-1,4-dithiane, 2,5-dimercaptomethyl-1,4-dithiane, bis(mercaptomethyl)disulfide, bis(mercaptoethyl)disulfide, bis(mercaptopropyl)disulfide, and the like, and thioglycolic acid and mercaptopropionic acid esters of the above-mentioned compounds, hydroxymethylsulfide bis(2-mercapto acetate), hydroxymethylsulfide bis(3-mercaptopropionate), hydroxyethylsulfide bis(2-mercapto acetate), hydroxyethylsulfide bis(3-mercaptopropionate), hydroxypropylsulfide bis(2-mercaptoacetate), hydroxypropylsulfide bis(3-mercaptopropionate), hydroxymethyldisulfide bis(2-mercapto acetate), hydroxymethyldisulfide bis(3-mercaptopropionate), hydroxyethyldisulfide bis(2-mercapto acetate), hydroxyethyldisulfide bis(3-mercaptopropionate), hydroxypropyldisulfide bis(2-mercapto acetate), hydroxypropyldisulfide bis(3-mercaptopropionate), 2-mercaptoethylether bis(2-mercaptoacetate), 2-mercaptoethylether bis(3-mercaptopropionate), 1,2-bis[(2-mercaptoethyl)thio]-3-mercaptopropane, 1,4-dithiane-2,5-diol bis(2-mercapto acetate), 1,4-dithiane-2,5-diol bis(3-mercaptopropionate), thiodiglycolic acid bis(2-mercaptoethylester), thiodipropionic acid bis(2-mercaptoethylester), 4,4-thiodibutyric acid bis(2-mercaptoethylester), dithiodiglycolic acid bis(2-mercaptoethylester), dithiodipropionic acid bis(2-mercaptoethylester), 4,4-dithiodibutyric acid bis(2-mercaptoethylester), thioglycolic acid bis(2,3-dimercaptopropylester), thiodipropionic acid bis(2,3-dimercaptopropylester), dithioglycolic acid bis(2,3-dimercaptopropylester), dithiodipropionic acid bis(2,3-dimercaptopropylester), 1,2-bis(2-mercaptoethylthio)-3-propane thiol, 4-mercaptomethyl-1,8-dimercapto-3,6-dithiaoctane, 5,7-dimercaptomethyl-1,1-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithiethane.

Examples of the aromatic polythiols containing a sulfur atom other than the mercapto group include 1,2-bis(mercaptomethylthio)benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercaptomethylthio)benzene, 1,2,4,5-tetrakis(mercaptomethylthio)benzene, 1,2,3,4-tetrakis(mercaptoethylthio)benzene, 1,2,3,5-tetrakis(mercaptoethylthio)benzene, 1,2,4,5-tetrakis(mercaptoethylthio)benzene, and the like, and nuclear alkylated products of the above-mentioned compounds.

Examples of the heterocyclic ring-containing polythiols containing a sulfur atom other than the mercapto group include 3,4-thiophenedithiol, 2,5-dimercapto-1,3,4-thiadiazole, and the like, and thioglycolic acid esters and mercaptopropionic acid esters of the above-mentioned compounds.

Further examples of the polythiol component include halogen substituted compound of these polythiols, such as chlorine-substituted compound and bromine-substituted compound of the polythiol components.

These polythiols may be used singly or in combination of two or more.

Examples of polyamine components include aromatic polyamine, aralkyl polyamine, alicyclic polyamine, aliphatic polyamine, amino alcohol, an alkoxysilyl compound having a primary amino group, or a primary amino group and a secondary amino group, and polyoxyethylene group-containing polyamine.

Examples of aromatic polyamine include aromatic primary polyamines such as 2,4-tolylenediamine (2,4-diaminotoluene), 2,6-tolylenediamine (2,6-diaminotoluene), 4,4'-diphenylmethanediamine, 2,4'-diphenylmethanediamine, 2,2'-diphenylmethanediamine, 4,4'-diphenyletherdiamine, 2-nitrodiphenyl-4,4'-diamine, 2,2'-diphenylpropane-4,4'-diamine, 3,3'-dimethyldiphenylmethane-4,4'-diamine, 4,4'-diphenylpropane diamine, m-phenylenediamine, p-phenylenediamine, naphthylene-1,4-diamine, naphthylene-1,5-diamine, and 3,3'-dimethoxydiphenyl-4,4'-diamine; and aromatic secondary polyamines such as N,N'-dialkyl-2,4-tolylenediamine (N,N'-dialkyl-2,4-diaminotoluene), N,N'-dialkyl-2,6-tolylenediamine (N,N'-dialkyl-2,6-diaminotoluene), N,N'-dialkyl-4,4'-diphenylmethanediamine, N,N'-dialkyl-2,4'-diphenylmethanediamine, N,N'-dialkyl-2,2'-diphenylmethanediamine, N,N'-dialkyl-4,4'-diphenyletherdiamine, N,N'-dialkyl-2-nitrodiphenyl-4,4'-diamine, N,N'-dialkyl-2,2'-diphenylpropane-4,4'-diamine, N,N'-dialkyl-3,3'-dimethyldiphenylmethane-4,4'-diamine, N,N'-dialkyl-4,4'-diphenylpropane diamine, N,N'-dialkyl-m-phenylenediamine, N,N'-dialkyl-p-phenylenediamine, naphthylene-1,4-diamine, N,N'-dialkyl-naphthylene-1,5-diamine, and N,N'-dialkyl-3,3'-dimethoxydiphenyl-4,4'-diamine.

Examples of aralkyl polyamine include aralkyl primary polyamines such as 1,3- or 1,4-xylylenediamine or a mixture thereof, 1,3-tetramethylxylylenediamine (1,3-di(2-amino-2-methylethyl)benzene), and 1,4-tetramethylxylylenediamine (1,4-bis(2-amino-2-methylethyl)benzene); and aralkyl secondary polyamines such as N,N'-dialkyl-1,3-bis(aminomethyl)benzene, N,N'-dialkyl-1,4-bis(aminomethyl)benzene, N,N'-dialkyl-1,3-tetramethylxylylenediamine (N,N'-dialkyl-1,3-di(2-amino-2-methylethyl)benzene), and N,N'-dialkyl-1,4-tetramethylxylylenediamine (N,N'-dialkyl-1,4-bis(2-amino-2-methylethyl)benzene).

Examples of alicyclic polyamine include alicyclic primary polyamines such as 3-aminomethyl-3,5,5-trimethylcyclohexylamine (also called: isophoronediamine), 4,4'-dicyclohexylmethanediamine (also called: 4,4'-methylenebis(cyclohexylamine)), 4,4'-methylenebis(2-methylcyclohexylamine), 2,5 (2,6)-bis(aminomethyl) bicyclo[2.2. 1]heptane, 1,2-, 1,3- or 1,4-cyclohexanediamine, 1-amino-3-aminomethyl-3,5,5-trimethylcyclohexane, bis-(4-aminocyclohexyl) methane, 3,9-bis(3-amino-proropyl)-2,4,8,10-tetraoxaspiro[5,5]undecane, 1,3- and 1,4-bis(aminomethyl)cyclohexane, and a mixture thereof, hydrogenated 2,4-tolylenediamine, hydrogenated 2,6-tolylenediamine, and triaminocyclohexane; and alicyclic secondary polyamines such as N,N'-dialkyl-diaminocyclobutane, N,N'-dialkyl-isophoronediamine (N,N'-dialkyl-3-aminomethyl-3,5,5-trimethylcyclohexylamine), N,N'-diisopropyl-isophoronediamine (trade name: JEFLINK754, manufactured by Huntsman), N,N'-dialkyl-1,2-diaminocyclohexane, N,N'-dialkyl-1,3-diaminocyclohexane, N,N'-dialkyl-1,4-diaminocyclohexane, N,N'-dialkyl-1,3-bis(aminomethyl)cyclohexane, N,N'-dialkyl-1,4-bis(aminomethyl)cyclohexane, N,N'-dialkyl-4,4'-methylenebis(cyclohexylamine)(also called 4,4'-methylenebis(N-alkylcyclohexaneamine)), 4,4'-, methylenebis[N-(1-methylpropyl)cyclohexaneamine](trade name: CLEARLINK1000, manufactured by Dorf Ketal Chemicals), N,N'-dialkyl-4,4'-methylenebis(2-methylcyclohexylamine)(also called 4,4'-methylenebis(2-methyl-N-alkylcyclohexaneamine)), 4,4'-methylenebis[2-methyl-N-(1-methylpropyl)cyclohexaneamine](trade name: CLEARLINK3000, manufactured by Dorf Ketal Chemicals), N,N'-dialkyl-2,5-bis(aminomethyl) bicyclo[2,2,1]heptane, N,N'-dialkyl-2,6-bis(aminomethyl) bicyclo[2,2,1]heptane, N,N'-dialkyl-hydrogenated 2,4-tolylenediamine, N,N'-dialkyl-hydrogenated 2,6-tolylenediamine, and N,N',N"-trialkyl-triaminocyclohexane.

Examples of aliphatic polyamine include aliphatic primary polyamines such as ethylene diamine, propylene diamine, 1,3-propane diamine, 1,4-butanediamine, 1,3-pentanediamine, 1,5-pentanediamine, 1,6-hexamethylenediamine, 1,7-diaminoheptane, 1,8-diaminooctane, 1,9-diaminononane, 1,10-diaminodecane, 1,12-diaminododecane, 2,2,4-trimethylhexamethylenediamine, 2,4,4-trimethylhexamethylenediamine, tetramethylenediamine, hydrazine (including hydrate), 1,2,3-triaminopropane, triaminohexane, triaminononane, triaminododecane, 1,8-diamino-4-aminomethyloctane, 1,3,6-triaminohexane, 1,6,11-triaminoundecane, 3-aminomethyl-1,6-diaminohexane, diethylene triamine, triethylenetetramine, and tetraethylenepentamine; and aliphatic secondary polyamines such as N,N'-dialkyl-1,2-diaminoethane (N,N'-dialkyl-ethylene diamine), N,N'-dialkyl-1,3-diaminopropane, N,N'-dialkyl-1,4-diaminobutane (N,N'-dialkyl-1,4-tetramethylenediamine), N,N'-dialkyl-1,5-diaminopentane (N,N'-dialkyl-1,5-pentamethylenediamine), N,N'-dialkyl-1,6-diaminohexane (N,N'-dialkyl-1,6-hexamethylenediamine), N,N'-bis(1,2,2-trimethylpropyl)-1,6-hexanediamine (trade name: Ethacure90, Manufactured by Albemare), N,N'-dialkyl-1,7-diaminoheptane, N,N'-dialkyl-1,8-diaminooctane, N,N'-dialkyl-1,9-diaminononane, N,N'-dialkyl-1,10-diaminodecane, N,N'-dialkyl-1,12-diaminododecane, N,N'-dialkyl-2,2,4-trimethylhexamethylenediamine, N,N'-dialkyl-2,4,4-trimethyl hexamethylenediamine, N,N'-dialkyl-tetramethylenediamine, N,N',N"-trialkyl-1,2,3-triaminopropane, N,N',N"-trialkyl-triaminohexane, N,N',N"-trialkyl-triaminononane, N,N',N"-trialkyl-triaminododecane, N,N',N"-trialkyl-1,8-diamino-4-aminomethyloctane, N,N',N"-trialkyl-1,3,6-triaminohexane, N,N',N"-trialkyl-1,6,11-triaminoundecane, and N,N',N"-trialkyl-3-aminomethyl-1,6-diaminohexane.

Examples of aminoalcohol include N-(2-aminoethyl) ethanolamine.

Examples of alkoxysilyl compound having a primary amino group, or a primary amino group and a secondary amino group include alkoxysilyl group-containing monoamine such as γ-aminopropyltriethoxysilane, and N-phenyl-γ-aminopropyltrimethoxysilane; N-β(aminoethyl) γ-aminopropyltrimethoxysilane; and N-β(aminoethyl) γ-aminopropylmethyldimethoxysilane.

Examples of polyoxyethylene group-containing polyamines include polyoxyalkylene ether diamine such as polyoxyethylene ether diamine. To be more specific, examples thereof include PEG#1000 diamine manufactured by NOF Corporation, Jeffamine ED-2003, EDR-148, and XTJ-512 manufactured by Huntsman Inc.

These polyamine components may be used singly or in combination of two or more.

When the molecular weight of the polyurethane resin is adjusted, as the active hydrogen group-containing component, a monol and/or a monoamine can be used in combination with the above-described components.

Examples of the monol include methanol, ethanol, propanol, butanol, 2-ethylhexyl alcohol, stearyl alcohol, other alkanols (C5-38) and aliphatic unsaturated alcohol (C9-24), alkenyl alcohol, 2-propen-1-ol, alkadienol (C6-8), and 3,7-dimethyl-1,6-octadien-3-ol.

Examples of the monoamine include dimethylamine, diethylamine, di-n-propylamine, diisopropylamine, di-n-butylamine, diisobutylamine, di-t-butylamine, dihexylamine, 2-ethylhexylamine, 3-methoxypropylamine, 3-ethoxypropylamine, 3-(2-ethylhexyloxypropylamine), 3-(dodecyloxy) propylamine, and morpholine.

In the present invention, a known additive can optionally be added as necessary.

In the present invention, the polyisocyanate component contains above-described compound represented by formula (1) at a predetermined ratio, and therefore the polyurethane resin contains an amine compound corresponding to the above-described compound represented by formula (1), that is, a structure derived from the above-described compound represented by formula (2) at a predetermined corresponding ratio (that is, a predetermined ratio relative to the polyurethane resin).

Then, in the polyurethane resin of the present invention, the above-described 1,4-bis(isocyanatomethyl)cyclohexane and/or the above-described polyisocyanate composition are used as the polyisocyanate component. Therefore, the required physical properties for various applications can be improved.

Thus, the polyurethane resin of the present invention can be used in various applications including, for example, elastomers (polyurethane solution, aqueous polyurethane, heat melt molding (slush molding, rotational molding), urethane powder, thermoplastic urethane elastomer (TPU), thermosetting urethane elastomer (TSU), spray molding urethane, melt spinning or dry spinning elastic fiber), paints (mainly solution-based, powder-based curing agent: adduct, allophanate, biuret, urethodione, polyisocyanurate, iminooxadiazinedione, and a mixture thereof), industrial or hot melt adhesive, sealing material, polyurethane foam, and gel. Those can also be used for production of derivatives of, for example, polyimide, polyamide, polyamide-imide, and oxazoline.

Examples of the molded articles produced by using the polyurethane resin of the present invention include fiber, film, sheet, nonwoven fabric, film, sheet, sporting goods including golf ball, swimwear, compression wear, underwear, shoes, and grips, apparel, catheter, tubes, hose, endoscope cover material, housing coatings for smartphone and tablet, ink binder, coating material for solar batteries, eyewear materials for optical lens (eye glasses lens and sunglasses), eyewear frame, transparent resins, artificial or synthetic leather, RIM molded article, automobile interior and exterior members, bullet train members, transport members, roll, caster, tire, gel, foam, pad, and puff.

In the following, a production method of the polyurethane resin of the present invention in accordance with applications is explained.

First, description is given for a case where elastomers (TPU and TSU) are produced as the polyurethane resin of the present invention.

The polyisocyanate component for production of elastomers as the polyurethane resin of the present invention include the above-described 1,4-bis(isocyanatomethyl)cyclohexane and/or the above-described polyisocyanate composition, and preferably the above-described 1,4-bis(isocyanatomethyl)cyclohexane is used singly.

When producing the polyurethane resin of the present invention as elastomers, examples of the above-described active hydrogen group-containing component include the above-described polyol component.

For the active hydrogen group-containing component, preferably, the above-described high-molecular weight polyol is used.

When a thermoplastic urethane elastomer (TPU) is produced, more preferably, polyether polyols such as polytetramethylene ether glycol and polyethylene glycol, polyester polyol, polycaprolactone polyol, and polycarbonate polyol are used. In particular, when polyethylene glycol is used as the active hydrogen group-containing component, a thermoplastic urethane elastomer (TPU) having excellent moisture permeability can be produced, and furthermore, when polytetramethylene ether glycol, or polycarbonate polyol is used, a thermoplastic urethane elastomer (TPU) having excellent mechanical properties can be produced.

When a thermosetting urethane elastomer (TSU) is produced, more preferably, polyether polyol, polycaprolactone polyol, polyester polyol are used, and even more preferably, polytetramethylene ether glycol, and polycaprolactone polyol are used.

When producing the polyurethane resin of the present invention as elastomers, the high-molecular weight polyol has a hydroxyl number of, for example, 10 to 125 mgKOH/g, and a number average molecular weight of, for example, 400 to 5000, preferably 1000 to 3000, even more preferably 1000 to 2500.

The hydroxyl number can be determined by acetylation or phthalation according to method A or B of JIS K 1557-1. The hydroxyl number and the hydroxyl equivalent satisfy the relation of the following equation (1):

$$\text{Hydroxyl number} = 56100/\text{hydroxyl equivalent} \qquad (1)$$

The number average molecular weight can be determined by the hydroxyl equivalent and average functionality, and the average functionality can be determined by the following equation (2):

$$\text{Average functionality} = \text{sum of (functionality of each polyol} \times \text{the number of equivalents)/sum of the number of equivalents of each polyol)} \qquad (2)$$

As the active hydrogen group-containing component, as necessary, furthermore, for example, the above-described low molecular-weight polyol, polythiol component, polyamine component, monol and/or monoamine can be blended at a suitable ratio. Preferably, the low molecular-weight polyol and/or the polyamine component are blended, and more preferably, when a thermoplastic urethane elastomer (TPU) is produced, dihydric alcohol is blended, and when a thermosetting urethane elastomer (TSU) is produced, dihydric alcohol and trihydric alcohol are blended.

Then, the polyurethane resin of the present invention can be produced as an elastomer by a polymerization method such as bulk polymerization or solution polymerization.

In the bulk polymerization, for example, while the polyisocyanate component is stirred under a nitrogen flow, the active hydrogen group-containing component is added thereto, and the mixture is allowed to react at a reaction temperature of 50 to 250° C., preferably 50 to 200° C. for about 0.5 to 15 hours.

In the solution polymerization, the polyisocyanate component and the active hydrogen group-containing component are added to an organic solvent, and the mixture is allowed to react at a reaction temperature of 50 to 120° C., or more preferably 50 to 100° C. for about 0.5 to 15 hours.

Examples of the organic solvent include ketones such as acetone, methyl ethyl ketone, methyl isobutyl ketone, and cyclohexanone; nitriles such as acetonitrile; alkyl esters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol ether esters such as methyl cellosolve acetate, ethyl cellosolve acetate, methyl carbitol acetate, ethyl carbitol acetate, ethylene glycol ethyl ether acetate, propylene glycol methyl ether acetate, 3-methyl-3-methoxy butyl acetate, and ethyl-3-ethoxy propionate; ethers such as diethyl ether, tetrahydrofuran, and dioxane; halogenated aliphatic hydrocarbons such as methyl chloride, methylene chloride, chloroform, carbon tetrachloride, methyl bromide, methylene iodide, and dichloroethane; and aprotic polar solvents such as N-methylpyrrolidone, dimethylformamide, N,N'-dimethylacetamide, dimethyl sulfoxide, and hexamethyl phosphoramide.

Further, in the above-mentioned polymerization reaction, known urethanizing catalysts such as amines or organometallic compounds may optionally be added, and a free (unreacted) polyisocyanate may be removed from the resulting isocyanate group-terminated prepolymer by a known removal means such as distillation or extraction.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of the organometallic compound include organotin compounds such as tin acetate, tin octylate, tin oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compounds such as nickel naphthenate; organic cobalt compounds such as cobalt naphthenate; organocopper compounds such as octenate copper; organic bismuth compounds such as bismuth octylate and bismuth neodecanoate; organic zirconium compounds such as zirconium acetylacetone chelate; organic titanium compounds such as titanium acetoacetic acid chelate and bis(2-ethylhexanoic acid) titanium; and organic iron compounds such as ironacetylacetone chelate.

Examples of the urethanizing catalyst also include potassium salts such as potassium carbonate, potassium acetate, and potassium octoate.

These urethanizing catalysts may be used singly or in combination of two or more.

In the bulk polymerization and the solution polymerization, for example, the polyisocyanate component and the active hydrogen group-containing component are blended so that the equivalent ratio (NCO/active hydrogen group) of the isocyanate group in the polyisocyanate component to the active hydrogen group (hydroxyl group, mercapto group, and amino group) in the active hydrogen group-containing component is in the range of, for example, 0.75 to 1.3, or preferably 0.9 to 1.1.

Further, when the above polymerization reaction is more industrially carried out, the polyurethane resin can be produced by a known process such as one shot process and prepolymer process.

In the one shot process, for example, the polyisocyanate component and the active hydrogen group-containing component are prepared (mixed) so that the equivalent ratio (NCO/active hydrogen group) of the isocyanate group in the polyisocyanate component to the active hydrogen group (hydroxyl group, mercapto group, and amino group) in the active hydrogen group-containing component is in the range of, for example, 0.75 to 1.3, or preferably 0.9 to 1.1, and thereafter, the mixture is subjected to a curing reaction at a temperature of, for example, room temperature to 250° C., or preferably room temperature to 200° C., for example, for 5 minutes to 72 hours, or preferably for 4 to 24 hours. The curing temperature may be a constant temperature, or may be increased/decreased stepwise.

In the curing reaction, the polyisocyanate component and/or the active hydrogen group-containing component is/are preferably warmed to give a low viscosity and then mixed. Thereafter, the mixture is optionally defoamed, and then injected into a preheated mold.

After the mixture is injected into the mold and subjected to reaction, the product is released from the mold, so that a polyurethane resin formed into a desired shape can be produced. After the mold release, the polyurethane resin can optionally be aged at room temperature within about 7 days.

Alternatively, in the prepolymer process, for example, first, the isocyanate component and a part of the active hydrogen group-containing component (preferably, high-molecular-weight polyol) are allowed to react to thereby synthesize an isocyanate group-terminated prepolymer having an isocyanate group at the end of the molecule. Then, the isocyanate group-terminated prepolymer thus obtained is allowed to react with the remainder of the active hydrogen group-containing component (preferably, low-molecular-weight polyol and/or polyamine component) to conduct a curing reaction. In the prepolymer process, the remainder of the active hydrogen group-containing component is used as a chain extender.

The isocyanate group-terminated prepolymer is synthesized in the following manner. The polyisocyanate component and a part of the active hydrogen group-containing component are prepared (mixed) so that the equivalent ratio (NCO/active hydrogen compound component) of the isocyanate group in the polyisocyanate component to the active hydrogen group in the part of the active hydrogen group-containing component is in the range of, for example, 1.1 to 20, preferably 1.3 to 10, or more preferably 1.3 to 6, and the mixture is allowed to react in a reaction vessel at a temperature of, for example, room temperature to 150° C., or preferably 50 to 120° C., for example, for 0.5 to 18 hours, or preferably for 2 to 10 hours. In this reaction, the above-mentioned urethanizing catalyst may optionally be added, and after completion of the reaction, an unreacted polyisocyanate component can optionally be removed from the resultant product by a known removal means such as distillation or extraction.

Next, the isocyanate group-terminated prepolymer thus obtained and the remainder of the active hydrogen group-containing component are allowed to react in the following manner. The isocyanate group-terminated prepolymer and the remainder of the active hydrogen group-containing component are prepared (mixed) so that the equivalent ratio (NCO/active hydrogen group) of the isocyanate group in the isocyanate group-terminated prepolymer to the active hydrogen group in the remainder of the active hydrogen group-containing component is in the range of, for example, 0.75 to 1.3, or preferably 0.8 to 1.2, and the mixture is then subjected to a curing reaction at a temperature of, for example, room temperature to 250'C, or preferably room temperature to 200° C., for example, for 5 minutes to 72 hours, or preferably for 1 to 24 hours.

In the curing reaction, the isocyanate group-terminated prepolymer and/or the remainder of the active hydrogen group-containing component is/are preferably warmed to give a low viscosity and then mixed. Thereafter, the mixture is optionally defoamed and then injected into a preheated mold.

After the mixture is injected into the mold and subjected to reaction, the product is released from the mold, so that a polyurethane resin formed into a desired shape can be produced. After the mold release, the polyurethane resin can optionally be aged at room temperature within about 7 days.

When producing the polyurethane resin of the present invention as an elastomer, further, known additives such as a plasticizer, antiblocking agent, heat-resistant stabilizer, light-resistant stabilizer, ultraviolet absorber, NOx yellowing prevention agent, antioxidant, releasing agent, and catalyst; further, a pigment, dye, lubricant, filler, and hydrolysis inhibitor can optionally be blended at an appropriate ratio. These additives may be added at the time of synthesizing components, or may be added at the time of mixing and dissolving components, or may be added after the synthesis.

Examples of the light-resistant stabilizer include hindered amine compounds (to be specific, Tinuvin 765, Tinuvin 770, Tinuvin 622LD, all manufactured by BASF, to be specific, Adeka Stab LA-52, Adeka Stab LA-57, Adeka Stab LA-63P, Adeka Stab LA-68, Adeka Stab LA-72, Adeka Stab LA-82, Adeka Stab LA-87, all manufactured by ADEKA). These light-resistant stabilizers may be used singly or in combination of two or more.

Examples of the ultraviolet absorber include benzotriazole compounds (to be specific, Tinuvin 571, Tinuvin 213, Tinuvin 234, Tinuvin P (all manufactured by BASF)), and formamidine-based compounds (to be specific, Zikasorb R, Zikasorb BS, ZIKA-FA02, ZIKA-FUA, ZIKA-FUV, ZIKA-UVS3, ZLKA-UVS4 (all manufactured by ZIKO)). These ultraviolet absorbers may be used singly or in combination of two or more.

Examples of the NOx yellowing prevention agent include 1,6-hexamethylenebis(N,N-dimethyldimethyl semicarbazide), 1,1,1',1'-tetramethyl-4,4'-(methylene-di-p-phenylene) disemicarbazide, and tri-(hexamethylene-N,N-dimethyl semicarbazide). To be specific, HN-130, HN-150, and HN-300 (all manufactured by Japan Finechem Inc.) can be used. These NOx yellowing prevention agents may be used singly or in combination of two or more.

The polyurethane resin produced thus as elastomers has excellent appearance, mechanical properties (elongation, strength), and durability. Therefore, the polyurethane resin produced as elastomers can be used in various industrial fields.

For example, the thermosetting urethane elastomer (TSU) can be used for applications in members for various industrial machines, to be specific, image-forming apparatuses such as printing press, copier, printer; roll members (e.g., pressure roll, fixing roll, paper feed roll, etc.) and belt members (e.g., transmission belt, carrier belt, conveyor belt, shoe press belt, etc.) used for paper machines; pump components used for heavy machineries and marine products including oil, gas, mining, dump; clamp, seal, roller, wheel, wheel tread, caster, chute, valve, shaker, shock absorber, bushing, damper, coil, roller coaster roller, tread, wheel, and furthermore, members for applications in oil-water fracturing mud. Furthermore, the thermosetting urethane elastomer (TSU) can also be used for applications in tire chain, two-wheel, four-wheel, motorbike, bicycle, tire for motocross, spoke, tread-surrounding member; cover material and core material for golf ball; sporting members such as tennis ball, basketball, and volleyball; covers or shock absorbing material for smartphone and tablet; driving parts, supporting parts, and composite parts with metals for robot; medical components such as nursing member, cover material, industrial member, civil engineering and construction material, transparent resin alternatives such as glass or polycarbonate, applications such as spectacle lens, pick-up lens, and head lamp, soft gel, roll, sheet, film, electrical construction materials components, civil engineering and construction components, paper manufacture or industrial felt, sound insulation member, bounce stopper, sensor, switch, conductive member, vibration-proof components, hose, tube, connector seal, blanket, or rolls involved with production of paper manufacturing, iron steel, printer, copy, liquid crystal, PDP, organic EL, chemical or physical foaming urethane products, microcellular, optical sheet, film, cleaning blade, squeegee, and furthermore, cushioning material, self-recovery material, truck, floor material, Bullet train, ships, gasket for linear motor, sealing material, soles, inner and outer members for shoes, urethane disc, cushion board, torque limiter, pinch roller, press roll, electrical insulation material, wiping cloth, copy cleaner, and gasket.

The thermoplastic urethane elastomer (TPU) can be suitably used in various industrial fields including the following: tubes (e.g., in addition to components such as medical tubes and catheter, tubes such as air tubes, hydraulic tubes, and electric wire tubes, and hoses such as fire hoses), belts (e.g., bands such as watchband, for example, transmission belts for automobiles, belts such as conveyance belts for various industries (conveyor belt)), furthermore, industrial products such as gasket, cable sheath, wire harness, telecommunication cable, automobile wires, computer wires, and curl codes, nursing products such as sheets and films, sporting goods, leisure goods, miscellaneous goods, vibration-proof and seismic isolation materials, shock absorbing material, optical materials, films for light guide film, console box, automobile components such as instrument panels and door panels, surface protection sheets, decorative sheet, transfer sheets, tape members such as semiconductor protection tapes, outsole, golf ball member, strings for tennis rackets, films for agricultural use, wall paper, anti-fogging agents, yarn, fiber, nonwoven fabric, cover materials, transparent films, automobile chipping films, tire members for compact automobiles, electronic passport members, crock members, and optical material members including sunglasses, spectacle lens, and their frames.

Next, description is given for a case where a lens is produced as the polyurethane resin of the present invention.

In this case, the polyurethane resin of the present invention is produced as an optical polyurethane resin by reaction of the above-described polyisocyanate component with the above-described active hydrogen group-containing component.

The polyisocyanate component for production of an optical polyurethane resin as the polyurethane resin of the present invention include the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as an optical polyurethane resin, examples of the above-described active hydrogen group-containing component include the above-described polyol component and/or polythiol component.

For the active hydrogen group-containing component, preferably, the above-described aliphatic polythiol (aliphatic polythiol not containing a sulfur atom other than the mercapto group), and aliphatic polythiols containing a sulfur atom other than the mercapto group are used, and more preferably, pentaerythritoltetrakis(3-mercaptopropionate) and 1,2-bis(2-mercaptoethylthio)-3-propane thiol are used.

When producing the polyurethane resin of the present invention as an optical polyurethane resin, the polyol component has a hydroxyl number of, for example, 280 to 1240 mgKOH/g, preferably 400 to 940 mgKOH/g, and a number average molecular weight, and an average functionality of, for example, more than 2, preferably more than 2.5, even more preferably more than 2.8, and generally less than 5, preferably less than 4.5.

When the hydroxyl number and the average functionality are within these ranges, the impact resistance and heat resistance of the polyurethane resin produced as an optical polyurethane resin can be improved.

The polyol component has a number average molecular weight of, for example, 90 to 1000, preferably 100 to 800.

For the active hydrogen group-containing component, as necessary, for example, the above-described low molecular-weight polyol, polythiol component (excluding aliphatic polythiol), polyamine component, and monol and/or monoamine can be blended at a suitable ratio.

The polyisocyanate component can be allowed to react with the active hydrogen group-containing component in conformity with a known polyurethane molding method, such as the above-described one shot process (the one shot process used for producing the polyurethane resin of the present invention as elastomers), and the above-described prepolymer process (the prepolymer process used for producing the polyurethane resin of the present invention as elastomers).

When the one shot process is used, the polyisocyanate component and the active hydrogen group-containing component are prepared (mixed) so that the equivalent ratio (NCO/active hydrogen group) of the isocyanate group in the polyisocyanate component to the active hydrogen group (hydroxyl group, mercapto group, amino group) in the active hydrogen group-containing component is in the range of, for example, 0.5 to 2.0, preferably 0.75 to 1.25, and thereafter, the mixture is injected into a mold and subjected to a curing reaction at, for example, room temperature to 180° C., preferably room temperature to 150° C., for, for example, 10 minutes to 72 hours, preferably 4 to 24 hours.

When the prepolymer process is used, first, the polyisocyanate component and a part of the active hydrogen group-containing component are prepared (mixed) so that the equivalent ratio (NCO/active hydrogen group) of the isocyanate group in the polyisocyanate component to the active hydrogen group in the part of the active hydrogen group-containing component is in the range of, for example, 1.1 to 20, or preferably 1.5 to 10, and the mixture is allowed to react in a reaction vessel at a temperature of, for example, room temperature to 150° C., or preferably 50 to 120° C., for example, for 0.5 to 18 hours, or preferably for 2 to 10 hours, so that an isocyanate group-terminated prepolymer is produced.

Next, the isocyanate group-terminated prepolymer thus obtained and the remainder of the active hydrogen group-containing component are allowed to react in the following manner. The isocyanate group-terminated prepolymer and the remainder of the active hydrogen group-containing component are prepared (mixed) so that the equivalent ratio (NCO/active hydrogen group) of the isocyanate group in the isocyanate group-terminated prepolymer to the active hydrogen group in the remainder of the active hydrogen group-containing component is in the range of, for example, 0.5 to 2.0, or preferably 0.75 to 1.25. The mixture is then injected into a mold, and a curing reaction is conducted at a temperature of, for example, room temperature to 180° C., or preferably room temperature to 150° C., for example, for 5 minutes to 72 hours, or preferably for 1 to 24 hours.

When the polyurethane resin (optical polyurethane resin) thus obtained is used for polarizing lenses or the like, for example, insert molding can also be performed in the above-mentioned molding method, specifically, after a polarizing film or the like is preliminarily set in a mold, the mixed raw material (the polyisocyanate component and the active hydrogen group-containing component) is injected thereinto.

Also, when the polyurethane resin of the present invention is produced as an optical polyurethane resin, further, known additives such as internal release agent, blueing agent, plasticizer, antifoaming agent, leveling agent, flatting agent, fire retardant, thixotropic agent, tackifier, thickening agent, lubricant, antistatic agent, surfactant, reaction retardant, dehydrator, antioxidant, ultraviolet absorber, hydrolysis inhibitor, or weathering stabilizer can optionally be blended at an appropriate ratio.

For example, in the case of blending an internal release agent, in the above-mentioned molding method, an internal release agent preferably warmed is blended to the mixed raw material (the polyisocyanate component and the active hydrogen group-containing component), or when the mixed raw material is injected into a mold, at a ratio of, for example, 0.01 to 10 parts by mass, or preferably 0.1 to 5 parts by mass, relative to 100 parts by mass of the total amount of the polyisocyanate component and the active hydrogen group-containing component.

Examples of the internal release agent include a phosphoric ester-based release agent, alkyl phosphate-based release agent, and fatty acid ester-based release agent. Among them, a phosphoric ester-based release agent is preferable. The blending of such an internal release agent can produce a polyurethane resin capable of facilitating mold release.

The polyurethane resin thus produced as an optical polyurethane resin has an excellent appearance (transparency) and is excellent in refraction, mechanical property (tensile strength), and durability.

Accordingly, the polyurethane resin (optical polyurethane resin) satisfies a practical level of optical characteristics and is excellent in mechanical properties such as heat resistance and impact resistance, so that the polyurethane resin (optical polyurethane resin) can be suitably used for optical lenses such as transparent lenses, sunglass lenses, polarizing lenses, spectacle lens, camera lens, pick-up lens, contact lens; optical materials such as on-vehicle light panel, head light lens, head light and tail light lamp cover, optical element, optical disc, organic EL, and LED; and optical components such as illumination including signboard, optical fiber, glass alternatives, intermediate film for laminated glass, windshield for airplane, large-scale water tank wall, transparent roofing material, grazing material, transparent member for commodities, protective glasses, hoods, protective shields, automotive safety components, lighting components, smartphone, and tablet.

Next, the case of producing a film, artificial leather, synthetic leather, or the like as the polyurethane resin of the present invention will be explained.

In this case, the polyurethane resin of the present invention is produced as an aqueous polyurethane resin (an aqueous dispersion of a polyurethane resin) by reaction of the above-described polyisocyanate component with the above-described active hydrogen group-containing component.

As the method of producing the polyurethane resin of the present invention as an aqueous polyurethane resin, the above-mentioned prepolymer process (the prepolymer process used for producing the polyurethane resin of the present invention elastomers) is used.

More specifically, a polyurethane resin is produced as an aqueous polyurethane resin in the following manner. For example, first, the above-mentioned isocyanate component and the active hydrogen group-containing component are allowed to react at such a ratio that the equivalent ratio (NCO/active hydrogen group) of the isocyanate group in the isocyanate component to the active hydrogen group in the active hydrogen group-containing component exceeds 1, so that an isocyanate group-terminated prepolymer is produced.

When producing the polyurethane resin of the present invention as an aqueous polyurethane resin, examples of the polyisocyanate component include the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as an aqueous polyurethane resin, examples of the active hydrogen group-containing component include the above-described polyol component.

For the active hydrogen group-containing component, preferably, a high-molecular weight polyol, more preferably, polyester polyol, polyether polyol, and polycarbonate polyol are used.

When producing the polyurethane resin of the present invention as an aqueous polyurethane resin, the high-molecular weight polyol has a hydroxyl number of, for example, 10 to 125 mgKOH/g, and a number average molecular weight of, for example, 400 to 5000, preferably 1000 to 3000, even more preferably 1000 to 2500.

When producing the polyurethane resin as an aqueous polyurethane resin, the active hydrogen group-containing component includes active hydrogen group-containing component containing a hydrophilic group (hereinafter referred to as hydrophilic group-containing active hydrogen compound).

The hydrophilic group-containing active hydrogen compound is a compound having at least one hydrophilic group and two or more active hydrogen groups together, and examples of the hydrophilic group include an anionic group, a cationic group, and a nonionic group. Examples of the active hydrogen group include those groups that react with isocyanate groups, such as a hydroxyl group, an amino group, a carboxyl group, and an epoxy group. Examples of the hydrophilic group-containing active hydrogen compound include, to be more specific, a carboxylic acid group-containing active hydrogen compound, a sulfonic acid group-containing active hydrogen compound, a hydroxyl group-containing active hydrogen compound, a hydrophilic group-containing polybasic acid, and a polyoxyethylene group-containing active hydrogen compound.

Examples of the carboxylic acid group-containing active hydrogen compound include dihydroxylcarboxylic acids such as 2,2-dimethylolacetic acid, 2,2-dimethylollactic acid, 2,2-dimethylolpropionic acid (hereinafter referred to as DMPA), 2,2-dimethylolbutanoic acid (hereinafter referred to as DMBA), 2,2-dimethyloibutyric acid, and 2,2-dimethylolvaleric acid; and diaminocarboxylic acid such as lysine and arginine, or metal salts or ammonium salts thereof. Among them, 2,2-dimethylolpropionic acid (DMPA) and 2,2-dimethylolbutanoic acid (DMBA) are preferable.

Examples of the sulfonic acid group-containing active hydrogen compound include dihydroxybutane sulfonic acid and dihydroxypropane sulfonic acid that are obtained from synthesis reaction between an epoxy group-containing compound and acid sulfite. Examples also include N,N-bis(2-hydroxyethyl)-2-aminoethanesulfonic acid, N,N-bis(2-hydroxyethyl)-2-aminobutanesulfonic acid, 1,3-phenylenediamine-4,6-disulfonic acid, diaminobutanesulfonic acid, diaminopropane sulfonic acid, 3,6-diamino-2-toluenesulfonic acid, 2,4-diamino-5-toluenesulfonic acid, N-(2-aminoethyl)-2-aminoethanesulfonic acid, 2-aminoethanesulfonic acid, N-(2-aminoethyl)-2-aminobutanesulfonic acid, and metal salts and ammonium salts of those sulfonic acids.

Examples of the hydroxyl group-containing active hydrogen compound include N-(2-aminoethyl) ethanolamine.

Examples of the hydrophilic group-containing polybasic acid include polybasic acid containing sulfonic acid, to be more specific, 5-sulfoisophthalic acid, sulfoterephthalic acid, 4-sulfophthalic acid, 5-(p-sulfophenoxy) isophthalic acid, 5-(sulfopropoxy) isophthalic acid, 4-sulfonaphthalene-2,7-dicarboxylic acid, sulfopropylmalonic acid, sulfosuccinic acid, 2-sulfobenzoic acid, 2,3-sulfobenzoic acid, 5-sulfosalicylic acid, alkyl ester of those carboxylic acids, and also metal salts and ammonium salts of those sulfonic acids. Preferably, sodium salts of 5-sulfoisophthalic acid, or sodium salts of 5-sulfoisophthalic acid dimethyl ester are used.

The polyoxyethylene group-containing active hydrogen compound is a compound containing a polyoxyethylene group in its main chain or its side chain and having two or more active hydrogen groups.

As the polyoxyethylene group-containing active hydrogen compound, for example, polyethylene glycol (e.g., number average molecular weight 200 to 6000, preferably 300 to 3000), or a polyoxyethylene side chain-containing polyol is used.

The polyoxyethylene side chain-containing polyol contains a polyoxyethylene group in its side chain, and is a compound having two or more active hydrogen groups. The polyoxyethylene side chain-containing polyol can be synthesized in the following manner.

Specifically, first, a urethane-forming reaction is conducted by mixing a known diisocyanate and a one-end-capped polyoxyethylene glycol (e.g., alkoxy ethylene glycol of which the terminal is capped with an alkyl group of 1 to 4 carbon atoms, having a number average molecular weight of 200 to 6000, or preferably 300 to 3000) at such a ratio that the amount of the isocyanate group in the diisocyanate exceeds the amount of the hydroxyl group in the one-end-capped polyoxyethylene glycol, and, if necessary, unreacted diisocyanate is removed from the mixture, to thereby obtain a polyoxyethylene chain-containing monoisocyanate.

Then, the polyoxyethylene chain-containing monoisocyanate and dialkanolamine (e.g., diethanol amine, etc.) are subjected to urea-forming reaction at such a ratio that the isocyanate group of the polyoxyethylene group-containing monoisocyanate is substantially equal with the secondary amino group of dialkanolamine.

As the diisocyanate used to obtain a polyoxyethylene side chain-containing polyol, aliphatic diisocyanates such as pentamethylenediisocyanate, hexamethylene diisocyanate (HDI); and alicyclic diisocyanates such as 1,4- or 1,3-bis(isocyanatomethyl)cyclohexane ($H_6$XDI), 3-isocyanatomethyl-3,5,5-trimethyl cyclohexylisocyanate (also known as isophorone diisocyanate (IPDI)), 4,4'-methylene bis(cyclohexylisocyanate) ($H_{12}$MDI) and 2,5-/2,6-bis(isocyanatomethyl)norbornane (NBDI) are preferable. HDI is more preferable.

When the polyoxyethylene group-containing active hydrogen compound is blended, the content of the polyoxyethylene group in the polyurethane resin (solid content) is in the range of, for example, 0.9 to 30% by mass, preferably 2 to 20% by mass, or more preferably 2 to 10% by mass.

The concentration of the polyoxyethylene group in the polyurethane resin or the isocyanate group-terminated prepolymer can be determined, for example, by the NMR method using an internal standard substance or the like.

These hydrophilic group-containing active hydrogen compounds can be used singly or in combination of two or more. Among them, a carboxylic acid group-containing active hydrogen compound and a polyoxyethylene group-containing active hydrogen compound are preferable.

For the active hydrogen group-containing component, for example, the above-described low molecular-weight polyol, polythiol component, polyamine component, monol and/or monoamine can be blended at a suitable ratio.

The isocyanate group-terminated prepolymer is produced, for example, by allowing the above-mentioned polyisocyanate component and the above-mentioned active hydrogen group-containing component (containing the high-molecular weight polyol and the hydrophilic group-containing active hydrogen compound) to react by a known polymerization method such as the bulk polymerization (bulk polymerization performed when producing the polyurethane resin of the present invention as an elastomer) or the solution polymerization (solution polymerization performed when producing the polyurethane resin of the present invention as an elastomer).

Then, the above-mentioned components are formulated (mixed) so that the equivalent ratio (NCO/active hydrogen group) of the isocyanate group in the polyisocyanate component to the active hydrogen group in the active hydrogen group-containing component (containing the hydrophilic group-containing active hydrogen compound) is in the range of, for example, 1.1 to 2.5, preferably 1.2 to 2.3, or more preferably 1.2 to 2.0. When the equivalent ratio of the isocyanate group is within this range, the polyurethane resin can have an improved dispersion stability. Accordingly, the use of this polyurethane resin can provide a film, artificial leather, and synthetic leather having excellent appearance.

When the bulk polymerization is used, for example, while the polyisocyanate component is stirred under a nitrogen flow, the high-molecular-weight polyol and the hydrophilic group-containing active hydrogen compound are added thereto, and the mixture is allowed to react at a reaction temperature of 50 to 130° C. or preferably 50 to 80° C. for about 3 to 15 hours.

When the solution polymerization is used, the polyisocyanate component, the high-molecular-weight polyol, and the hydrophilic group-containing active hydrogen compound are added to the organic solvent, and the mixture is allowed to react at a reaction temperature of 50 to 120° C., or preferably 50 to 80° C. for about 3 to 15 hours.

In the above-mentioned polymerization reaction, when the hydrophilic group-containing active hydrogen compound is contained in a molecular chain of the high-molecular-weight polyol, the high-molecular-weight polyol and the above-mentioned polyisocyanate component are allowed to react, so that an isocyanate group-terminated prepolymer can be produced.

For example, in synthesis of the above-mentioned polyester polyol, blending of the above-mentioned hydrophilic group-containing active hydrogen compound as a low-molecular-weight polyol allows the hydrophilic group-containing active hydrogen compound to be contained in a molecular chain of the high-molecular-weight polyol.

Alternatively, for example, in synthesis of the above-mentioned polyester polyol, blending of the hydrophilic group-containing polybasic acid as a polybasic acid also allows the hydrophilic group-containing active hydrogen compound to be contained in a molecular chain of the high-molecular-weight polyol.

As a further alternative, for example, in synthesis of the polyester polyol, polyether polyol, polycarbonate polyol, and epoxy polyol obtained by ring-opening polymerization, blending of the above-mentioned hydrophilic group-containing active hydrogen compound as an initiator or a copolymerization component also allows the hydrophilic group-containing active hydrogen compound to be contained in a molecular chain of the high-molecular-weight polyol.

As an even further alternative, for example, a reaction between the hydrophilic group-containing active hydrogen compound and the high-molecular-weight polyol such as a polyether polyol (preferably, polytetramethylene ether glycol) also allows the hydrophilic group-containing active hydrogen compound to be contained in a molecular chain of the high-molecular-weight polyol.

When an anionic group or a cationic group is contained as the hydrophilic group in the isocyanate group-terminated prepolymer thus obtained, a neutralizing agent is preferably added thereto to form a salt of the anionic group or the cationic group.

When, for example, an anionic group is contained, examples of the neutralizing agent include conventional bases such as organic bases [e.g., tertiary amines (tri C1-4 alkylamines such as trimethylamine and triethylamine; alkanolamines such as dimethylethanolamine, methyldiethanolamine, triethanolamine, and tri-isopropanolamine; and heterocyclic amines such as morpholine)], and inorganic bases [ammonia, alkali metal hydroxide (such as lithium hydroxide, sodium hydroxide, and potassium hydroxide), alkali earth metal hydroxide (such as magnesium hydroxide and calcium hydroxide), and alkali metal carbonate (such as sodium carbonate and potassium carbonate)]. These bases can be used singly or in combination of two or more.

The neutralizing agent is added at a ratio of, for example, 0.4 to 1.2 equivalents, or preferably 0.6 to 1 equivalent, per 1 equivalent of the anionic group.

The isocyanate group-terminated prepolymer thus obtained is a polyurethane prepolymer having two or more free isocyanate groups at the end of the molecule, and the content of the isocyanate group (isocyanate group content) is in the range of, for example, 0.3 to 10% by mass, preferably 0.5 to 6% by mass, or more preferably 1.0 to 5.0% by mass. An average functionality of the isocyanate group is for example, 1.5 to 3.0, or preferably 1.9 to 2.5, and a number average molecular weight (number average molecular weight determined by GPC using a calibration curve of standard polystyrene) of the isocyanate group-terminated prepolymer is for example, 1000 to 30000, or preferably 1500 to 20000. Further, a hydrophilic group concentration of the isocyanate group-terminated prepolymer is for example, 0.1 to 1.0 mmol/g, preferably 0.2 to 0.7 mmol/g, or more preferably 0.2 to 0.6 mmol/g.

To produce the polyurethane resin of the present invention as an aqueous polyurethane resin, the isocyanate group-terminated prepolymer obtained above and a chain extender are subsequently allowed to react in water to disperse them. This can produce a polyurethane resin having the isocyanate group-terminated prepolymer chain-extended by the chain extender, as an aqueous polyurethane resin.

Examples of the chain extender include low-molecular-weight polyols such as the above-mentioned dihydric alcohols and the above-mentioned trihydric alcohols; and polyamine components such as the above-mentioned alicyclic polyamines and the above-mentioned aliphatic polyamines.

Further, examples of the chain extender include active hydrogen group-containing component containing an alkoxysilyl group. The active hydrogen group-containing component containing an alkoxysilyl group is a compound having both an alkoxysilyl group and an active hydrogen group.

In the alkoxysilyl group, examples of the alkoxy group to be bonded with a Si atom include alkoxy groups of 1 to 4 carbon atoms, such as a methoxy group, an ethoxy group, a propoxy group, a butoxy group, an isopropoxy group, and an isobutoxy group. Among them, a methoxy group and an ethoxy group are preferable. The number of the above alkoxy group bonded to the Si atom is usually 1 to 3, or preferably 1 to 2.

Examples of the active hydrogen group include a hydroxyl group, a mercapto group, and an amino group. Among them, an amino group is preferable.

More specifically, examples of the active hydrogen group-containing component containing an alkoxysilyl group include N-β(aminoethyl)-γ-aminopropylmethyl dimethoxysilane, N-β(aminoethyl)-γ-aminopropyl trimethoxysilane, γ-(2-aminoethyl)aminopropyl triethoxysilane, γ-(2-aminoethyl)aminopropyl dimethoxysilane, γ-(2-aminoethyl) aminopropyl diethoxysilane, γ-aminopropyl trimethoxysilane, γ-aminopropyl triethoxysilane, γ-aminopropyl dimethoxysilane, γ-aminopropyl diethoxysilane and N,N'-bis[(a-(trimethoxysilyl)propyl)]ethylenediamine.

The equivalent of the active hydrogen group contained in the chain extender is preferably 250 to 800 mg KOH/g, or more preferably 350 to 600 mg KOH/g. When the equivalent of the active hydrogen group is within this range, a polyurethane resin (aqueous polyurethane resin) having excellent durability can be produced.

These chain extenders may be used singly or in combination of two or more.

For the production of the polyurethane resin of the present invention as an aqueous polyurethane resin, the isocyanate group-terminated prepolymer obtained above and the chain extender are allowed to react in water to disperse them. This can produce a polyurethane resin having the isocyanate group-terminated prepolymer chain-extended by the chain extender, as an aqueous dispersion (an aqueous dispersion of a polyurethane resin).

To cause the isocyanate group-terminated prepolymer to react with the chain extender in water, for example, first, the isocyanate group-terminated prepolymer is added to water, thereby dispersing the isocyanate group-terminated prepolymer. Thereafter, a chain extender is added thereto, thereby causing chains of the isocyanate group-terminated prepolymer to extend.

The isocyanate group-terminated prepolymer is dispersed by gradually adding the isocyanate group-terminated prepolymer to water under stirring. The water is added at a ratio of preferably 60 to 1000 parts by mass relative to 100 parts by mass of the isocyanate group-terminated prepolymer.

Then, the chain extender is added to the isocyanate group-terminated prepolymer thus dispersed in water under stirring so that the equivalent ratio (active hydrogen group/NCO) of the active hydrogen group in the chain extender to the isocyanate group in the isocyanate group-terminated prepolymer is substantially equal, for example, in the range of 0.5 to 1.1, or preferably 0.7 to 1.

In the case of using a polyamine component (diamine) as the chain extender, the amino group thereof has high reactivity with the isocyanate group of the isocyanate group-terminated prepolymer and a urea bond formed by the reaction has an extremely high intermolecular cohesive force, so that it is necessary to minimize localized reaction between the chain extender and the isocyanate monomer. Therefore, the chain extender is preferably blended as an aqueous solution. The concentration of the diamine in the aqueous solution is preferably at least 20% by mass, or more preferably at least 50% by mass. The chain extender is added preferably at a temperature of 40° C. or less, and after completion of the addition, the mixture is further stirred to complete the reaction at room temperature, for example.

When the isocyanate group-terminated prepolymer is produced by solution polymerization, after completion of the reaction of the isocyanate group-terminated prepolymer, the organic solvent is removed, for example, by heating the organic solvent at an appropriate temperature under reduced pressure.

When the hydrophilic group-containing active hydrogen compound is not used as an active hydrogen group-containing component, that is, when the polyurethane resin is not internally emulsified during the production thereof as an aqueous polyurethane resin, for example, external emulsification (phase inversion emulsification or forced emulsification) is performed using an external emulsifier, for example, a nonionic surfactant such as polyoxyethylene alkyl ether, or an anionic surfactant such as sodium polyoxyethylene alkyl ether sulfate, whereby an external emulsification type aqueous polyurethane resin (an aqueous dispersion of polyurethane resin) can be produced.

The aqueous polyurethane resin (the aqueous dispersion of polyurethane resin) thus obtained is prepared so as to have a solid content of, for example, 20 to 50% by mass.

The polyurethane resin has a number average molecular weight (number average molecular weight determined by GPC using a calibration curve of standard polystyrene) of, for example, 3000 to 100000, or preferably 5000 to 80000. As for the aqueous polyurethane resin (solid content), the charged ratio of the urethane group to the urea group is in the range of, for example, preferably 0.05 to 1.2, or more preferably 0.1 to 0.8.

Also, when the polyurethane resin of the present invention is produced as an aqueous polyurethane resin, further, known additives such as a plasticizer, antiblocking agent, heat-resistant stabilizer, light-resistant stabilizer, antioxidant, releasing agent, and catalyst; or further, a pigment, dye, lubricant, filler, and hydrolysis inhibitor can optionally be blended at an appropriate ratio.

When the polyurethane resin of the present invention produced as the aqueous polyurethane resin is formed into a film, the film excellent in appearance, mechanical properties (elongation, strength), and durability can be produced.

Therefore, the film can be suitably used for artificial or synthetic leather which takes advantage of the above-mentioned properties.

The film can be formed by applying the aqueous polyurethane resin onto a substrate by a known coating such as gravure coating, reverse coating, roll coating, bar coating, spray coating, air knife coating, and dipping, and thereafter, heating the coated substrate to dry.

When used in the production of artificial and synthetic leather, the polyurethane resin of the present invention can be used, for example, as a material for a wet process or a dry process.

The aqueous polyurethane resin is not limited to the film, and the artificial or synthetic leather as mentioned above, and can be used for various applications such as automobile, electronics, clothing, medical materials, building materials, paints, and adhesives.

When a film, artificial leather, and synthetic leather are produced, in addition to production of the polyurethane resin as the above-described aqueous polyurethane resin (water dispersion of polyurethane resin), for example, the polyurethane resin can be produced as a polyurethane resin solution (organic solvent solution of polyurethane resin).

When producing the polyurethane resin of the present invention as a polyurethane resin solution, the polyisocyanate component includes the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as a polyurethane resin solution, examples of the active hydrogen group-containing component include the above-described polyol component.

For the active hydrogen group-containing component, preferably, a high-molecular weight polyol, more preferably, polyester polyol, polyether polyol, and polycarbonate polyol are used.

When producing the polyurethane resin of the present invention as a polyurethane resin solution, the high-molecular weight polyol has a hydroxyl number of, for example, 10 to 125 mgKOH/g, and a number average molecular weight of, for example, 400 to 5000, preferably 1000 to 3000, even more preferably 1000 to 2500.

When producing the polyurethane resin of the present invention as a polyurethane resin solution, the above-described prepolymer process (the prepolymer process used for producing the polyurethane resin of the present invention as elastomers) and one shot process are used.

To be more specific, a polyurethane resin is produced as a polyurethane resin solution by the prepolymer process in the following manner. For example, first, the above-described isocyanate component and the active hydrogen group-containing component are allowed to react at such a ratio that the equivalent ratio (NCO/active hydrogen group) of the isocyanate group in the isocyanate component to the active hydrogen group in the active hydrogen group-containing component exceeds 1, so that an isocyanate group-terminated prepolymer is produced.

The isocyanate group-terminated prepolymer is produced, for example, by allowing the above-mentioned polyisocyanate component and the above-mentioned active hydrogen group-containing component to react by a known polymerization method such as the bulk polymerization (bulk polymerization performed when producing the polyurethane resin of the present invention as an elastomer) or the solution polymerization (solution polymerization performed when producing the polyurethane resin of the present invention as an elastomer).

Then, the above-mentioned components are formulated (mixed) so that the equivalent ratio (NCO/active hydrogen group) of the isocyanate group in the polyisocyanate component to the active hydrogen group in the active hydrogen group-containing component is in the range of, for example, 1.1 to 5, preferably 1.2 to 3, even more preferably 1.2 to 2.5.

When the equivalent ratio of the isocyanate group is within this range, the polyurethane resin can have an improved dissolution stability. Accordingly, the use of this polyurethane resin can provide a film, artificial leather, and synthetic leather having excellent appearance.

When the bulk polymerization is used, for example, while the polyisocyanate component is stirred under a nitrogen flow, the high-molecular-weight polyol is added thereto, and the mixture is allowed to react at a reaction temperature of 50 to 130° C., or preferably 50 to 80° C. for about 3 to 15 hours.

When the solution polymerization is used, the polyisocyanate component, and the high-molecular-weight polyol are added to the organic solvent, and the mixture is allowed to react at a reaction temperature of 50 to 120° C., or preferably 50 to 80° C. for about 3 to 15 hours.

The isocyanate group-terminated prepolymer thus obtained is a polyurethane prepolymer having two or more free isocyanate groups at the end of the molecule, and the content of the isocyanate group (isocyanate group content) is in the range of, for example, 0.3 to 10 mass %. An average functionality of the isocyanate group is, for example, 1.5 to 3, preferably 1.9 to 2.5, and a number average molecular weight (number average molecular weight determined by GPC using a calibration curve of standard polystyrene) of the isocyanate group-terminated prepolymer is for example, 1000 to 30000, preferably 1500 to 20000.

When producing the polyurethane resin of the present invention as a polyurethane resin solution, then, the isocyanate group-terminated prepolymer produced as described above is allowed to react with a chain extender in an organic solvent.

Examples of the chain extender include low molecular-weight polyols such as the above-described dihydric alcohol and trihydric alcohol, and the above-described polyamine.

To allow the isocyanate group-terminated prepolymer to react with the chain extender in an organic solvent, for example, when the isocyanate group-terminated prepolymer is produced by bulk polymerization, first, the isocyanate group-terminated prepolymer is added to the above-described organic solvent (organic solvent used in the solution polymerization) to dissolve the isocyanate group-terminated prepolymer.

The isocyanate group-terminated prepolymer is dissolved by gradually adding the isocyanate group-terminated prepolymer to the organic solvent under stirring. The water is added at a ratio of preferably 60 to 1000 parts by mass relative to 100 parts by mass of the isocyanate group-terminated prepolymer.

When producing the isocyanate group-terminated prepolymer by solution polymerization, the produced isocyanate group-terminated prepolymer is dissolved in the above-described organic solvent. As necessary, an organic solvent can be further blended, or the organic solvent is removed from the isocyanate group-terminated prepolymer and then thereafter, the isocyanate group-terminated prepolymer can be dissolved in an organic solvent again.

Then, a chain extender is added to the produced isocyanate group-terminated prepolymer solution to subject the isocyanate group-terminated prepolymer to chain extension.

To be specific, a chain extender is added to the isocyanate group-terminated prepolymer dissolved in the organic solvent under stirring so that the equivalent ratio (active hydrogen group/NCO) of the active hydrogen group in the chain extender to the isocyanate group in the isocyanate group-terminated prepolymer is substantially equal, for example, 0.5 to 1.1, preferably 0.7 to 1.

This can produce a polyurethane resin having the isocyanate group-terminated prepolymer chain-extended by the chain extender, as a polyurethane resin solution.

In prepolymer-forming reaction and chain extension reaction, the above-described urethanizing catalyst can be used. In this case, the urethanizing catalyst can be used by dissolving the urethanizing catalyst in the above-described organic solvent.

To carry out the production by one shot process, for example, first, the above-described isocyanate component and the active hydrogen group-containing component are allowed to react with an equivalent ratio (NCO/active hydrogen group) of the isocyanate group in the isocyanate component to the active hydrogen group in the active hydrogen group-containing component of 0.8 to 1.2, preferably 0.9 to 1.1 to produce a polyurethane resin. The polyurethane resin is dissolved in the above-described organic solvent so that a polyurethane resin solution can be produced. Furthermore, the above-described isocyanate component can be allowed to react with the active hydrogen group-containing component at the above-described equivalent ratio directly in the above-described organic solvent to produce a polyurethane resin solution.

When the production is carried out by one shot process, the above-described urethanizing catalyst can be used. In this case, the urethanizing catalyst can be used by dissolving the urethanizing catalyst in the above-described organic solvent.

The thus produced polyurethane resin solution is prepared so that the polyurethane resin solution has a solid content of, for example, 20 to 50 mass %.

The polyurethane resin has a number average molecular weight (number average molecular weight determined by GPC using a calibration curve of standard polystyrene) of, for example, 3000 to 100000, or preferably 5000 to 80000. As for the polyurethane resin (solid content), the charged ratio of the urethane group to the urea group is in the range of, for example, 0.05 to 1.2, or more preferably 0.1 to 0.8.

When producing the polyurethane resin of the present invention as a polyurethane resin solution as well, as necessary, known additives such as a plasticizer, anti-blocking agent, heat-resistant stabilizer, light-resistant stabilizer, antioxidant, releasing agent, catalyst, and also a pigment, dye, lubricant, filler, and hydrolysis inhibitor can be further blended at a suitable ratio.

When the polyurethane resin of the present invention produced as the polyurethane resin solution is formed into a film as is the case with the above-described aqueous polyurethane resin, the film excellent in appearance, mechanical properties (elongation, strength), and durability can be produced.

Therefore, the film can be suitably used for artificial or synthetic leather which takes advantage of the above-mentioned properties.

The polyurethane resin solution can also be used, in addition to the above-described film, artificial leather, and synthetic leather, for example, in various applications including, for example, a laminate of polyurethane resin and polyethylene terephthalate (PET) cloth, composite sheet, nonwoven fabric, automobile, electronics, clothing, medical materials, building materials, paints, and adhesives.

Next, the case of using the polyurethane resin of the present invention as a paint (coating composition) and an adhesive (adhesive composition) will be explained.

When the polyurethane resin of the present invention is used as a paint and an adhesive, the polyurethane resin of the present invention is prepared as a two-part curing polyurethane resin obtained by separately preparing the above-mentioned polyisocyanate component and the above-mentioned active hydrogen group-containing component, and blending them when used.

When producing the polyurethane resin of the present invention as a two-part curing polyurethane resin, for the above-described polyisocyanate component, for example, the above-described polyisocyanate composition (derivative of 1,4-bis(isocyanatomethyl)cyclohexane) is used singly.

To be more specific, for the above-described polyisocyanate component, a polyol modified 1,4-bis(isocyanatomethyl)cyclohexane described above is used singly.

When producing the polyurethane resin of the present invention as a two-part curing polyurethane resin, examples of the above-described active hydrogen group-containing component include the above-described polyol component, and preferably, a high-molecular weight polyol, and as a coating composition, preferably, acrylic polyol is used.

For the active hydrogen group-containing component, as necessary, furthermore, for example, the above-described low molecular-weight polyol, polythiol component, polyamine component, monol and/or monoamine can be blended at a suitable ratio.

The two-part curing polyurethane resin is preferably used as a two-part curing type paint and/or a two-part curing type adhesive agent. Specifically, first, the above-mentioned active hydrogen group-containing component is prepared, and a polyisocyanate component is then separately prepared. The active hydrogen group-containing component and the polyisocyanate component are mixed immediately before use, to prepare a two-part curing polyurethane resin, and the two-part curing polyurethane resin is applied onto an article to be coated or adhered.

In addition to the above components, the two-part curing polyurethane resin can also contain other functional compounding agents according to the purpose and application.

As the functional compounding agent, for example, CAB (cellulose acetate butyrate), NC (nitrocellulose) or the like may be contained in order to improve the drying property of the coating film, or a polymer polymerized from an acrylic acid or ester, or polyester can be contained in order to improve the gloss and the hardness of the coating film, and the application performance of the paint.

When producing the polyurethane resin of the present invention as a two-part curing polyurethane resin, further, a known additive, such as color pigment, dye, ultraviolet absorber, curing accelerator, light stabilizer, and flatting agent, as a coating composition; or an oxyacid of phosphorus or its derivative, and a silane coupling agent for improvement in adhesion for coatings as an adhesive composition can optionally be blended at an appropriate ratio.

Examples of the color pigment and dye include inorganic pigments such as carbon black and titanium oxide with good weather resistance; and organic pigments and dyes such as phthalocyanine blue, phthalocyanine green, quinacridone red, indanthrene orange, and isoindolinone yellow.

Examples of the ultraviolet absorber include ultraviolet absorbers of benzophenone type, benzotriazol type, triazine type, and cyanoacrylate type.

Examples of the curing accelerator include dibutyltin dilaurate.

Examples of the light stabilizer include a hindered amine light stabilizer, and more specifically, Adeka Stab LA62, Adeka Stab LA67 (trade names, all manufactured by Adeka Argus Chemical Co., Ltd.), Tinuvin 292, Tinuvin 144, Tinuvin 123, and Tinuvin 440 (trade names, all manufactured by BASF).

Examples of the flatting agent include superfine synthetic silica. When the flatting agent is blended, an elegant coating film having a semi-gloss and flat finish can be formed.

As for the oxyacid of phosphorus or its derivative, examples of the oxyacid of phosphorus include phosphoric acids such as phosphinic acid, phosphorous acid, orthophosphoric acid, and hypophosphoric acid; and condensed phosphoric acids such as metaphosphoric acid, pyrophosphoric acid, tripoliphosphoric acid, polyphosphoric acid, and ultraphosphoric acid.

Examples of the derivative thereof include salts such as sodium salts and potassium salts, of phosphoric acids or condensed phosphoric acids; monoesters such as monomethyl orthophosphate, monoethyl orthophosphate, monopropyl orthophosphate, monobutyl orthophosphate, mono-2-ethylhexyl orthophosphate, monophenyl orthophosphorate, monomethyl phosphite, monoethyl phosphite, monopropyl phosphite, monobutyl phosphite, mono-2-ethylhexyl phosphite, and monophenyl phosphite; di- and triesters such as di-2-ethylhexyl orthophosphate, diphenyl orthophosphate, trimethyl orthophosphate, triethyl orthophosphate, tripropyl orthophosphorate, tributyl orthophosphate, tri-2-ethylhexyl orthophosphate, triphenyl orthophosphate, dimethyl phosphite, diethyl phosphite, dipropyl phosphite, dibutyl phosphite, di-2-ethylhexyl phosphite, diphenyl phosphite, trimethyl phosphite, triethyl phosphite, tripropyl phosphite, tributyl phosphite, tri-2-ethylhexyl phosphite, and triphenyl phosphite; or mono-, di- and triesters obtained from condensed phosphoric acids and alcohols.

As for the oxyacid of phosphorus or its derivative, the above-mentioned various oxyacids of phosphorus or their derivatives can be used singly or in combination of two or more. The oxyacid of phosphorus or its derivative is blended in a proportion of 0.001 to 3 parts by mass, or preferably 0.01 to 2.5 parts by mass, to 100 parts by mass of the total of the polyisocyanate component and the active hydrogen group-containing component.

The silane coupling agent is represented by, for example, structural formula of R—Si≡(X)$_3$ or R—Si≡(R') (X)$_2$, (wherein R represents an organic group having a vinyl, epoxy, amino, imino, isocyanate, or mercapto group; R' represents a lower alkyl group having 1 to 4 carbon atoms; and X represents a methoxy or ethoxy group, or chlorine atom).

Specific examples of the silane coupling agent include chlorosilanes such as vinyltrichlorosilane; epoxysilanes such as γ-glycidoxypropyltrimetoxysilane, γ-glycidoxypropyltriethoxysilane, β-(3,4-epoxycyclohexyl)ethyltrimethoxysilane, and di(γ-glycidoxypropyl)dimethoxysilane; aminosilanes such as N-β-(aminoethyl)-γ-aminopropyltrimethoxysilane, γ-aminopropyltriethoxysilane, N-β-(aminoethyl)-γ-propylmethyl dimethoxysilane, N-(dimethoxymethylsilylpropyl)ethylenediamine, n-(triethoxysilylpropyl)ethylenediamine, and N-phenyl-γ-aminopropyltrimethoxysilane; vinyl silanes such as vinyltriethoxysilane; and isocyanato silanes such as γ-isocyanatopropyltrimethoxysilane and γ-isocyanatopropyltriethoxysilane.

As for the silane coupling agent, the above-mentioned various silane coupling agents can be used singly or in combination of two or more. The silane coupling agent is blended in a proportion of 0.001 to 10 parts by mass, or preferably 0.01 to 5 parts by mass, to 100 parts by mass of the total of the polyisocyanate component and the active hydrogen group-containing component.

These functional compounding agents and additives may be preliminarily blended with the polyisocyanate component and/or the active hydrogen group-containing component, or can also be blended with the two-part curing polyurethane resin after blending of the polyisocyanate component and the active hydrogen group-containing component.

When producing the polyurethane resin of the present invention as a two-part curing polyurethane resin, the polyisocyanate component and the active hydrogen group-containing component are blended at the time of use, to prepare a two-part curing polyurethane resin, and the two-part curing polyurethane resin is applied to an article to be coated or adhered.

The polyisocyanate component and the active hydrogen group-containing component are blended at such a ratio that the equivalent ratio (NCO/active hydrogen group) of the isocyanate group in the polyisocyanate component to the active hydrogen group in the active hydrogen group-containing component is, for example, 0.5 to 3, preferably 0.5 to 1.5, more preferably 0.8 to 1.2.

The polyurethane resin of the present invention thus produced as the two-part curing polyurethane resin can be dried and cured in a short drying time, and is excellent in coating and adhering properties such as coating hardness and tensile strength, and further having excellent durability.

The two-part curing polyurethane resin can be coated over the article to be coated or adhered by any coating method such as spray coating, air spray coating, brush coating, dip coating, a roll coater method, and a flow coater method, without particular limitation.

The article to be coated is not particularly limited, and examples thereof include inorganic substances such as concrete, natural stone, and glass; metals such as iron, stainless steel, aluminum, copper, brass, and titanium; and organic substances such as plastic including polycarbonate, polyamide, ABS (acrylonitrile-butadiene-styrene copolymer), polypropylene, polyethylene, polylactic acid resin, rubber, adhesive, and wood. In particular, the two-part curing polyurethane resin is suitable for re-coating of surfaces of already-formed coating films. It is also suitable for coating of a fiber reinforcement plastic (FRP) which is an organic/inorganic composite, a concrete polymer composite, a fiber-reinforced concrete, or the like.

The article to be adhered is not particularly limited, and examples thereof include various building materials and various laminated films.

More specifically, the two-part curing polyurethane resin is suitable for transportation equipments such as an automobile, an electric train, an airplane; civil engineering components such as a bridge component and a steel tower; industrial equipments such as a water-proof sheet, a tank, and a pipe; building components such as an exterior of a building, a door, a window material, a monument, and a pole; road components such as a center divider, a guardrail, and a sound insulating wall; communication equipments such as mobile phone, smartphone, and tablet; back sheet of solar battery; or electric or electronic components.

Next, the case of producing the polyurethane resin of the present invention in the form of a polyurethane foam will be explained.

The polyurethane resin of the present invention produced in the form of a polyurethane foam is produced from a raw material containing the polyisocyanate component, the active hydrogen group-containing component, a foaming agent, and an urethanizing catalyst.

When producing the polyurethane resin of the present invention as a polyurethane foam, examples of the polyisocyanate component include the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as a polyurethane foam, examples of the above-described active hydrogen group-containing component include the above-described polyol component.

For the active hydrogen group-containing component, preferably, the above-described high-molecular weight polyol, more preferably, polyether polyol is used.

When producing the polyurethane resin of the present invention as a polyurethane foam, the high-molecular weight polyol has a hydroxyl number of, for example, 10 to 120 mgKOH/g, preferably 20 to 10 mgKOH/g, more preferably 20 to 80 mgKOH/g, and a number average molecular weight of, for example, 400 to 20000.

When the hydroxyl number is within the above range, the polyurethane foam can achieve an improved impact resilience and a low permanent compression set.

The high-molecular-weight polyol has an average functionality of preferably about 2 to 6 from the view point of improvement in mechanical properties.

Further, the high-molecular-weight polyol is prepared preferably in liquid state at room temperature in order to improve the mixing properties with the polyisocyanate component.

For the active hydrogen group-containing component, as necessary, furthermore, for example, the above-described low molecular-weight polyol, polythiol component, polyamine component, monol and/or monoamine can be blended at a suitable ratio. When the low molecular-weight polyol and the polyamine component are used in combination for the active hydrogen group-containing component, the low molecular-weight polyol and/or polyamine component are blended as a cross-linking agent for improvement in impact resilience of the polyurethane foam.

The crosslinking agents can be used singly or in combination of two or more. The amount of the crosslinking agent blended is in the range of, for example, 0.5 to 10 parts by mass, or preferably 1 to 7 parts by mass, relative to 100 parts by mass of the high-molecular-weight polyol.

As the foaming agent, for example, a chemical foaming agent and a physical foaming agent may be used. Examples of the chemical foaming agent include water, which generates carbon dioxide by reaction with a polyisocyanate component. The amount of the chemical foaming agent is in the range of, for example, 0.1 to 6 parts by mass, preferably 0.5 to 5 parts by mass, or more preferably 0.5 to 4 parts by mass, relative to 100 parts by mass of the high-molecular-weight polyol.

Examples of the physical foaming agent include methylene chlorides, chlorofluorocarbons, hydroxy chlorofluorocarbons (HCFC-134a etc.), hydrocarbons (cyclopentane, etc.), carbon dioxide, liquefied carbon dioxide, supercritical (carbon dioxide) gas, HFCs (hydrofluorocarbons), organic foaming agents (organic foaming agents having a decomposition temperature of 60 to 130° C., including for example, azo compounds such as diazoaminobenzene, ethyl diazoacetate, diazoacetic acidamide, and azodicarbonamide; and sulfonylhydrazide compounds such as benzene sulphonyl hydrazide and p-toluene sulfonyl hydrazide), and inorganic foaming agents (inorganic foaming agents having a decomposition temperature of 60 to 130° C., including, for example, ammonium carbonate, ammonium hydrogencarbonate, sodium hydrogencarbonate, phosphorous acid ammonium, etc.).

These physical foaming agents can be used singly or in combination of two or more. The amount of the physical foaming agent is in the range of, for example, 0.1 to 4 parts by mass, or preferably 0.1 to 3 parts by mass, relative to 100 parts by mass of the high-molecular-weight polyol.

The density of the polyurethane foam can be controlled according to the blending amount of the foaming agent.

As the urethanizing catalyst, the above-mentioned known urethanizing catalysts may be used. Preferably, amines and potassium salts are used in combination. The amount of the urethanizing catalyst is in the range of, for example, 0.01 to 3 parts by mass, or preferably 0.02 to 1.5 parts by mass, relative to 100 parts by mass of the high-molecular-weight polyol.

When producing the polyurethane resin of the present invention in the form of a polyurethane foam, as a raw material, a foam stabilizer or other additives can further optionally be blended at an appropriate ratio.

Examples of the foam stabilizer include silicone-based foam stabilizers such as a siloxane-oxyalkylene block copolymer. Specific examples thereof include products manufactured by MOMENTIVE, trade names: L-580, L-590, L-620, L-680, L-682, L-690, SC-154, SC-155, SC-240, L-598, L-2100, L-2171, SH-210, L-2114, SE-232, L-533, L-534, L-539, M-6682B, L-626, L-627, L-3001, L-3111, L-3415, L-3002, L-3010, L-3222, L-3416, L-3003, L-3333, L-3417, L-2171, L-3620, L-3630, L-3640, L-3170, L-3360, L-3350, L-3555, L-3167, L-3150, L-3151, L-5309, SH-209, and L-3184.

Further examples thereof include products manufactured by Dow Corning Toray Co., Ltd., trade names: SF-2964, SF-2962, SF-2969, SF-2971, SF-2902L, SF-2904, SF-2908, SF-2909, SRX-274C, SZ-1328, SZ-1329, SZ-1330, SZ-1336, SZ-1346, SZ-3601, SRX-294A, SRX-280A, SRX-298, SH-190, SH-192, and SH-194.

Further, examples thereof include products manufactured by Shin-Etsu Chemical Co., Ltd., trade names: F-327, F-345, F-305, and F-242T; and products manufactured by BYK Chemie, trade names: Silbyk 9700, Silbyk 9705, and Silbyk 9710.

These foam stabilizers can be used singly or in combination of two or more. The amount of the foam stabilizer is in the range of, for example, 0.1 to 3 parts by mass, or preferably 0.2 to 1.5 parts by mass, relative to 100 parts by mass of the high-molecular-weight polyol.

Examples of other additives include heat-resistant stabilizer (antioxidant), light-resistant stabilizer, and multifunctional stabilizer.

Examples of the heat-resistant stabilizer include stabilizers such as a hindered phenol type stabilizer, an amine type stabilizer, a phosphorus type stabilizer, and a sulfur stabilizer.

Examples of the light-resistant stabilizer include a benzophenone type ultraviolet absorber, a benzotriazol type ultraviolet absorber, a hindered amine type ultraviolet absorber, a salicylate type ultraviolet absorber, a cyanoacrylate type ultraviolet absorber, an acrylonitrile type ultraviolet absorber, a nickel or cobalt complex type ultraviolet absorber. Among them, a benzophenone type ultraviolet absorber and a benzotriazol type ultraviolet absorber are preferable.

The multifunctional stabilizer is a stabilizer, for example, having both an ultraviolet absorption function and an antioxidant function, and specific examples thereof include a benzotriazolyl-alkyl bisphenol compound.

When producing the polyurethane resin of the present invention in the form of a polyurethane foam, the method for producing a polyurethane foam is not particularly limited, and a known foaming method can be used.

For example, as a raw material, components (i.e., an active hydrogen group-containing component, a foaming agent and an urethanizing catalyst as essential components, and a crosslinking agent, a foam stabilizer, and an additive as optional components) other than the polyisocyanate component are preliminarily blended to prepare a resin premix. Subsequently, the polyisocyanate component and the resin premix are blended to perform foam molding, Known methods such as a slab foaming process and a mold foaming process may be used for foam molding.

Alternatively, the above-mentioned various components (i.e., an active hydrogen group-containing component, a foaming agent and an urethanizing catalyst as essential components, and a crosslinking agent, a foam stabilizer, and an additive as optional components) can be blended, for example, with the resin premix not preliminarily but immediately before foaming.

As the blending proportion of the polyisocyanate component and the resin premix, the index (INDEX), which is represented by the molar ratio of the isocyanate group in the polyisocyanate component to the active hydrogen group in the active hydrogen group-containing component in terms of percentage, is in the range of, for example, 70 to 180, preferably 80 to 150, or more preferably 85 to 130.

In the above-mentioned production, a mechanical froth foaming process can also be used. The mechanical froth foaming process is performed in the following manner. First, air is blown into the resin premix to whip, and uniform microbubbles are formed in the resin premix (air loading). Subsequently, polyisocyanate is mixed therein and reacted to be cured at a temperature of 60 to 130° C.

The slab foaming process produces molded articles, for example, for clothing, sanitary, or the like. Specifically, first, the polyurethane foam is molded by a slab foaming process and thereafter, cut into a predetermined size. Then, the cut molded foam is placed in a mold and thermoformed so as to have an intended shape, to thereby produce a molded article. As the thermoforming conditions, for example, the foam is heated at a temperature of 180 to 220° C. for several dozen seconds to several minutes.

On the other hand, the mold foaming process produces molded articles for shoes, body pressure distribution, or the like. Specifically, first, a reaction solution mixed with a resin premix and a polyisocyanate component is injected into a desired shaped mold in which the temperature is preliminarily adjusted to, for example, 40 to 70° C. Subsequently, the reaction solution is foamed in the mold to produce a polyurethane foam. Then, an intended molded article is produced through the subsequent steps such as coating and adhesion.

As a result of the above process, the polyurethane resin of the present invention can be produced as, for example, a flexible, semirigid, rigid, or microcellular polyurethane foam (having a density of, for example, 10 to 200 kg/m$^3$, preferably 20 to 80 kg/m, or more preferably 25 to 70 kg/m$^3$).

The polyurethane resin of the present invention produced as a polyurethane foam has a high density, low contractibility, and excellent permeability. Furthermore, the polyurethane resin of the present invention produced as a polyurethane foam has excellent mechanical properties (hardness, elongation, strength, etc.), and durability.

Therefore, the polyurethane resin of the present invention thus produced in the form of a polyurethane foam can be used in wide applications such as furniture articles such as mattress and sofas; chairs; clothing articles such as brassieres, underwear, and shoulder pads; cosmetic tools such as puffs; shoes articles such as soles; further, speaker; cushioning material, body pressure distribution articles such as pads and cushions for vehicles; heat resisting materials for electric refrigerators or buildings; fillers, and vehicles articles such as vehicle handles; and members for robot.

Next, the case of producing slush powders as the polyurethane resin of the present invention will be explained.

In this case, the polyurethane resin of the present invention is produced as a granular polyurethane resin by reaction of the above-described polyisocyanate component with the above-described active hydrogen group-containing component.

When producing the polyurethane resin of the present invention as a granular polyurethane resin, examples of the polyisocyanate component include the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as a granular polyurethane resin, examples of the active hydrogen group-containing component include the above-described polyol component.

For the active hydrogen group-containing component, preferably, a high-molecular weight polyol, more preferably, polyester polyol is used.

When producing the polyurethane resin of the present invention as a granular polyurethane resin, the active hydrogen group-containing component contains a chain extender.

Examples of the chain extender include the same chain extenders as those used when the polyurethane resin of the present invention is produced as an aqueous polyurethane resin, and specific examples thereof include low-molecular-weight polyols such as the above-mentioned dihydric alcohols and the above-mentioned trihydric alcohols; and polyamine components such as the above-mentioned alicyclic diamines and the above-mentioned aliphatic diamines.

As the chain extender, dihydric alcohols are preferable, or ethylene glycol, 1,3-propanediol, 1,4-butanediol, and 1,6-hexamethylene glycol are more preferable.

For the active hydrogen group-containing component, as necessary, for example, the above-described low molecular-weight polyol, polythiol component, polyamine component, monol and/or monoamine can be used together.

The polyisocyanate component can be allowed to react with the active hydrogen group-containing component in conformity with a known polyurethane molding method, for example, by the above-described one shot process (the one shot process used for producing the polyurethane resin of the present invention as elastomers), and the above-described prepolymer process (the prepolymer process used for producing the polyurethane resin of the present invention as elastomers). Preferably, the polyisocyanate component is allowed to react with the active hydrogen group-containing component by the prepolymer process.

When the one shot process is used, the above-described components, and the above-described polyisocyanate component and the above-described active hydrogen group-containing component are blended at the same time at such a ratio that the equivalent ratio (NCO/active hydrogen group) of the isocyanate group in the polyisocyanate component relative to the active hydrogen group in the active hydrogen group-containing component is, for example, 0.8 to 1.1, preferably 0.9 to 1.05.

This reaction is continued, for example, under a nitrogen atmosphere at a reaction temperature of 40 to 260° C., or preferably 80 to 220° C. for a reaction time of 0.5 to 10 hours, or preferably 2 to 8 hours.

In the reaction, if necessary, the above-mentioned urethanizing catalyst (urethanizing catalyst used when producing the polyurethane resin of the present invention as an elastomer) or the above-mentioned organic solvent (organic solvent used when producing the polyurethane resin of the present invention as an elastomer) can be added.

The urethanizing catalyst is added in an amount of, for example, 0.001 to 5 parts by mass, or preferably 0.01 to 3 parts by mass, relative to 100 parts by mass of the high-molecular-weight polyol.

Then, in the one shot process, the polyurethane resin thus obtained is, if necessary, crushed by a known method and thereafter, a freeze crushing method is performed to produce the polyurethane resin of the present invention in the form of powder.

When the prepolymer process is used, first, the components are blended and allowed to react at a ratio such that the equivalent ratio (NCO/active hydrogen group) of the isocyanate group in the polyisocyanate component relative to the active hydrogen group in the active hydrogen group-containing component (e.g., high-molecular weight polyol, and, those components blended necessary such as a low molecular-weight polyol, polythiol component, polyamine component, monol and monoamine) excluding the chain extender is, for example, 1.1 to 4, preferably 1.4 to 2.5, thereby producing an isocyanate group-terminated prepolymer.

When the above equivalent ratio is less than 1.1, the polyurethane resin has an excessively high molecular weight, which may deteriorate moldability. On the other hand, when it exceeds 4, the slush molded article may become hard, which may damage the texture.

This reaction is continued, for example, under a nitrogen atmosphere at a reaction temperature of 40 to 180° C., or preferably 60 to 140° C. for a reaction time of 0.5 to 10 hours, or preferably 2 to 8 hours, and in the reaction system, the reaction is terminated at the time when a desired isocyanate group content (e.g., 1 to 12% by mass) is obtained, in the reaction, if necessary, the above-mentioned urethanizing catalyst (urethanizing catalyst used when producing the polyurethane resin of the present invention as an elastomer) or the above-mentioned organic solvent (organic solvent used when producing the polyurethane resin of the present invention as an elastomer) can be added.

Subsequently, the isocyanate group-terminated prepolymer thus obtained and the chain extender are blended at such a ratio that the equivalent ratio (active hydrogen group/NCO) of the active hydrogen group in the chain extender to the isocyanate group in the isocyanate group-terminated prepolymer is in the range of, for example, 0.8 to 1.1, or preferably 0.9 to 1.05, and the blended mixture is subjected to a chain extension reaction, whereby a polyurethane resin is produced.

In the chain extension reaction, for example, the isocyanate group-terminated prepolymer is dispersed in a non-aqueous dispersion medium or an aqueous dispersion medium to prepare a dispersion of the isocyanate group-terminated prepolymer, and a chain extender is added at once or in portions to the dispersion.

Examples of the non-aqueous dispersion medium include the above-mentioned organic solvents, and examples of the aqueous dispersion medium include water, or mixed solutions of water and alcohols (e.g., methanol, ethanol, etc.).

The blending amount of the non-aqueous dispersion medium or the aqueous dispersion medium is in the range of, for example, 10 to 200 parts by mass, or preferably 20 to 150 parts by mass, relative to 100 parts by mass of the isocyanate group-terminated prepolymer.

When the isocyanate group-terminated prepolymer is dispersed in the aqueous dispersion medium, for example, the above-mentioned hydrophilic group-containing active hydrogen compound (hydrophilic group-containing active hydrogen compound used when producing the polyurethane resin of the present invention as an aqueous polyurethane resin) is contained in the active hydrogen group-containing component in the preparation of the isocyanate group-terminated prepolymer, whereby the isocyanate group-terminated prepolymer can be internally emulsified.

Alternatively, when the isocyanate group-terminated prepolymer is dispersed in the aqueous dispersion medium, the same external emulsifier as the above-mentioned external emulsifier (external emulsifier used when producing the polyurethane resin of the present invention as an aqueous polyurethane resin) is added to the aqueous dispersion medium and/or the isocyanate group-terminated prepolymer, whereby the isocyanate group-terminated prepolymer can also be externally emulsified.

Further, a dispersion stabilizer can be added to the dispersion in order to prevent the sedimentation of the dispersed phase. Examples of the dispersion stabilizer include dispersing agents described in Japanese Unexamined Patent Publication No. 2004-169011, such as resin obtained by dehydration condensation of an alkenyl succinic anhydride and a polyol or a polyester polyol; alkyd resin obtained by dehydration condensation of a part of the remaining OH groups of the polyester, which is produced by dehydration condensation of dicarboxylic acid and pentaerythritol, with fatty acids; resin obtained by grafting an ethylenically unsaturated monomer onto a polyol obtained by dehydration condensation of an unsaturated bond-containing dicarboxylic acid and a polyol or a polyester polyol, and thereafter masking an OH group; and resin obtained by masking an OH group of a polyol obtained by dehydration condensation of an unsaturated bond-containing dicarboxylic acid and a polyol or a polyester polyol, and thereafter grafting an ethylenically unsaturated monomer.

The blending amount of the external emulsifier or the dispersion stabilizer is in the range of, for example, 0.05 to 5 parts by mass, preferably 0.1 to 3 parts by mass, or more preferably 0.15 to 1.5 parts by mass, relative to 100 parts by mass of the isocyanate group-terminated prepolymer.

The chain extension reaction is conducted, for example, at a reaction temperature of 10 to 100° C., or preferably 20 to 90° C. for a reaction time of 0.5 to 8 hours, or preferably 2 to 6 hours. In the reaction, if necessary, the above-mentioned known urethanizing catalyst can be added.

Thus, the polyurethane resin can be produced in the form of a dispersion.

In the chain extension reaction, without dispersing the isocyanate group-terminated prepolymer in the non-aqueous dispersion medium or the aqueous dispersion medium, the isocyanate group-terminated prepolymer and the chain extender can be allowed to react directly with each other.

As for the polyurethane resin of the present invention, when the dispersion is prepared from a non-aqueous dispersion medium, solids are separated, for example, by separation means such as filtration to obtain a polyurethane resin in the form of powder. On the other hand, when the dispersion is prepared from an aqueous dispersion medium, solids are separated, for example, by spray drying to obtain a polyurethane resin in the form of powder. Further, when the isocyanate group-terminated prepolymer and the chain extender are allowed to react directly with each other without dispersing in the non-aqueous dispersion medium or the aqueous dispersion medium, a polyurethane resin is produced in the form of powder, for example, by a freeze crushing method.

Also, when the polyurethane resin of the present invention is produced as a granular polyurethane resin, further, known additives such as a plasticizer, antiblocking agent, heat-resistant stabilizer, light-resistant stabilizer, antioxidant, and releasing agent; further, an antioxidant, pigment, dye, lubricant, filler, and hydrolysis inhibitor; or further, a thermally crosslinkable monomer and polymerization inhibitor can optionally be blended at an appropriate ratio. These additives may be added at the time of synthesizing components, or may be added at the time of mixing and dissolving components, or may be added after the synthesis.

According to the polyurethane resin of the present invention thus obtained in the form of powder (granular polyurethane resin), a slush molded article excellent in releasability from a mold after molding in the slush molding, tensile strength, and thermal properties, and further having excellent durability, texture (feel), and appearance can be slush-molded with high production efficiency.

Therefore, the slush molded article of the present invention is excellent in tensile strength and thermal properties, and further has excellent texture (feel) and appearance.

Accordingly, the polyurethane resin of the present invention produced as a granular polyurethane resin and a mold article thereof are useful in various fields involving slush molding, for example, furniture such as sofas and bedding; toys; sporting goods; and toner binders, and are particularly useful in automobile interior trim articles. The polyurethane resin (granular polyurethane resin) of the present invention is useful in fields other than those involving slush molding, for example, toner binders.

Next, the case of producing an elastic molded article (spandex) as the polyurethane resin of the present invention will be explained.

In this case, the polyurethane resin of the present invention is produced as a polyurethane resin for elastic molding by reaction of the above-described polyisocyanate component with the above-described active hydrogen group-containing component.

When producing the polyurethane resin of the present invention as a polyurethane resin for elastic molding, the polyisocyanate component includes the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as a polyurethane resin for elastic molding, for the active hydrogen group-containing component, for example, the above-described polyol component is used.

For the active hydrogen group-containing component, preferably, a high-molecular weight polyol, more preferably, polyester polyol, polyether polyol, polycarbonate polyol are used. Examples of polyether polyol include the above-described polytetramethylene ether glycol and polytrimethyleneetherglycol. Polyethylene glycol can also be used. The CPR (controlled polymerization rate) of the polyalkylene polyol including polyethylene glycol is 5 or less, even more preferably 3 or less, most preferably 2 or less. The CPR is measured in accordance with the method described in JIS K 1557-1. By using polyoxyalkylene polyol having a CPR in such a range, side reactions based on the isocyanate group in reaction with 1,4-bis(isocyanatomethyl)cyclohexane of the present invention can be suppressed.

Examples of the chain extender include the same chain extenders as those used when the polyurethane resin of the present invention is produced as an aqueous polyurethane resin, and specific examples thereof include low-molecular-weight polyols such as the above-mentioned dihydric alcohols and the above-mentioned trihydric alcohols; and polyamine components such as the above-mentioned alicyclic diamines and the above-mentioned aliphatic diamines. Among them, a polyamine component is preferable, or aliphatic diamine is more preferable.

As the chain extender used in the case of producing the polyurethane resin of the present invention as a polyurethane resin for elastic molding, the above-mentioned monoamine can be used. Further, as long as the moldability or extensibility of the polyurethane resin is not impaired, an amine compound such as bis-(4-amino-3-chlorophenyl)methane, diethyltoluenediamine, dimethylthiotoluenediamine, trimethylene-bis(4-aminobenzoate), or 4,4'-diamino-3,3-diethyl-5,5-dimethyldiphenylmethane can also be used.

These chain extenders may be used singly or in combination of two or more. In particular, the polyurethane resin of the present invention can be adjusted to a desired molecular weight by using a polyamine component and a monoamine in combination. Among them, as the polyamine component, ethylenediamine, hydrazine (including hydrate thereof), 1,2-diaminopropane, 1,4-bis(aminomethyl)cyclohexane, and 1,4-cyclohexanediamine are preferable, and as monoamine, di-n-butylamine and diethylamine are preferable. More preferable is a combination use of diethylamine and ethylenediamine (e.g., diethylamine (DEA) and ethylenediamine (EDA) at a molar ratio (DEA/EDA) of 0.5/99.5 to 20/80).

When the chain extension is performed by using these chain extenders, a urea group ($-NH_2-CO-NH_2-$) can be contained in a hard segment (a segment obtained by the reaction between the polyisocyanate component and the chain extender) contained in the polyurethane resin. Therefore, a polyurethane resin having excellent elasticity and extensibility can be produced.

For the active hydrogen group-containing component, as necessary, for example, the above-described low molecular-weight polyol, polythiol component, polyamine component, monol and/or monoamine can be used together.

The polyisocyanate component can be allowed to react with the active hydrogen group-containing component in conformity with a known polyurethane molding method, for example, by the above-described one shot process (the one shot process used for producing the polyurethane resin of the present invention as elastomers), and the above-described prepolymer process (the prepolymer process used for producing the polyurethane resin of the present invention as elastomers).

When the one shot process is used, the above-described components, and the above-described polyisocyanate component and the above-described active hydrogen group-containing component are blended at the same time at such a ratio that the equivalent ratio (NCO/active hydrogen group) of the isocyanate group in the polyisocyanate component relative to the active hydrogen group in the active hydrogen group-containing component is, for example, 0.9 to 1.1, preferably 0.98 to 1.05.

This reaction can be conducted in the same manner as the bulk polymerization (bulk polymerization performed when producing the polyurethane resin of the present invention as an elastomer) or the solution polymerization (solution polymerization performed when producing the polyurethane resin of the present invention as an elastomer).

When the bulk polymerization is used, for example, the above-mentioned components are allowed to react under a nitrogen atmosphere at a temperature of 100 to 250° C. or preferably 130 to 220° C. for 0.5 to 12 hours, or preferably 1 to 10 hours.

When the solution polymerization is used, for example, the above-mentioned components are allowed to react under a nitrogen atmosphere at a temperature of 30 to 100° C. or preferably 40 to 90° C. for 2 to 10 hours, or preferably 3 to 8 hours.

When the prepolymer process is used, first, the components are blended and allowed to react at a ratio such that the equivalent ratio (NCO/active hydrogen group) of the isocyanate group in the polyisocyanate component relative to the active hydrogen group in the active hydrogen group-containing component (e.g., high-molecular weight polyol, and those components blended as necessary such as a low molecular-weight polyol, polythiol component, polyamine component, monol and monoamine) excluding the chain extender is, for example, 1.1 to 5, preferably 1.3 to 3, even more preferably 1.3 to 2.5, thereby producing an isocyanate group-terminated prepolymer.

This reaction is continued, for example, under a nitrogen atmosphere at a reaction temperature of 40 to 130° C., or preferably 50 to 120° C. for a reaction time of 1 to 10 hours, or preferably 2 to 6 hours. In the reaction, if necessary, the above-mentioned urethanizing catalyst (urethanizing catalyst when producing the polyurethane resin of the present invention as an elastomer) or an organic solvent can also be added.

Subsequently, the isocyanate group-terminated prepolymer thus obtained and the chain extender are blended at such a ratio that the equivalent ratio (NCO/active hydrogen group) of the isocyanate group in the isocyanate group-terminated prepolymer to the active hydrogen group in the chain extender is in the range of, for example, 0.9 to 1.1, or preferably 0.98 to 1.05, and the blended mixture is subjected to chain extension reaction, whereby a polyurethane resin is produced.

In the chain extension reaction, for example, the isocyanate group-terminated prepolymer and the chain extender are allowed to react by dissolving them in an organic solvent. Thus, a polyurethane resin in which the isocyanate group-terminated prepolymer is chain-extended by the chain extender can be produced in the form of a solution.

Examples of the organic solvent include the above-described organic solvent, and preferably, N,N'-dimethylacetamide, N,N-dimethylformamide are used.

The isocyanate group-terminated prepolymer and the chain extender are allowed to react in the organic solvent in the following manner. For example, first, a solvent is added to the isocyanate group-terminated prepolymer, and the isocyanate group-terminated prepolymer is dissolved to prepare a prepolymer solution. Subsequently, the chain extender is added to this prepolymer solution to chain-extend the isocyanate group-terminated prepolymer.

The isocyanate group-terminated prepolymer is dissolved in a solvent by gradually adding the organic solvent to the isocyanate group-terminated prepolymer under stirring. The organic solvent is added at a ratio of preferably 100 to 900 parts by mass relative to 100 parts by mass of the isocyanate group-terminated prepolymer. To be more specific, the organic solvent is added so that the isocyanate group-terminated prepolymer concentration is, for example, 10 to 50 mass %, preferably 20 to 40 mass %, more preferably 25 to 35 mass %.

During the dissolution, the temperature of the isocyanate group-terminated prepolymer is preliminarily lowered to, for example, 50° C. or less, or preferably 40° C. or less.

Subsequently, the chain extender is added to the prepolymer solution so as to give the above-mentioned proportion. When a polyamine component is used as the chain extender, the polyamine component is added at a temperature of preferably 20° C. or less, and after completion of the addition, the mixture is further stirred to complete the reaction at a temperature of, for example, 25 to 80° C. On the other hand, when a low-molecular-weight polyol is used as the chain extender, the chain extender is added dropwise at a temperature of preferably 40 to 90° C., and the reaction is completed within this temperature range. The chain extender can also be added as a chain extender solution of the solvent. Furthermore, when the low molecular-weight polyol is used as a chain extender, the above-described urethanizing catalyst can be used. In this case, the urethanizing catalyst can also be used by dissolving the urethanizing catalyst in the solvent.

Meanwhile, in the method of producing elastic fiber by molding with melt spinning, the above-described thermoplastic urethane elastomer (TPU) may be used. Examples of the high-molecular weight polyol include polytetramethylene ether glycol, noncrystalline polytetramethylene ether glycol having a side chain of, for example, methyl group, polytrimethyleneetherglycol, and polyethylene glycol.

The number average molecular weight is preferably 600 to 5000, even more preferably 800 to 4000, most preferably about 1000 to 2500.

TPU in this application is preferably produced by prepolymer process, and the components are blended and allowed to react so that the above-described equivalent ratio (NCO/active hydrogen group) of the isocyanate group in the polyisocyanate component is, for example, 1.1 to 5, preferably 1.3 to 4.5, even more preferably 1.3 to 4, thereby producing an isocyanate group-terminated prepolymer.

Thereafter, chain extension reaction is performed. For the low molecular-weight glycol in this case, ethylene glycol, 1,3-propanediol, and 1,4-butanediol are preferable.

The hardness (A) is preferably about 70 to 95, even more preferably about 80 to 93.

The TPU produced by allowing, for example, an isocyanate group-terminated prepolymer, which is produced by allowing 1,4-bis(isocyanatomethyl)cyclohexane of the present invention to react with a high-molecular weight polyol of polyethylene glycol having a number average molecular weight of 2000 so that the equivalent ratio (NCO/active hydrogen group) is 4, to react with a chain extender of 1,4-butanediol so that the equivalent ratio (NCO/active hydrogen group) is 1.05 has moisture permeability, and also because of its tendency for orientation in uniaxial extension direction, the TPU thus produced has significantly increased stress in that direction. Therefore, the TPU can be suitably used in various materials for molding such as melt spinning in which uniaxial elongational flow occurs, film molding, and blow molding.

To the fiber thus produced, for example, polyester, and nylon fiber can be mixed to produce a fabric having elasticity and excellent texture. For example, in the fabric, 1 to 60% is preferably the polyurethane fiber, and even more preferably, about 2 to 40% is the polyurethane fiber.

The thus produced polyurethane resin has a number average molecular weight (number average molecular weight determined by GPC using a calibration curve of standard polystyrene) of for example, 40,000 to 300,000, preferably 50,000 to 250,000.

When producing the polyurethane resin of the present invention as a polyurethane resin for elastic molding, a sulfonamide group-containing compound having a sulfonamide group is preferably contained according to the purposes and applications.

The containing of the sulfonamide group-containing compound allows the polyurethane resin of the present invention produced as a polyurethane resin for elastic molding to have improved thermal stability.

Therefore, when the polyurethane resin for elastic molding is used for elastic molded articles subjected to heat treatment (e.g., drying treatment), for example, elastic fibers such as clothes and socks, the containing of the sulfonamide group compound in the polyurethane resin for elastic molding can produce elastic fibers, sheets, or the like which are excellent in thermal stability.

Examples of the sulfonamide group-containing compound include the compound containing a sulfonamide group mentioned above as a stabilizer, such as aromatic sulfonamides and aliphatic sulfonamides.

These sulfonamide group-containing compounds may be used singly or in combination of two or more. Among them, aromatic sulfonamides are preferable, or o-toluene sulfonamide, p-toluene sulfonamide, and mixtures thereof are more preferable.

When the polyurethane resin of the present invention is produced as a polyurethane resin for elastic molding, and when the polyurethane resin of the present invention contains a sulfonamide group-containing compound, the content of the sulfonamide group-containing compound to the polyurethane resin is in the range of, for example, preferably 1 to 10000 ppm, more preferably 10 to 8000 ppm, and even more preferably 100 to 3000 ppm on mass basis.

To contain the sulfonamide group-containing compound in the polyurethane resin, for example, the sulfonamide group-containing compound may be blended with the polyisocyanate component or the active hydrogen group-containing component, or added to the prepolymer solution, though not limited thereto.

Also, when the polyurethane resin of the present invention is produced as a polyurethane resin for elastic molding, further, known additives such as a plasticizer, antiblocking agent, heat-resistant stabilizer, light-resistant stabilizer, NOx yellowing prevention agent, and releasing agent; or further, a pigment, dye, lubricant, filler, and hydrolysis inhibitor can optionally be added. These additives may be added during synthesis of each component or may be added during mixing and dissolving of the components, and further they can also be added after separation/drying of the polyurethane resin.

Examples of the heat-resistant stabilizer include the above-described antioxidants, and a mixture of polyurethane produced by reaction of t-butyldiethanol amine with methylene-bis-(4-cyclohexylisocyanate), and a polymer of p-cresol and divinylbenzene.

Examples of the NOx yellowing prevention agent include the above-described NOx yellowing prevention agent.

According to the polyurethane resin of the present invention produced as a polyurethane resin for elastic molding, it is possible to suppress the deterioration of mechanical strength and the residual strain under cyclic deformation, to improve thermal properties, tensile strength at break, elongation at break, and strength development, and further to improve yellowing resistance.

Therefore, even under cyclic deformation, the molded article of the present invention is less susceptible to deterioration of mechanical strength and hardly causes residual strain. It is also excellent in thermal properties, tensile strength at break, elongation at break, and strength development, and further has excellent durability and yellowing resistance.

Therefore, the molded article of the present invention is useful for various elastic molded articles (spandex) requiring elastic performance, such as elastic fibers used for various textiles including socks, stocking, circular knitted fabric, tricot, swimming suits, ski pants, working clothes, fire-proof clothing, clothes, golf trousers, controlling undergarment, wet suits, brassiere, girdles, and gloves; elastic films used as food wrap film; and fastening materials for leakage prevention of sanitary products including disposable diapers, securing materials for waterproofing materials, artificial baits, artificial flowers, electric insulating materials, wiping cloth, copy cleaners, and gaskets.

When using the polyurethane resin of the present invention as an elastic fiber, the elastic fibers can be produced by a known spinning method such as melt spinning, dry spinning, and wet spinning.

When the elastic fibers are produced by a melt spinning method, the specific spinning conditions are as follows. For example, the spinning temperature is in the range of 160 to 250° C., and the spinning speed is adjusted so as to produce 10 to 100-denier yarn. Then, the spun elastic fibers are used in the state of, for example, covering yarn or bare yarn.

On the other hand, when used for elastic films, the polyurethane resin of the present invention can be made by a known method such as solvent casting or T-die casting, or inflation.

When an elastic film is made by a T-die casting method and an inflation method, the specific film forming conditions are as follows. For example, the die temperature is in the range of 160 to 230° C., and the winding speed is adjusted to give a film thickness of 20 to 100 μm. In addition, when an elastic sheet is made, the die lip width and the winding speed are adjusted. Thus, a molded article (elastic sheet) having a thickness exceeding 100 μm can be produced.

The polyurethane resin of the present invention is not limited to the above-mentioned elastic molded articles, and can be used for various applications such as nonwoven cloth produced by a method including spunbond and meltblown forming; paints; and raw material of adhesives produced by a method including hot melt method.

Next, the case of producing the polyurethane resin of the present invention as a polyurethane resin for reaction injection molding (RIM) will be explained.

The polyurethane resin of the present invention produced as a polyurethane resin for RIM can be produced by reaction of the above-described polyisocyanate component with the above-described active hydrogen group-containing component.

When producing the polyurethane resin of the present invention as a polyurethane resin for RIM, the polyisocyanate component include the above-described 1,4-bis(isocyanatomethyl)cyclohexane and/or the above-described polyisocyanate composition, and preferably, the above-described 1,4-bis(isocyanatomethyl)cyclohexane is used singly.

When producing the polyurethane resin of the present invention as a polyurethane resin for RIM, for the active hydrogen group-containing component, for example, the above-described polyol component is used.

For the active hydrogen group-containing component, preferably, a high-molecular weight polyol, more preferably, a polyether polyol is used.

For the active hydrogen group-containing component, as necessary, for example, the above-described low molecular-weight polyol, polythiol component, polyamine component, monol and/or monoamine can also be used in combination.

When producing the polyurethane resin of the present invention as a polyurethane resin for RIM, the polyurethane resin can be molded with a known reaction injection molding apparatus. The known reaction injection molding apparatus is an apparatus equipped with at least (1) a first supply tank for supplying a polyisocyanate component, (2) a second supply tank for supplying an active hydrogen group-containing component, (3) a mixing head for mixing the polyisocyanate component and the active hydrogen group-containing component to inject the mixture into a mold, and (4) a mold.

Specifically, first, a polyisocyanate component and an active hydrogen group-containing component are supplied from the first supply tank (1) and the second supply tank (2), respectively, to the mixing head (3). At this time, the raw material temperature of the polyisocyanate component is adjusted to, for example, 35 to 55° C. On the other hand, the raw material temperature of the active hydrogen group-containing component is also adjusted to, for example, 35 to 55° C. During mixing, the index (INDEX), which is represented by the molar ratio of the isocyanate group in the polyisocyanate component to the active hydrogen group in the active hydrogen group-containing component in terms of percentage, is in the range of, for example, 80 to 120 and is preferably set to 95 to 105.

Then, the polyisocyanate component and the active hydrogen group-containing component are mixed with stirring in the mixing head (3), and the mixture is injected into the mold (4) at an injection rate of, for example, 200 to 2500 g/sec. The mold (4) is preliminarily pressurized with a pressure of, for example, 10 to 30 MPa (gauge pressure) and heated to a temperature of 60 to 80° C. Further, if necessary, a releasing agent such as an aqueous wax emulsion is applied to the molding surface of the mold (4) to improve the mold releasability of a molded article.

Then, the polyisocyanate component and the active hydrogen group-containing component are injected into the mold (4), and thereafter, both of the components are subjected to polymerization in the mold (4), for example, for 1 to 3 minutes. Subsequently, the mold (4) is cooled to room temperature and the pressure therein is reduced to normal pressure, and the resulting reaction injection molded article is released from the mold (4) to obtain a reaction injection molded article.

Also, when the polyurethane resin of the present invention is produced as a polyurethane resin for RIM, further, known additives such as the above-mentioned urethanizing catalyst (urethanizing catalyst used when producing the polyurethane resin of the present invention as an elastomer), a light-resistant stabilizer (ultraviolet absorber), antioxidant (heat-resistant stabilizer), or multifunctional stabilizer can optionally be blended at an appropriate ratio. These additives are preliminarily added to the polyisocyanate component and/or the active hydrogen group-containing component. Preferably, these additives are preliminarily added to the active hydrogen group-containing component.

Examples of the urethanizing catalyst include those mentioned above. Among them, an organometallic compound is preferable, and dibutyl tin dineodecanoate is more preferable. The amount of the urethanizing catalyst added is in the range of, for example, 0.1 to 1.5 parts by mass, or preferably 0.3 to 1.0 parts by mass, relative to 100 parts by mass of the active hydrogen group-containing component.

Examples of the light-resistant stabilizer (ultraviolet absorber) include the above-described light-resistant stabilizer (light-resistant stabilizer in the production of polyurethane foam). Among them, a benzotriazol type ultraviolet absorber and a hindered amine type ultraviolet absorber are preferable. The light-resistant stabilizer is added in an amount of, for example, 0.1 to 1.0 parts by mass, preferably 0.3 to 0.7 parts by mass relative to 100 parts by mass of the active hydrogen group-containing component.

Examples of the antioxidant (heat-resistant stabilizer) include the above-described heat-resistant stabilizer (heat-resistant stabilizer in production of polyurethane foam). Among them, a hindered phenol type stabilizer is preferable. The antioxidant is added in an amount of, for example, 0.1 to 1.0 parts by mass, preferably 0.3 to 0.7 parts by mass relative to 100 parts by mass of the active hydrogen group-containing component.

Examples of the multifunctional stabilizer include the above-described multifunctional stabilizer (multifunctional stabilizer in production of polyurethane foam). Preferably, a benzotriazolyl-alkylbisphenol compound is used. The multifunctional stabilizer is added in an amount of, for example, 0.1 to 1.0 parts by mass, preferably 0.3 to 0.7 parts by mass relative to 100 parts by mass of the active hydrogen group-containing component.

Further, depending on the applications, known additives such as a chain extender, crosslinking agent, pigment, flame retardant, pigment dispersing agent (lubricating dispersing agent), foam stabilizer, or antifoaming agent can also be blended with the mixture of the polyisocyanate component and the active hydrogen group-containing component at an appropriate ratio.

According to the polyurethane resin of the present invention produced as a polyurethane resin for injection molding, a reaction injection molded article excellent in releasability from the mold after molding, hardness, thermal properties, and tear resistance development, and further having excellent weather resistance can be injection-molded with high production efficiency.

Therefore, the reaction injection molded article of the present invention is excellent in hardness, thermal properties, and tear resistance development, and is further excellent in durability and weather resistance.

Accordingly, the polyurethane resin of the present invention produced as a polyurethane resin for reaction injection molding and a reaction injection molded article thereof are useful in various fields involving reaction injection molding, for example, transportation equipment components such as automobile bumpers, dashboards, door trims, and instrument panels; interior parts of stores, offices, and other buildings; and home and office furniture, and particularly useful in skin layers of interior decorative materials in transportation equipment, such as automobile instrument panels and door trims; and various covers such as the following, including, covers for golf ball core, cover materials for soccer, baseball, basket or volleyball, vehicle gear knob covers, door sealing covers, tale lamp covers, spring covers, console box covers, electric wires, or optical fiber cable covers, keyboard covers, audio components covers, grip covers for sporting products such as tennis rackets, door mirror covers, tubes, and hoses. Preferably, the molded articles can be suitably used in various industrial fields including the following examples: cover materials for golf ball core layers; optical materials such as on-vehicle light panel, head light lens, head light and tail light lamp cover, optical element, optical disc, organic EL, and LED; and optical components such as illumination including signboard, optical fiber, glass alternatives, intermediate film for laminated glass, windshield for airplane, large-scale water tank wall, transparent roofing material, grazing material, transparent member for commodities, optical lenses such as transparent lenses, spectacle lens, camera lens, pick-up lens, contact lens, sunglass lenses, and polarizing lenses; electronic components; automobile parts, mechanical and industrial parts, electric wire•cables, rolls, hoses•tubes, belts, films•sheets, laminate products, elastic paving materials, civil engineering and construction materials, coating, adhesive, sealing material, sealant for various base materials of marine products; core materials for golf balls; sports and leisure products such as basketball, soft balls, tents, and ski boots; shoe-related products, miscellaneous goods, nursing care products, residence products, medical products, building material, civil-engineering related products, waterproof materials and paving materials, foam, slash powder, robot member, elastic apparel, elastic fiber, nonwoven fabric, and furthermore, rolls involved with production of paper manufacturing, iron steel, printer copy, liquid crystal, PDP, organic EL, chemical or physical foaming urethane products, microcellular, optical sheet, film, cleaning blade, squeegee, and furthermore, cushioning material, self-recovery material, truck, floor material, Bullet train, ships, gasket for linear motor, sealing material, soles, inner and outer members for shoes, urethane disc, cushion board, torque limiter, pinch roller, press roll, sporting products, golf ball, basketball, volleyball, and robot members.

Furthermore, the present invention includes an eyewear material composed of the above-described polyurethane resin.

That is, conventionally, eyewear such as corrective glasses, protection glasses, sunglasses, and goggles includes a lens and a frame. In such an eyewear, the frame is formed, for example, from metal materials such as pure titanium, a nickel titanium alloy, aluminum, magnesium, and gold; synthetic resin materials such as celluloid, acetate, and polyamide resin; and natural materials such as tortoiseshell.

Meanwhile, improvement in mechanical properties (mechanical strength, etc.) and workability/processability are demanded for eyewear. Thus, use of a polyurethane elastomer that has excellent mechanical properties and workability/processability for an eyewear material has been examined.

Thus, an eyewear material having excellent mechanical strength and workability/processability, and an eyewear frame and a lens produced by using the eyewear material have been demanded.

Thus, the above-described polyurethane resin (thermoplastic polyurethane elastomer (TPU)) can be used as an eyewear material. To be more specific, eyewear frame, to be more specific, each part of an eyewear frame such as nose pads, earpiece (ear pads), temple (string portion), rim (lens surrounding), bridge (rim connecting portion), end piece (front both end portions), hinge (connecting portion between end piece and temple) of an eyewear can be produced using the above-described polyurethane resin (thermoplastic polyurethane elastomer (TPU)). Furthermore, an eyewear frame including all of the above-described parts can also be molded integrally.

Such an eyewear frame can be produced by pelletizing the eyewear material (the above-described thermoplastic polyurethane elastomer (TPU)), and molding the eyewear material into a desired frame shape by a known molding method such as extrusion molding and injection molding.

For the eyewear frame molding, as necessary, along with the above-described eyewear material, other thermoplastic resin may be used.

Examples of other thermoplastic resin include thermoplastic polyamide described in Japanese Unexamined Patent Application Publication (Translation of PCT Application) 2010-534256, the blended resin of polyether-imide and polyphenylene ether sulfone described in Japanese Unexamined Patent Application Publication (Translation of PCT Application) 2010-532815, and polymethylpentene resin of commercially available products (trade name TPX series (manufactured by Mitsui Chemicals, Inc.), etc.), cyclic olefin copolymer (trade name Apel series (manufactured by Mitsui Chemicals, Inc.), etc.), and thermoplastic polyimide (trade name Aurum series (manufactured by Mitsui Chemicals, Inc.), etc.).

When these other thermoplastic resin is used, for example, an eyewear material containing the above-described polyurethane resin, and other thermoplastic resin (e.g., thermoplastic polyamide, etc.) are simultaneously injection molded, thereby composite molding an eyewear frame.

When the above-described eyewear material is used in combination with other thermoplastic resin, for example, 20 mass % or more, preferably 50 mass % or more, and 90 mass % or less, preferably 70 mass % or less of the above-described eyewear material is blended relative to a total of the eyewear material and other thermoplastic resin.

Furthermore, for example, a specific eyewear part is formed by using the above-described eyewear material, and other eyewear parts are formed by using other thermoplastic resin.

To be more specific, the eyewear frame can be produced from a plurality of resins by using the above-described eyewear material for, for example, nose pads and earpiece (ear pads), and furthermore, using other thermoplastic resins (e.g., thermoplastic polyamide, etc.) for temple (string portion), and rim (lens surrounding).

The eyewear frame can be coated with a coating agent such as a polyurethane-based coating agent in view of appearance and solvent-resistant characteristics and design.

Furthermore, an eyewear material composed of the polyurethane resin of the present invention can also be suitably used for an eyewear lens (plastic lens). Examples of the eyewear material used for lenses include, to be more specific, the above-described optical polyurethane resin.

The lens produced from the above-described optical polyurethane resin has excellent appearance (transparency), and also refraction, mechanical properties (tensile strength), and durability.

Such a lens is attached (fitted to) to the eyewear frame, thereby forming an eyewear.

The eyewear frame may be the above-described eyewear frame of the present invention, or may be other known eyewear frame. Preferably, the lens is attached (fitted) to the above-described eyewear frame of the present invention.

To the above-described lens, as necessary, a coating layer is laminated to one side or both sides thereof. Examples of the coating layer include, for example, a primer layer, hard coat layer, antireflection coating layer, anti-fogging coating layer, antifouling layer, and water-repellent layer. These coating layers can be laminated to the lens singly, or can be laminated to the lens in multiple layers.

When multiple coating layers are formed, or when the coating layer is laminated on both sides of the lens, the coating layers may be the same or different from each other.

Such an eyewear frame, lens, and eyewear produced from the eyewear material contains the above-described polyurethane resin, and therefore have excellent workability/processability, mechanical strength, and furthermore optical properties, and anti NOx properties (light-resistant properties, heat resistance).

Therefore, the above-described eyewear is suitably used for corrective glasses, protection glasses, sunglasses, and goggles: to be more specific, eyewear for sports; eyewear having anti-fogging functions used in high temperature and high humidity place such as bathroom and sauna; electronic device attached eyewear having distributed music and images functions; electronic lens-attached eyewear having liquid crystal functions; and furthermore, eyewear for internet functions, eyewear for functions for cares for pollen protection, eyewear for nearsighted, far-sighted, and aged eye; eyewear for protection against cataract and glaucoma; and eyewear containing mentally relaxing perfume.

EXAMPLES

While in the following, the present invention is described with reference to Examples and Comparative Examples, the present invention is not limited to any of them. In the following description, the units "part(s)" and "%" are by mass, unless otherwise noted. The numeral values shown in Examples below can be interchanged with the corresponding numeral values shown in the embodiments (that is, upper limit value or lower limit value).

Preparation of 1,4-bis(aminomethyl)cyclohexane

Production Example 1

Preparation of 1,4-BAC (A)

[Nuclear Hydrogenation Step of Terephthalic Acid]

A stainless steel-made reactor equipped with a stirrer, a thermometer, and a gas inlet tube was charged with 100 parts by mass of terephthalic acid, 3.8 parts by mass of a catalyst (manufactured by NEChemcat Corporation, 5% Pd/C), and 560 parts by mass of water. After the inside of the reactor was replaced with hydrogen, the mixture was heated to 150° C. under normal pressure while stirring at 400 rpm.

Hydrogen feed was started intermittently when the temperature reached 150° C. so that the pressure was 4 MPa (gauge pressure), and the mixture was allowed to react for 5.5 hours.

After completion of reaction, the temperature was reduced to room temperature, and the reaction product slurry was taken out. To the reaction product slurry, 3300 parts by mass of water was added, and the mixture was heated to 90° C. to dissolve the product. Thereafter, filtering was performed to remove the catalyst.

A portion of the filtrate was collected and subjected to gas chromatography analysis: the terephthalic acid conversion rate was 99% or more, the yield of 1,4-cyclohexanedicarboxylic acid was 92%, and the 1,4-cyclohexanedicarboxylic acid had a trans isomer ratio of 36 mol %.

[Cyanation Step]

A flask equipped with a stirrer, a thermometer, a gas inlet tube, a gas purge line, and a gas cooling device was charged with 100 parts by mass of 1,4-cyclohexanedicarboxylic acid produced in the above-described nuclear hydrogenation step, 43 parts by mass of N,N'-dimethylimidazolidinone, and 1.26 parts by mass of tin oxide (II), and the mixture was heated to 170° C. Thereafter, ammonia gas was allowed to flow at 0.58 mol/hr (relative to 1,4-cyclohexanedicarboxylic acid) while stirring at 500 rpm, and the temperature was increased to 280° C. The temperature was kept constant and reaction was performed for 14 hours. After completion of reaction, cooling was performed to 150° C., and hot filtration was performed to remove solids. The filtrate was analyzed, and it was found that the conversion rate of 1,4-cyclohexanedicarboxylic acid was 100%, the 1,4-dicyanocyclohexane yield was 90.2%, the 1,4-dicyanocyclohexane had a trans isomer ratio of 52 mol %, and the N,N'-dimethylimidazolidinone concentration was 6.9 mass %.

[High Boiling Point Component Separation Step]

A flask equipped with a stirrer, a thermometer, a gas purge lines, and a gas cooling device was charged with the filtrate containing 1,4-dicyanocyclohexane produced in the above-described cyanation step, and heated at a pressure of 4 kPa, a cooling device refrigerant temperature (column top temperature) of 140° C., and a flask internal temperature (column bottom temperature) of 190 to 230° C. The condensate in the gas cooling device was distilled to 90 mass % relative to the charged amount, thereby producing a distillate. The distillate was analyzed, and it was found that the 1,4-dicyanocyclohexane yield was 94.9% relative to the charged amount, and the 1,4-dicyanocyclohexane had a trans isomer ratio of 54 mol %. The 1,4-dicyanocyclohexane concentration at the tank bottom was 43.4 mass %, and the trans isomer ratio thereof was 38 mol %.

[Aminomethylation Step]

A stainless steel-made reactor equipped with a stirrer, a thermometer, and a gas inlet tube having a pressure regulating valve was charged with 100 parts by mass of 1,4-dicyanocyclohexane (trans isomer ratio 54 mol %) produced in the above-described high boiling point component separation step, 1.0 parts by mass of a catalyst (manganese-containing Raney cobalt manufactured by Kawaken Fine Chemicals Co., Ltd.), 98 parts by mass of a 28 mass % ammonia water, and 125 parts by mass of i-butanol. After the inside of the reactor was replaced with hydrogen, the mixture was heated to 120° C. while stirring at 400 rpm. Hydrogen feed was started continuously when the temperature reached 120° C. so that the pressure was 3.5 MPa (gauge pressure), and the mixture was allowed to react until there is no hydrogen absorption.

After completion of reaction, the temperature was reduced to room temperature, and the reaction product liquid was taken out. Filtering was performed to remove the catalyst, thereby producing 1,4-BAC (A). In 1,4-BAC (A), the 1,4-bis(aminomethyl)cyclohexane yield was 93%, and its trans isomer ratio was 54 mol %.

Production Example 2

Preparation of 1,4-BAC (B)

[Isomerization Step]

A stainless steel-made reactor equipped with a stirrer, a thermometer, and a gas inlet tube was charged with 100 parts by mass of 1,4-BAC (A) produced in Production Example 1 (trans isomer ratio 54 mol %), 1.6 parts by mass of a catalyst (5 mass % ruthenium/alumina manufactured by N.E. Chemcat), and 100 parts by mass of heptane. After the inside of the reactor was replaced with hydrogen, the total pressure was rendered 5 MPa (gauge pressure) with hydrogen, and the mixture was heated to 210° C. and allowed to react for 3 hours while stirring at 400 rpm.

After completion of reaction, the temperature was reduced to room temperature, and the reaction product liquid was taken out. Filtering was performed to remove the catalyst.

The filtrate was analyzed, and it was found that the yield of 1,4-bis(aminomethyl)cyclohexane was 92%, and its trans isomer ratio was 79 mol %. It was also found that 0.53 mass % (area ratio by gas chromatography) of 3-azabicyclo[3.2.2]nonane relative to a total amount of 1,4-bis(aminomethyl)cyclohexane and 3-azabicyclo[3.2.2]nonane was contained as by-products. The analysis conditions are to be described later (the same applies in the following).

From the produced filtrate, the heptane solvent was removed by vacuum single evaporation. Thereafter, the reaction product liquid from which the solvent was removed was added to a four-neck flask to which a packed column (filler: HELI PACK, the number of theoretical plates: 5 stages) was set and the reaction product liquid was rectified.

The rectifying conditions are as follows: a column top pressure of 4 kPa, a column bottom pressure of 5 kPa, a reflux ratio of 4, a column top temperature of 135 to 136° C., and a column bottom temperature (tank temperature) of 145 to 160° C. A fraction having a distillation rate of 0 mass % to 87 mass % relative to the charged mass was collected, thereby producing 1,4-BAC (B). With a gas chromatograph analysis with the following conditions, it was found that the 1,4-bis(aminomethyl)cyclohexane had a trans isomer ratio of 82 mol %, and contained, as impurity, 0.61 mass % of 3-azabicyclo[3.2.2]nonane relative to a total amount of 1,4-bis(aminomethyl)cyclohexane and 3-azabicyclo[3.2.2]nonane. The analysis conditions are to be described later (the same applies in the following).

Production Example 3

Preparation of 1,4-BAC (C)

A stainless steel-made reactor equipped with a stirrer, a thermometer, and a gas inlet tube was charged with 100 parts by mass of 1,4-BAC (A) produced in Production Example 1 (trans isomer ratio 54 mol %), 1.5 parts by mass of a catalyst (5 mass % ruthenium/alumina manufactured by N.E. Chemcat), and 100 parts by mass of cyclohexane. After the inside of the reactor was replaced with hydrogen, the total pressure was rendered 5 MPa (gauge pressure) with hydrogen, and the mixture was heated to 210° C. and allowed to react for 2 hours while stirring at 400 rpm.

After completion of reaction, the temperature was reduced to room temperature, and the reaction product liquid was taken out. Filtering was performed to remove the catalyst.

The filtrate was analyzed, and it was found that the yield of 1,4-bis(aminomethyl)cyclohexane was 93%, and its trans isomer ratio was 81 mol %. It was also found that 0.43 mass % of 3-azabicyclo[3.2.2]nonane relative to a total amount of 1,4-bis(aminomethyl)cyclohexane and 3-azabicyclo[3.2.2]nonane was contained as by-products.

From the produced filtrate, the cyclohexane solvent was removed by vacuum single evaporation. Thereafter, the reaction product liquid from which the solvent was removed was added to a four-neck flask to which a packed column (filler: HELI PACK, the number of theoretical plates: 5 stages) was set and the reaction product liquid was rectified.

The rectifying conditions are as follows: a column top pressure of 4 kPa, a column bottom pressure of 5 kPa, a reflux ratio of 1, a column top temperature of 135 to 136° C., and a column bottom temperature (tank temperature) of 145 to 160° C. A fraction having a distillation rate of 0 mass % to 91 mass % relative to the charged mass was collected, thereby producing 1,4-BAC (C). As a result of analysis using a gas chromatograph, it was found that the 1,4-bis(aminomethyl)cyclohexane had a trans isomer ratio of 82 mol %, and contained, as impurity, 0.48 mass % of 3-azabicyclo[3.2.2]nonane relative to a total amount of 1,4-bis(aminomethyl)cyclohexane and 3-azabicyclo[3.2.2]nonane.

Production Example 4

Preparation of 1,4-BAC (D)

Reaction was carried out in the same manner as in Production Example 2, except that commercially available 1,4-bis(aminomethyl)cyclohexane (manufactured by Tokyo Chemical Industry Co., Ltd., trans isomer ratio 40 mol %) was used as an ingredient, and cyclohexane was used instead of heptane.

The reaction product liquid after filtering was analyzed, and it was found that the yield of 1,4-bis(aminomethyl)cyclohexane was 90%, and its trans isomer ratio was 80 mol %. It was also found that 1.06 mass % of 3-azabicyclo[3.2.2]nonane relative to a total amount of 1,4-bis(aminomethyl)cyclohexane and 3-azabicyclo[3.2.2]nonane was contained as by-products.

From the produced filtrate, the cyclohexane solvent was removed by vacuum single evaporation. Thereafter, the reaction product liquid from which the solvent was removed was added to a four-neck flask to which a packed column (filler: HELI PACK, the number of theoretical plates: 5 stages) was set and the reaction product liquid was rectified.

The rectifying conditions are as follows: a column top pressure of 4 kPa, a column bottom pressure of 5 kPa, a reflux ratio of 4, a column top temperature of 135 to 136° C., and a column bottom temperature (tank temperature) of 145 to 160° C. A fraction having a distillation rate of 0 mass % to 86 mass % relative to the charged mass was collected, thereby producing 1,4-BAC (D). As a result of analysis using a gas chromatograph, it was found that the 1,4-bis(aminomethyl)cyclohexane had a trans isomer ratio of 82 mol %, and contained, as impurity, 1.23 mass % of 3-azabicyclo[3.2.2]nonane relative to a total amount of 1,4-bis(aminomethyl)cyclohexane and 3-azabicyclo[3.2.2]nonane.

Production Example 5

Preparation of 1,4-BAC (E)

Reaction was carried out in the same manner as in Production Example 3, except that the 5 mass % ruthenium/alumina manufactured by Degussa was used instead of 5 mass % ruthenium/alumina manufactured by N.E. Chemcat.

The reaction product liquid after filtering was analyzed, and it was found that the yield of 1,4-bis(aminomethyl)cyclohexane was 98%, and its trans isomer ratio was 71 mol %. It was also found that 0.47 mass % of 3-azabicyclo[3.2.2]nonane relative to a total amount of 1,4-bis(aminomethyl)cyclohexane and 3-azabicyclo[3.2.2]nonane was contained as by-products.

From the produced filtrate, the cyclohexane solvent was removed by vacuum single evaporation. Thereafter, the reaction product liquid from which the solvent was removed was added to a four-neck flask to which a packed column (filler: HELI PACK, the number of theoretical plates: 5 stages) was set and the reaction product liquid was rectified.

The rectifying conditions are as follows: a column top pressure of 4 kPa, a column bottom pressure of 5 kPa, a reflux ratio of 1, a column top temperature of 135 to 136° C., and a column bottom temperature (tank temperature) of 145 to 160° C. A fraction having a distillation rate of 0 mass % to 95 mass % relative to the charged mass was collected, thereby producing 1,4-BAC (E). As a result of analysis using a gas chromatograph, it was found that the 1,4-bis(aminomethyl)cyclohexane had a trans isomer ratio of 72 mol %, and contained, as impurity, 0.49 mass % of 3-azabicyclo[3.2.2]nonane relative to a total amount of 1,4-bis(aminomethyl)cyclohexane and 3-azabicyclo[3.2.2]nonane.

Production Example 6

Preparation of 1,4-BAC (F)

Reaction was carried out in the same manner as in Production Example 3, except that 1,4-BAC (A) produced in Production Example 1 (trans isomer ratio 54 mol %) was used as an ingredient, 0.8 parts by mass of 5 mass % ruthenium/alumina was used, and the reaction time was set to 3 hours.

The reaction product liquid after filtering was analyzed, and it was found that the yield of 1,4-bis(aminomethyl)cyclohexane was 89%, and its trans isomer ratio was 71 mol %. It was also found that 1.10 mass % of 3-azabicyclo[3.2.2]nonane relative to a total amount of 1,4-bis(aminomethyl)cyclohexane and 3-azabicyclo[3.2.2]nonane was contained as by-products.

From the produced filtrate, the cyclohexane solvent was removed by vacuum single evaporation. Thereafter, the reaction product liquid from which the solvent was removed was added to a four-neck flask to which a packed column (filler: HELI PACK, the number of theoretical plates: 5 stages) was set and the reaction product liquid was rectified.

The rectifying conditions are as follows: a column top pressure of 4 kPa, a column bottom pressure of 5 kPa, a reflux ratio of 1, a column top temperature of 135 to 136° C., and a column bottom temperature (tank temperature) of 145 to 160° C. A fraction having a distillation rate of 0 mass % to 84 mass % relative to the charged mass was collected, thereby producing 1,4-BAC (F). As a result of analysis using a gas chromatograph, it was found that the 1,4-bis(aminomethyl)cyclohexane had a trans isomer ratio of 72 mol %, and contained, as impurity, 1.31 mass % of 3-azabicyclo[3.2.2]nonane relative to a total amount of 1,4-bis(aminomethyl)cyclohexane and 3-azabicyclo[3.2.2]nonane.

Production Example 7

Preparation of 1,4-BAC (G)

From the filtrate produced in the same manner as in Production Example 2, the heptane solvent was removed by vacuum single evaporation. Thereafter, the reaction product liquid from which the solvent was removed was added to a four-neck flask to which a packed column (filler: HELI PACK, the number of theoretical plates: 25 stages) was set and the reaction product liquid was rectified.

The rectifying conditions are as follows: a column top pressure of 4 kPa, a column bottom pressure of 5 kPa, a reflux ratio of 8, a column top temperature of 135 to 136° C., and a column bottom temperature (tank temperature) of 145 to 160° C. A fraction having a distillation rate of 0 mass % to 77 mass % relative to the charged mass was collected, thereby producing 1,4-BAC (G). As a result of analysis using a gas chromatograph, it was found that the 1,4-bis(aminomethyl)cyclohexane had a trans isomer ratio of 93 mol %, and contained, as impurity, 0.69 mass % of 3-azabicyclo[3.2.2]nonane relative to a total amount of 1,4-bis(aminomethyl)cyclohexane and 3-azabicyclo[3.2.2]nonane.

Production Example 8

Preparation of 1,4-BAC (H)

From the filtrate produced in the same manner as in Production Example 4, the cyclohexane solvent was removed by vacuum single evaporation. Thereafter, the reaction product liquid from which the solvent was removed was added to a four-neck flask to which a packed column (filler: HELI PACK, the number of theoretical plates: 25 stages) was set and the reaction product liquid was rectified.

The rectifying conditions are as follows: a column top pressure of 4 kPa, a column bottom pressure of 5 kPa, a reflux ratio of 8, a column top temperature of 135 to 136° C., and a column bottom temperature (tank temperature) of 145 to 160° C. A fraction having a distillation rate of 0 mass % to 77 mass % relative to the charged mass was collected, thereby producing 1,4-BAC (H). As a result of analysis using a gas chromatograph, it was found that the 1,4-bis(aminomethyl)cyclohexane had a trans isomer ratio of 93 mol %, and contained, as impurity, 1.38 mass % of 3-azabicyclo[3.2.2]nonane relative to a total amount of 1,4-bis(aminomethyl)cyclohexane and 3-azabicyclo[3.2.2]nonane.

Production Example 9

Preparation of 1,4-BAC (I)

A stainless steel-made reactor equipped with a stirrer, a thermometer, and a gas inlet tube was charged with 100 parts by mass of commercially available 1,4-bis(aminomethyl)cyclohexane (manufactured by Tokyo Chemical Industry Co., Ltd., trans isomer ratio 40 mol %), 1.7 parts by mass of a catalyst (ruthenium hydroxide (contains water, ruthenium content 13 mass %, prepared from alkaline hydrolysis of ruthenium chloride)), and 100 parts by mass of cyclohexane. After the inside of the reactor was replaced with hydrogen, the total pressure was rendered 5 MPa (gauge pressure) with hydrogen, and the mixture was heated to 190° C. and allowed to react for 5 hours while stirring at 400 rpm.

After completion of reaction, the temperature was reduced to room temperature, and the reaction product liquid was taken out. Filtering was performed to remove the catalyst.

The filtrate was analyzed, and it was found that the yield of 1,4-bis(aminomethyl)cyclohexane was 94%, and its trans isomer ratio was 66 mol %. It was also found that 0.5 mass % of 3-azabicyclo[3.2.2]nonane relative to a total amount of 1,4-bis(aminomethyl)cyclohexane and 3-azabicyclo[3.2.2]nonane was contained as by-products.

From the produced filtrate, the cyclohexane solvent was removed by vacuum single evaporation. Thereafter, the reaction product liquid from which the solvent was removed was added to a four-neck flask to which a packed column (filler: HELI PACK, the number of theoretical plates: 5 stages) was set and the reaction product liquid was rectified.

The rectifying conditions are as follows: a column top pressure of 4 kPa, a column bottom pressure of 5 kPa, a reflux ratio of 1, a column top temperature of 135 to 136° C., and a column bottom temperature (tank temperature) of 145 to 160° C. A fraction having a distillation rate of 0 mass % to 88 mass % relative to the charged mass was collected, thereby producing 1,4-BAC (1). As a result of analysis using a gas chromatograph, it was found that the 1,4-bis(aminomethyl)cyclohexane had a trans isomer ratio of 67 mol %, and contained, as impurity, 0.57 mass % of 3-azabicyclo[3.2.2]nonane relative to a total amount of 1,4-bis(aminomethyl)cyclohexane and 3-azabicyclo[3.2.2]nonane.

Production Example 10

Preparation of 1,4-BAC (J)

From the filtrate produced in the same manner as in Production Example 2, the heptane solvent was removed by vacuum single evaporation. Thereafter, the reaction product liquid from which the solvent was removed was added to a four-neck flask to which a packed column (filler: HELI PACK, the number of theoretical plates: 25 stages) was set and the reaction product liquid was rectified.

The rectifying conditions are as follows: a column top pressure of 4 kPa, a column bottom pressure of 5 kPa, a reflux ratio of 8, a column top temperature of 135 to 136° C., and a column bottom temperature (tank temperature) of 145 to 160° C. A fraction having a distillation rate of 0 mass % to 67 mass % relative to the charged mass was collected, thereby producing 1,4-BAC (J). As a result of analysis using a gas chromatograph, it was found that the 1,4-bis(aminomethyl)cyclohexane had a trans isomer ratio of 97 mol %, and contained, as impurity, 0.80 mass % of 3-azabicyclo[3.2.2]nonane relative to a total amount of 1,4-bis(aminomethyl)cyclohexane and 3-azabicyclo[3.2.2]nonane.

<Analysis Conditions 1 (Analysis in Production Examples)>

Analysis conditions for the filtrate produced in the isomerization reaction, the trans isomer ratio in 1,4-BAC, and the 3-azabicyclo[3.2.2]nonane content are shown below.

Analysis device: manufactured by SHIMADZU CORPORATION GC-2010
Column: VARIAN CP-SIL 8 CB FOR AMINES (length 30 m×internal diameter 0.25 mm, film thickness 0.25 μm)
Sample introduction portion temperature: 300° C.
Detection portion temperature: 300° C.
Column temperature pattern: kept for 10 minutes at 130° C., temperature increased at 10° C./min from 130° C. to 300° C., and kept at 300° C. for 6 minutes
Column pressure: 140 kPa
Split ratio: 50/1
Detection method: FID
Sample: 0.2 g of analysis target dissolved in 50 mL of methanol The trans isomer ratio and the 3-azabicyclo[3.2.2]nonane content were determined based on the following formulas.

$$\text{Trans isomer ratio (mol \%)} = \text{trans isomer yield}/(\text{trans isomer yield} + \text{cis isomer yield}) \times 100$$

$$3\text{-}Azabicyclo[3.2.2]nonane \text{ content (mass \%)} = 3\text{-}azabicyclo[3.2.2]nonane\ GC\ \text{area}/(1,4\text{-}BAC\ GC\ \text{area} + 3\text{-}azabicyclo[3.2.2]nonane\ GC\ \text{area}) \times 100$$

The isomerization conditions, the rectifying conditions, and the results are shown in Table 1.

TABLE 1

| | | | Production Ex. 1 | Production Ex. 2 | Production Ex. 3 | Production Ex. 4 | Production Ex. 5 | Production Ex. 6 |
|---|---|---|---|---|---|---|---|---|
| 1,4-BAC Isomerization Conditions | Amine material | Type | A — | B 1,4-BAC(A) | C 1,4-BAC(A) | D Commercially available product(t-40) | E 1,4-BAC(A) | F 1,4-BAC(A) |
| | | Trans isomer ratio (mol %) | | 54 | 54 | 40 | 54 | 54 |
| | Amine charged | parts by mass | | 100 | 100 | 100 | 100 | 100 |
| | Reaction time | hr | | 3 | 2 | 3 | 2 | 3 |
| | Reaction temperature | ° C. | | 210 | 210 | 210 | 210 | 210 |
| | Reaction pressure | MPa | | 5 | 5 | 5 | 5 | 5 |
| | Solvent | | | Heptane | Cyclohexane | Cyclohexane | Cyclohexane | Cyclohexane |
| | Solvent charged | parts by mass | | 100 | 100 | 100 | 100 | 100 |
| | Catalyst | | | 5 mass % Ru/alumina N.E.Chemcat | 5 mass % Ru/alumina N.E.Chemcat | 5 mass % Ru/alumina N.E.Chemcat | 5 mass % Ru/alumina Degussa | mass % Ru/alumina N.E.Chemcat |
| | Catalyst charged | parts by mass | | 1.6 | 1.5 | 1.6 | 1.5 | 0.8 |
| Isomerization results | 1,4-BAC yield | mol % | 93 | 92 | 93 | 90 | 98 | 89 |
| | Trans isomer ratio | mol % | 54 | 79 | 81 | 80 | 71 | 71 |
| | 3-azabicyclo[3.2.2]nonane content | mass % | — | 0.53 | 0.43 | 1.06 | 0.47 | 1.10 |
| Rectification Conditions | Number of stages | | — | 5 | 5 | 5 | 5 | 5 |
| | Reflux ratio | | | 4 | 1 | 4 | 1 | 1 |
| | Distillation rate | mass % | | 0-87 | 0-91 | 0-86 | 0-95 | 0-84 |
| Rectification Results | Trans isomer ratio | mol % | | 82 | 82 | 82 | 72 | 72 |
| | 3-azabicyclo[3.2.2]nonane content | mass % | | 0.61 | 0.48 | 1.23 | 0.49 | 1.31 |

| | | | Production Ex. 7 | Production Ex. 8 | Production Ex. 9 | Production Ex. 10 |
|---|---|---|---|---|---|---|
| 1,4-BAC Isomerization Conditions | Amine material | Type | G 1,4-BAC(A) | H Commercially available product(t-40) | I Commercially available product(t-40) | J 1,4-BAC(A) |
| | | Trans isomer ratio (mol %) | 54 | 40 | 40 | 54 |

TABLE 1-continued

|  |  |  |  |  |  |  |
|---|---|---|---|---|---|---|
|  | Amine charged | parts by mass | 100 | 100 | 100 | 100 |
|  | Reaction time | hr | 3 | 3 | 5 | 3 |
|  | Reaction temperature | ° C. | 210 | 210 | 190 | 210 |
|  | Reaction pressure | MPa | 5 | 5 | 5 | 5 |
|  | Solvent |  | Heptane | Cyclohexane | Cyclohexane | Heptane |
|  | Solvent charged | parts by mass | 100 | 100 | 100 | 100 |
|  | Catalyst |  | 5 mass % Ru/alumina N.E.Chemcat | 5 mass % Ru/alumina N.E.Chemcat | Ru(OH)₃ Preparation product | 5 mass % Ru/alumina N.E.Chemcat |
|  | Catalyst charged | parts by mass | 1.6 | 1.6 | 1.7 | 1.6 |
| Isomerization results | 1,4-BAC yield | mol % | 92 | 90 | 94 | 92 |
|  | Trans isomer ratio | mol % | 79 | 80 | 66 | 79 |
|  | 3-azabicyclo[3.2.2]nonane content | mass % | 0.53 | 1.06 | 0.50 | 0.53 |
| Rectification Conditions | Number of stages |  | 25 | 25 | 5 | 25 |
|  | Reflux ratio |  | 8 | 8 | 1 | 8 |
|  | Distillation rate | mass % | 0-77 | 0-77 | 0-88 | 0-67 |
| Rectification Results | Trans isomer ratio | mol % | 93 | 93 | 67 | 97 |
|  | 3-azabicyclo[3.2.2]nonane content | mass % | 0.69 | 1.38 | 0.57 | 0.8 |

Analysis Example

A commercially available 1,4-bis(aminomethyl)cyclohexane (product of Tokyo Chemical Industry Co., Ltd.) was analyzed with the above-described conditions, and it was found that the trans isomer ratio was 40 mol %, and the 3-azabicyclo[3.2.2]nonane was less than the detection limit (0.03 ppm).

Preparation of 1,4-bis(isocyanatomethyl)cyclohexane

Example 1

Synthesis of 1,4-BIC (A)

A stainless steel-made reactor equipped with a stirrer, a thermometer, a nitrogen inlet tube, a chlorine gas inlet tube, a phosgene inlet tube, a gas discharge pipe, a gas cooling device, and an automatic pressure regulating valve was charged with 55 parts by mass of 1,4-BAC (B) produced in Production Example 2 and 700 parts by mass of orthodichlorobenzene. The mixture was heated to 60° C. while stirring at 300 rpm. Thereafter, hydrochloric acid gas was introduced at a flow rate of 1.0 mol/hr (relative to 1,4-BAC), in an amount 3.0 mol times larger relative to 1,4-BAC. Cold water was allowed to go through the reactor jacket, keeping the internal temperature to 60 to 100° C.

Then, 77 parts by mass of phosgene was added thereto, and the pressure was increased to 0.2 MPa (gauge pressure) while increasing the temperature of the reaction solution to 150° C. The mixture was allowed to react for 6 hours while further adding phosgene under a pressure of 0.2 MPa (gauge pressure) and at a reaction temperature of 150° C. The amount of the phosgene added during the reaction was 230 parts by mass.

After completion of reaction, nitrogen gas was allowed to pass through at 100 to 150° C., and degassing was performed. Then, after distilling the solvent orthodichlorobenzene under reduced pressure, 1,4-bis(isocyanatomethyl)cyclohexane was distilled also under reduced pressure.

Then, the distilled 1,4-bis(isocyanatomethyl)cyclohexane was introduced into a reactor equipped with a stirrer, a thermometer, a reflux tube, and a nitrogen inlet tube, and heated to 190° C. for 4 hours under normal pressure while introducing nitrogen.

Then, a flask to which a packed column (filler: HELI PACK, the number of theoretical plates: 10 stages) was set was charged with the 1,4-bis(isocyanatomethyl)cyclohexane after the heat treatment, and the 1,4-bis(isocyanatomethyl)cyclohexane was rectified.

The rectifying conditions are as follows: a column top pressure of 0.3 to 1.3 kPa, a reflux ratio of 1, a column top temperature of 120 to 1.45° C., a column bottom temperature (tank temperature) of 160 to 170° C., and a column bottom residence time of 4 hours. A fraction having a distillation rate of 10 mass % to 95 mass % relative to the charged mass was collected, thereby producing 1,4-BIC (A).

The gas chromatography measurement revealed that the produced 1,4-BIC (A) had a purity of 99.8%, a trans isomer ratio of 82 mol %, and a concentration of the above-described compound represented by formula (1) of 1.5 ppm. The analysis conditions are to be described later (the same applies in the following).

Example 2

Synthesis of 1,4-BIC (B)

1,4-BIC (B) was produced in the same manner as in Example 1, except that 1,4-BAC (C) prepared in Production Example 3 was used instead of 1,4-BAC (B), and the heating before rectification was conducted to 190° C. for 8 hours. The gas chromatography measurement revealed that the produced 1,4-BIC (B) had a purity of 99.8%, a trans isomer ratio of 82 mol %, and a concentration of the above-described compound represented by formula (1) of 0.19 ppm.

Example 3

Synthesis of 1,4-BIC (C)

1,4-BIC (C) was produced in the same manner as in Example 1, except that 1,4-BAC (D) prepared in Production Example 4 was used instead of 1,4-BAC (B), and the heating before rectification was conducted to 190° C. for 2 hours. The gas chromatography measurement revealed that the produced 1,4-BIC (C) had a purity of 99.7%, a trans isomer ratio of 82 mol %, and a concentration of the above-described compound represented by formula (1) of 270 ppm.

Example 4

Synthesis of 1,4-BIC (D)

1,4-BIC (D) was produced in the same manner as in Example 1, except that 1,4-BAC (E) prepared in Production Example 5 was used instead of 1,4-BAC (B). The gas chromatography measurement revealed that the produced 1,4-BIC (D) had a purity of 99.8%, a trans isomer ratio of 72 mol %, and a concentration of the above-described compound represented by formula (1) of 12 ppm.

Example 5

Synthesis of 1,4-BIC (E)

1,4-BIC (E) was produced in the same manner as in Example 4, except that the heating before rectification was conducted to 190° C. for 8 hours. The gas chromatography measurement revealed that the produced 1,4-BIC (E) had a purity of 99.8%, a trans isomer ratio of 72 mol %, and a concentration of the above-described compound represented by formula (1) of 0.15 ppm.

Example 6

Synthesis of 1,4-BIC (F)

1,4-BIC (F) was produced in the same manner as in Example 4, except that 1,4-BAC (F) prepared in Production Example 6 was used instead of 1,4-BAC (E), and the heating before rectification was conducted to 190° C. for 2 hours. The gas chromatography measurement revealed that the produced 1,4-BIC (F) had a purity of 99.7%, a trans isomer ratio of 72 mol %, and a concentration of the above-described compound represented by formula (1) of 250 ppm.

Example 7

Synthesis of 1,4-BIC (G)

1,4-BIC (G) was produced in the same manner as in Example 1, except that 1,4-BAC (G) prepared in Production Example 7 was used instead of 1,4-BAC (B). The gas chromatography measurement revealed that the produced 1,4-BIC (G) had a purity of 99.7%, a trans isomer ratio of 93 mol %, and a concentration of the above-described compound represented by formula (1) of 20 ppm.

Example 8

Synthesis of 1,4-BIC (H)

1,4-BIC (H) was produced in the same manner as in Example 7, except that the heating before rectification was conducted to 190° C. for 8 hours. The gas chromatography measurement revealed that the produced 1,4-BIC (H) had a purity of 99.7%, a trans isomer ratio of 93 mol %, and a concentration of the above-described compound represented by formula (1) of 0.22 ppm.

Example 9

Synthesis of 1,4-BIC (I)

1,4-BIC (I) was produced in the same manner as in Example 7, except that 1,4-BAC (H) prepared in Production Example 8 was used instead of 1,4-BAC (G), and the heating before rectification was conducted to 190° C. for 3 hours. The gas chromatography measurement revealed that the produced 1,4-BIC (I) had a purity of 99.7%, a trans isomer ratio of 93 mol %, and a concentration of the above-described compound represented by formula (1) of 285 ppm.

Comparative Example 1

Synthesis of 1,4-BIC (J)

1,4-BIC (J) was produced in the same manner as in Example 1, except that for the 1,4-bis(isocyanatomethyl) cyclohexane rectification fi-action, a fraction having a distillation rate of 80 mass % to 90 mass % relative to the charged mass was collected. The gas chromatography measurement revealed that the produced 1,4-BIC (J) had a purity of 99.8%, a trans isomer ratio of 82 mol %, and the above-described compound represented by formula (1) could not be detected (less than the detection limit of 0.03 ppm (the same applies in the following)).

Comparative Example 2

Synthesis of 1,4-BIC (K)

1,4-BIC (K) was produced in the same manner as in Example 1, except that the heating before rectification was conducted to 190° C. for 12 hours. The gas chromatography measurement revealed that the produced 1,4-BIC (K) had a purity of 99.8%, a trans isomer ratio of 82 mol %, and a concentration of the above-described compound represented by formula (1) of 0.07 ppm.

Comparative Example 3

Synthesis of 1,4-BIC (L)

1,4-BIC (L) was produced in the same manner as in Example 3, except that the heating was not conducted before the rectification. The gas chromatography measurement revealed that the produced 1,4-BIC (L) had a purity of 99.8%, a trans isomer ratio of 82 mol %, and a concentration of the above-described compound represented by formula (1) of 340 ppm.

Comparative Example 4

Synthesis of 1,4-BIC (M)

1,4-BIC (M) was produced in the same manner as in Example 5, except that for the 1,4-bis(isocyanatomethyl) cyclohexane rectification fraction, a fraction having a distillation rate of 80 mass % to 90 mass % relative to the charged mass was collected. The gas chromatography measurement revealed that the produced 1,4-BIC (M) had a purity of 99.8%, a trans isomer ratio of 71 mol %, and the above-described compound represented by formula (1) could not be detected.

Comparative Example 5

Synthesis of 1,4-BIC (N)

1,4-BIC (N) was produced in the same manner as in Example 4, except that the heating before rectification was conducted to 190° C. for 12 hours. The gas chromatography measurement revealed that the produced 1,4-BIC (N) had a purity of 99.8%, a trans isomer ratio of 71 mol %, and a concentration of the above-described compound represented by formula (1) of 0.07 ppm.

Comparative Example 6

Synthesis of 1,4-BIC(O)

1,4-BIC(O) was produced in the same manner as in Example 6, except that the heating was not conducted before rectification. The gas chromatography measurement revealed that the produced 1,4-BIC(O) had a purity of 99.8%, a trans isomer ratio of 71 mol %, and a concentration of the above-described compound represented by formula (1) of 340 ppm.

Comparative Example 7

Synthesis of 1,4-BIC (P)

1,4-BIC (P) was produced in the same manner as in Example 8, except that for the 1,4-bis(isocyanatomethyl)cyclohexane rectification fraction, a fraction having a distillation rate of 80 mass % to 90 mass % relative to the charged mass was collected. The gas chromatography measurement revealed that the produced 1,4-BIC (P) had a purity of 99.7%, a trans isomer ratio of 93 mol %, and the above-described compound represented by formula (1) could not be detected.

Comparative Example 8

Synthesis of 1,4-BIC (Q)

1,4-BIC (Q) was produced in the same manner as in Example 7, except that the heating before rectification was conducted to 190° C. for 12 hours. The gas chromatography measurement revealed that the produced 1,4-BIC (Q) had a purity of 99.7%, a trans isomer ratio of 93 mol %, and a concentration of the above-described compound represented by formula (1) of 0.07 ppm.

Comparative Example 9

Synthesis of 1,4-BIC (R)9

1,4-BIC (R) was produced in the same manner as in Example 7, except that the heating was not conducted before rectification. The gas chromatography measurement revealed that the produced 1,4-BIC (R) had a purity of 99.8%, a trans isomer ratio of 93 mol %, and a concentration of the above-described compound represented by formula (1) of 380 ppm.

Comparative Example 10

Synthesis of 1,4-BIC (S)

1,4-BIC (S) was produced in the same manner as in Example 1, except that 1,4-BAC (I) prepared in Production Example 9 was used instead of 1,4-BAC (B). The gas chromatography measurement revealed that the produced 1,4-BIC (S) had a purity of 99.8%, a trans isomer ratio of 67 mol %, and a concentration of the above-described compound represented by formula (1) of 12 ppm.

Comparative Example 11

Synthesis of 1,4-BIC (T)

1,4-BIC (T) was produced in the same manner as in Example 1, except that 1,4-BAC (J) prepared in Production Example 10 was used instead of 1,4-BAC (B). The gas chromatography measurement revealed that the produced 1,4-BIC (T) had a purity of 99.5%, a trans isomer ratio of 97 mol %, and a concentration of the above-described compound represented by formula (1) of 18 ppm.

Reference Comparative Example 1

Synthesis of 1,4-BIC (U)

1,4-BIC (U) was produced in the same manner as in Example 1, except that commercially available 1,4-bis(aminomethyl)cyclohexane (product of Tokyo Chemical industry Co., Ltd., trans isomer ratio 40 mol %) was used instead of 1,4-BAC (B). The gas chromatography measurement revealed that the produced 1,4-BIC (T) had a purity of 99.7%, a trans isomer ratio of 40 mol %, and the above-described compound represented by formula (1) of less than the detection limit (0.03 ppm).

<Analysis Conditions 2 (Identification of the Above-Described Compound Represented by Formula (1))>

Based on the CI mass spectrum and FD mass spectrum of GC-MS analysis, and NMR spectrum and NMR two dimensional measurement (Hetero-nuclear Multiple-Bond Connectivity: HMBC) below, the substance contained in 1,4-BIC was identified as the above-described compound represented by formula (1).

To be specific, first, the substance contained in 1,4-BIC produced in the above-described Production Example was analyzed based on the CI mass spectrum and FD mass spectrum of GC-MS analysis, and NMR spectrum, and NMR two dimensional measurement. The measurement results are shown in FIGS. 1 to 4.

[CI Mass Spectrum Measurement Conditions]
  Device: Q1000GC K9 (manufactured by JEOL Ltd.)
  Column: DB-5MS+DG 30 m*25 mm*0.25 μm (DG10 m)
  Oven temperature: 40° C. (held for 4 minutes)→temperature increased at 10° C./min→300° C. (held for 10 minutes)
  Injection temperature: 300° C., interface temperature; 280° C.
  Split mode: 200/1, 20/1
  He: 1.0 ml/min, ionization mode CI (reagent gas, isobutane)
  Mass Range: 60-800
[FD Mass Spectrum Measurement Conditions]
  Device; JMS-T 100GC (manufactured by JEOL Ltd.)
  Ionization mode: FD method
  Measurement range: m/z 10 to 2000
  Cathode: −10 kV
  Emitter electric current: 0 mA→51.2 mA/min→42 mA
  Spectrum recording interval: 0.40 s
[NMR Measurement Conditions]
  NMR measurement apparatus: AVANCEIII500 magnetic resonance instruments (CryoProbe Prodigy) manufactured by Bruker BioSpin K.K.
  Sample concentration: ca. 50 mg/0.6 mL
  Measurement solvent: $CDCl_3$
  Measurement temperature: 25° C.
  $^1$H-NMR
  Measurement nuclear: $^1$H (500 MHz)
  Measurement mode: single pulse Pulse width: 45° (6.0 g sec)
Points: 32 k
Observation range: 20 ppm (−5 to 15 ppm)
Repetition time: 7 seconds
Total times: 64
Window function: exponential (BF: 0.15 Hz)
Chemical shift base: $CHCl_3$: 7.26 ppm
$^{13}C$-NMR
Measurement nuclear: $^{13}C$ (125 MHz)
Measurement mode: single pulse proton broadband decoupling
Pulse width: 45° C. (5.0 t sec)
Points: 64 k
Observation range: 250 ppm (−25 to 225 ppm)
Repetition time: 5.5 seconds
Total times: 256
Window function: exponential (BF: 1.0 Hz)
Chemical shift base: $CDCl_3$: 77.0 ppm
<Two-dimensional NMR> (HMBC method)
Observation range:
$^1H$: 10 ppm (0 to 10 ppm)
$^{13}C$: 140 ppm (20 to 160 ppm)
Total times: 32
Data size: 2K×1K (after zero filling)

Figure 2:
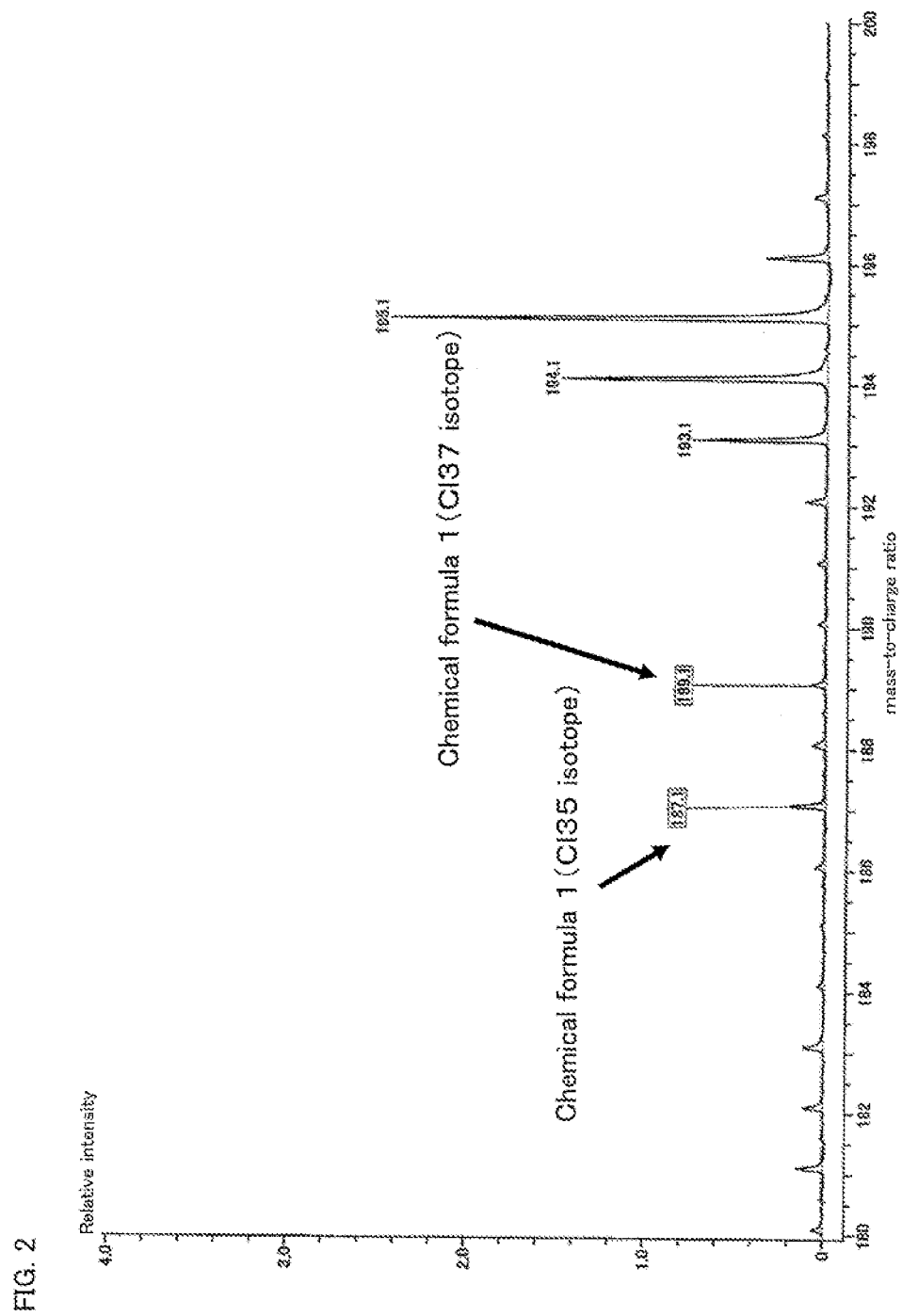
FIG. 2 shows a FD mass spectrum of 1,4-BIC containing a compound represented by formula (1).

Based on FIG. 2, a peak of 187.1 by mass (35Cl: isotope 35) derived from chemical formula (1) and 189.1 by mass (37Cl: isotope 37) and were confirmed.

Figure 3:
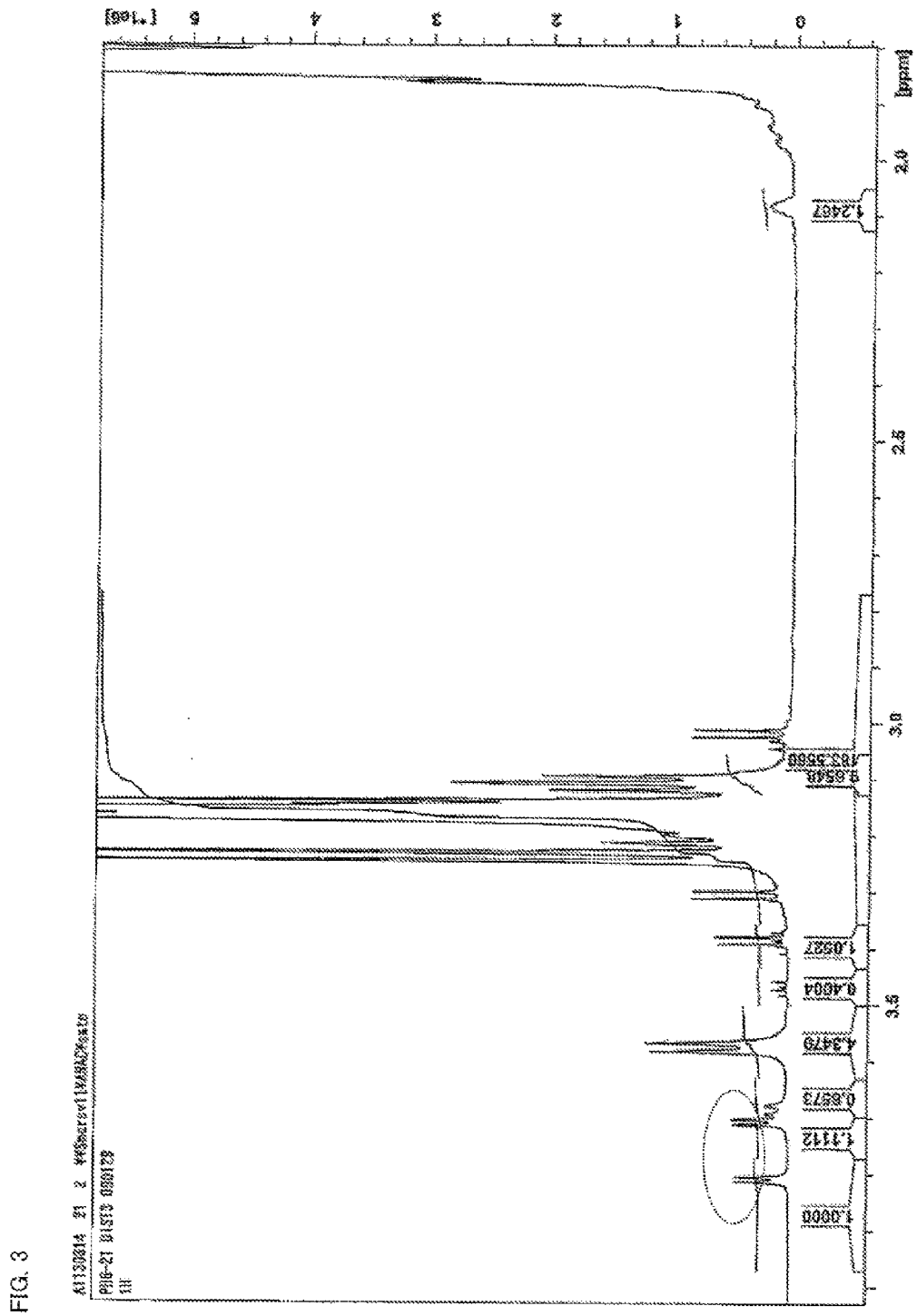
FIG. 3 shows a spectrum of $^1$H-NMR analysis on 1,4-BIC containing the compound represented by formula (1).

Furthermore, as shown in FIG. 3, chemical shifts in $^1H$-NMR of 3.71 ppm and 3.81 ppm were assigned to the signals (double lines) of protons derived from methylene adjacent to N atoms in the bicycle ring.

Figure 4:
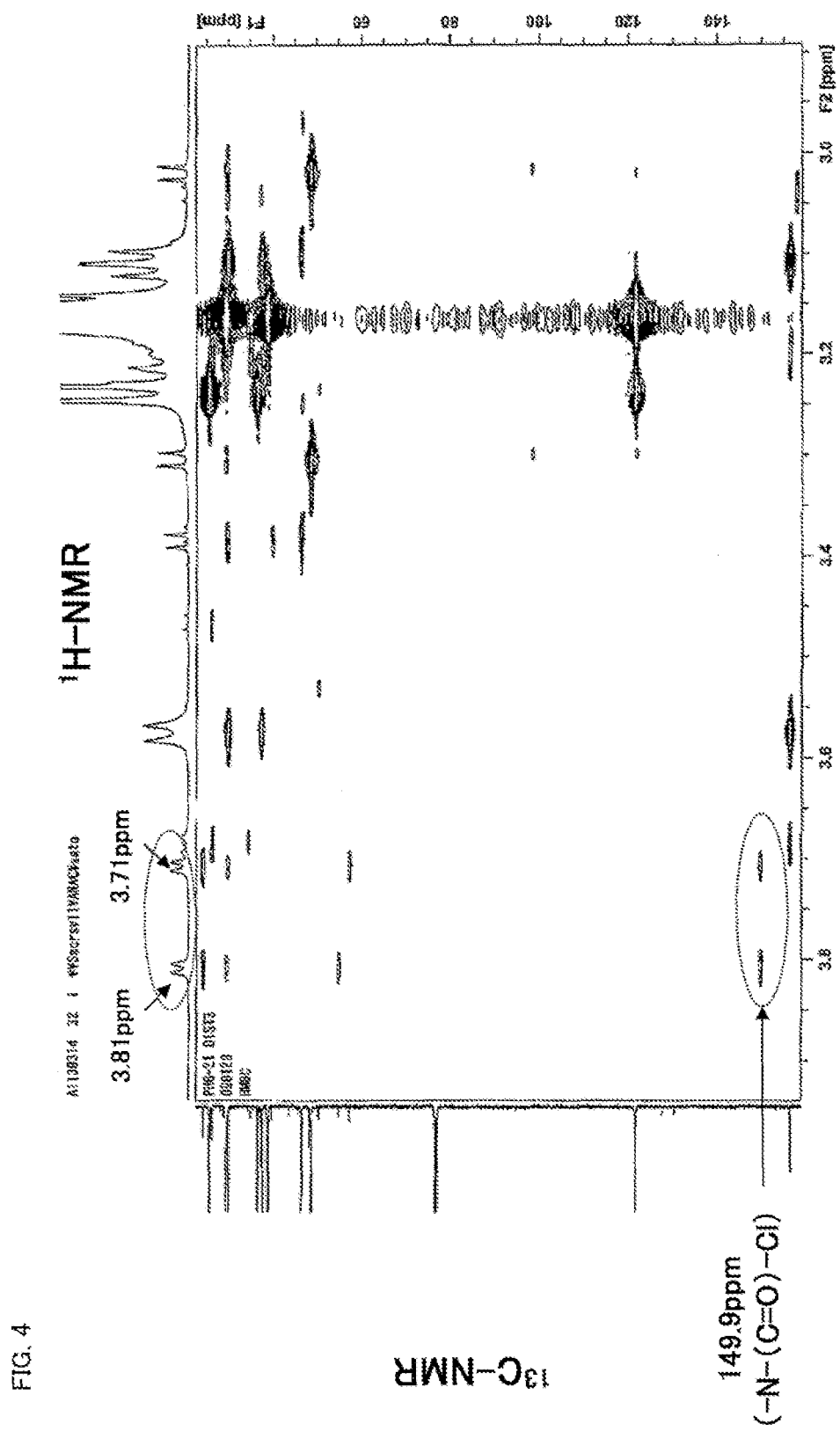
FIG. 4 shows measurement results of NMR two dimensional measurement (Hetero-nuclear Multiple-Bond Connectivity: HMBC) on 1,4-BIC containing the compound represented by formula (1).

Furthermore, as shown in FIG. 4, based on two-dimensional NMR (HMBC method), it was found that there are correlations between the chemical shifts 3.71 ppm and 3.81 ppm of the above-described $^1H$-NMR, and the chemical shift of 149.9 ppm $^{13}C$-NMR. The 149.9 ppm signal was assigned to be derived from carbon of —N—(C=O)—Cl.

Furthermore, compound represented by formula (1) was prepared in Preparation Examples 1 to 2 below.

Preparation Example 1

Preparation of Hydrochloride of Compound Represented by Formula (2) (3-azabicyclo[3.2.2]nonane)

A four-neck flask to which a packed column (filler: HELI PACK, the number of theoretical plates: 2 stages) was set was charged with 900 parts by mass (3-azabicyclo[3.2.2] nonane content 1.31 mass %) of 1,4-BAC (F) prepared in Production Example 6 and 2700 parts by mass of 1-octanol, and the mixture was rectified.

The rectifying conditions are as follows: a column top pressure of 4 to 5 torr, a column top temperature of 75 to 100° C., and a column bottom temperature (tank temperature) of 95 to 105° C. A fraction having a distillation rate of 0 mass % to 27 mass % relative to the charged mass was collected.

Extraction operation was conducted five times using 550 parts by mass of an aqueous solution of 1 mol % hydrochloric acid relative to 800 parts by mass of the fraction, and then thereafter, water was removed from the aqueous phase by evaporation with a jacket temperature of 90° C. and a degree of reduced pressure of 80 torr.

Thereafter, the residue on evaporation was filtered (filter paper: Kiriyama filter paper No4) with 100 parts by mass of toluene, and then thereafter, drying was performed under a nitrogen flow, thereby producing 6.5 parts by mass of 3-azabicyclo[3.2.2]nonane hydrochloride (hydrochloride of the compound of formula (2)).

The produced 3-azabicyclo[3.2.2]nonane hydrochloride solid had a purity of 99.1% (GC area %).

Preparation Example 2

Preparation of Compound Represented by Formula (1) (Carbamoyl Chloride of the 3-azabicyclo[3.2.2]nonane)

A flask equipped with a stirrer, a thermometer, a phosgene gas inlet tube, a nitrogen gas inlet tube, and a gas purge line was charged with 3.17 parts by mass of 3-azabicyclo[3.2.2] nonane hydrochloride (hydrochloride of compound of formula (2)) produced in Preparation Example 1 and 100 parts by mass of toluene.

After the temperature was increased to 70° C., 10.5 parts by mass of phosgene was fed at 7 parts by mass/hour. After the phosgene was fed, phosgene was removed at 70° C. for 3.5 hours with nitrogen gas, thereby producing 85 parts by mass of a reaction mass. The reaction mass was subjected to reduced pressure filtering with a 0.2 μm PTFE membrane filter, thereby removing insoluble solids.

Toluene was distilled off from the filtrate under reduced pressure, thereby producing 3.2 parts by mass of a compound represented by formula (1) (carbamoyl chloride of 3-azabicyclo[3.2.2]nonane).

The produced compound had appearance of white solid.

The compound produced in the above-described Preparation Example 2 was measured under the following conditions with $^1H$-NMR spectrum, $^{13}C$-NMR spectrum, IR spectrum, and GC-MS spectrum. The measurement results are shown in FIGS. 5 to 8.

[$^1H$-NMR Measurement Conditions]
NMR measurement apparatus: ECX-400P (400 MHz) manufactured by JEOL Ltd.
Sample concentration: 25 mg/0.6 mL
Sample solvent: $CDCl_3$
Scan: 16 times
[$^{13}C$-NMR Measurement Conditions]
NMR measurement apparatus: ECX-400P (400 MHz) manufactured by JEOL Ltd.
Sample solvent: $CDCl_3$
Sample concentration: 25 mg/0.6 mL
Scan: 5000 times
Measurement mode: BCM
[IR Measurement Conditions]
IR measurement apparatus: Perkin-Elmer Spectrum One FT-IR Spectrometer
Measurement method: ATR (reflection method)
Wave number range: 4000 to 400 $cm^{-1}$
Resolving power: 4 $cm^{-1}$
[GC-MS Measurement Conditions]
Device: Agilent 6890N/5973N MSD
Column: J&W DB-5MS (0.25 mmID×60 m, Film=0.25 μm)
Carrier gas: He (Constant flow mode: 1.5 mL/min)
Oven temperature: 80° C. (1 min)→10° C./min→250° C. (2 min)[Total=20 min]
Injection method: Split Method (Split ratio 50:1)
Injection inlet temperature: 250° C.
Interface temperature: 280° C.
Ion source temperature: 230° C.
Quadrupole temperature: 150° C.
Ionization method: EI method (ionization voltage: 70 eV)

Figure 5:
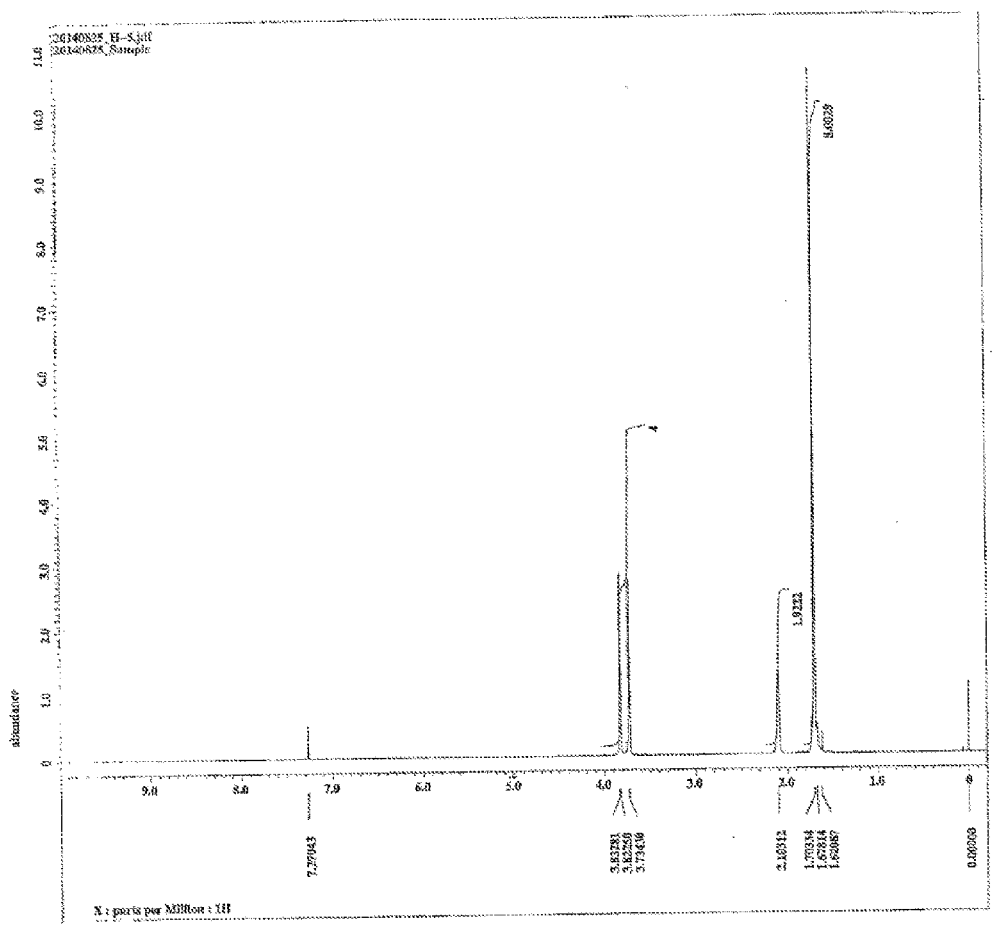
FIG. 5 shows a spectrum of $^1$H-NMR analysis on the compound represented by formula (1) produced in Preparation Example 2.

Detection method: Scanning method (90 to 500)
Injection amount: 1.0 μL
The peaks in the obtained spectrums are assigned. The results are shown below.
[$^1$H-NMR Assignment]
The assignments of $^1$H-NMR spectrum shown in FIG. 5 are shown below.

Chemical Formula 5

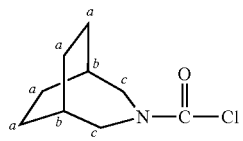

Figure 6:
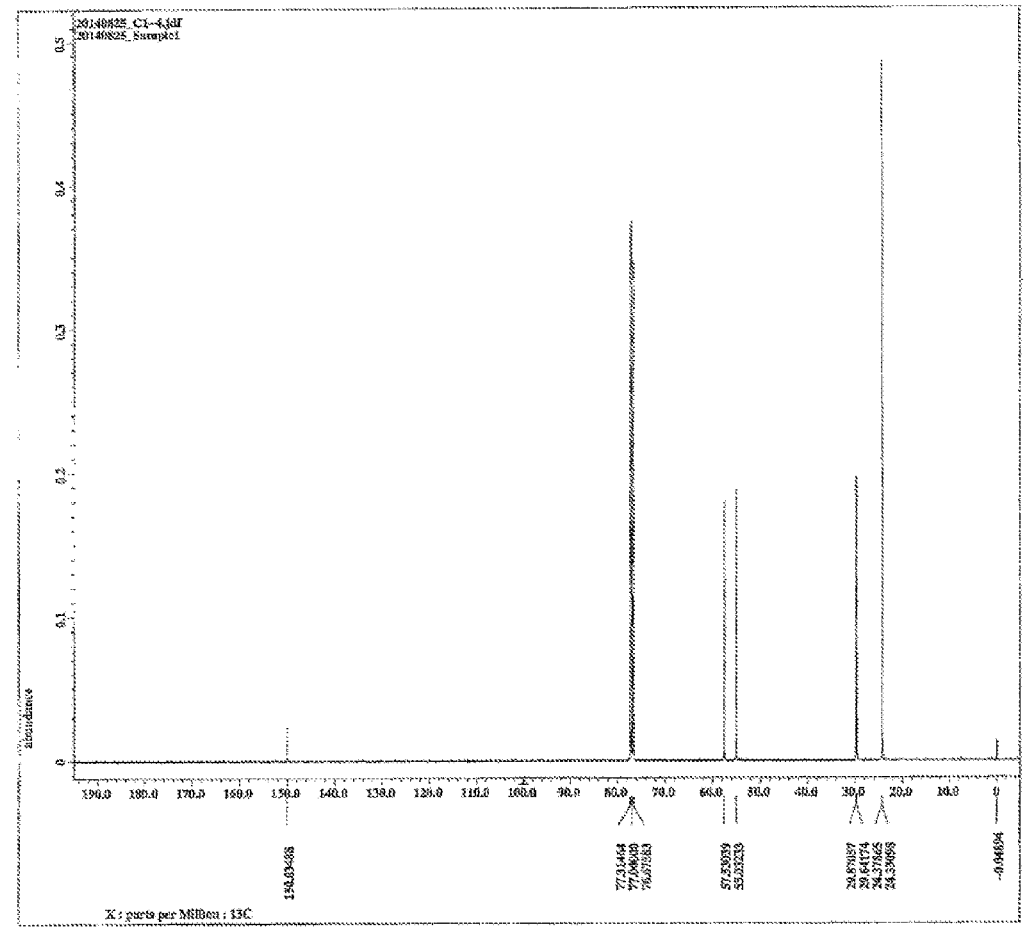
FIG. 6 shows a spectrum of $^{13}$C-NMR analysis on the compound represented by formula (1) produced in Preparation Example 2.

(1)

a (8H): 1.703 to 1.603 ppm integration ratio 8.0029
b (2H): 2.013 ppm integration ratio 1.9222
c (4H): 3.833 to 3.734 ppm integration ratio 4
(7.27 ppm is derived from chloroform in CDCl$_3$)
[$^{13}$C-NMR Assignment]
The assignments of $^{13}$C-NMR spectrum shown in FIG. 6 are shown below.

Chemical Formula 6

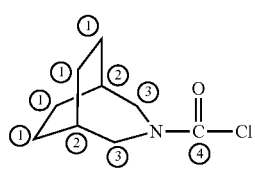

(1)

Figure 7:
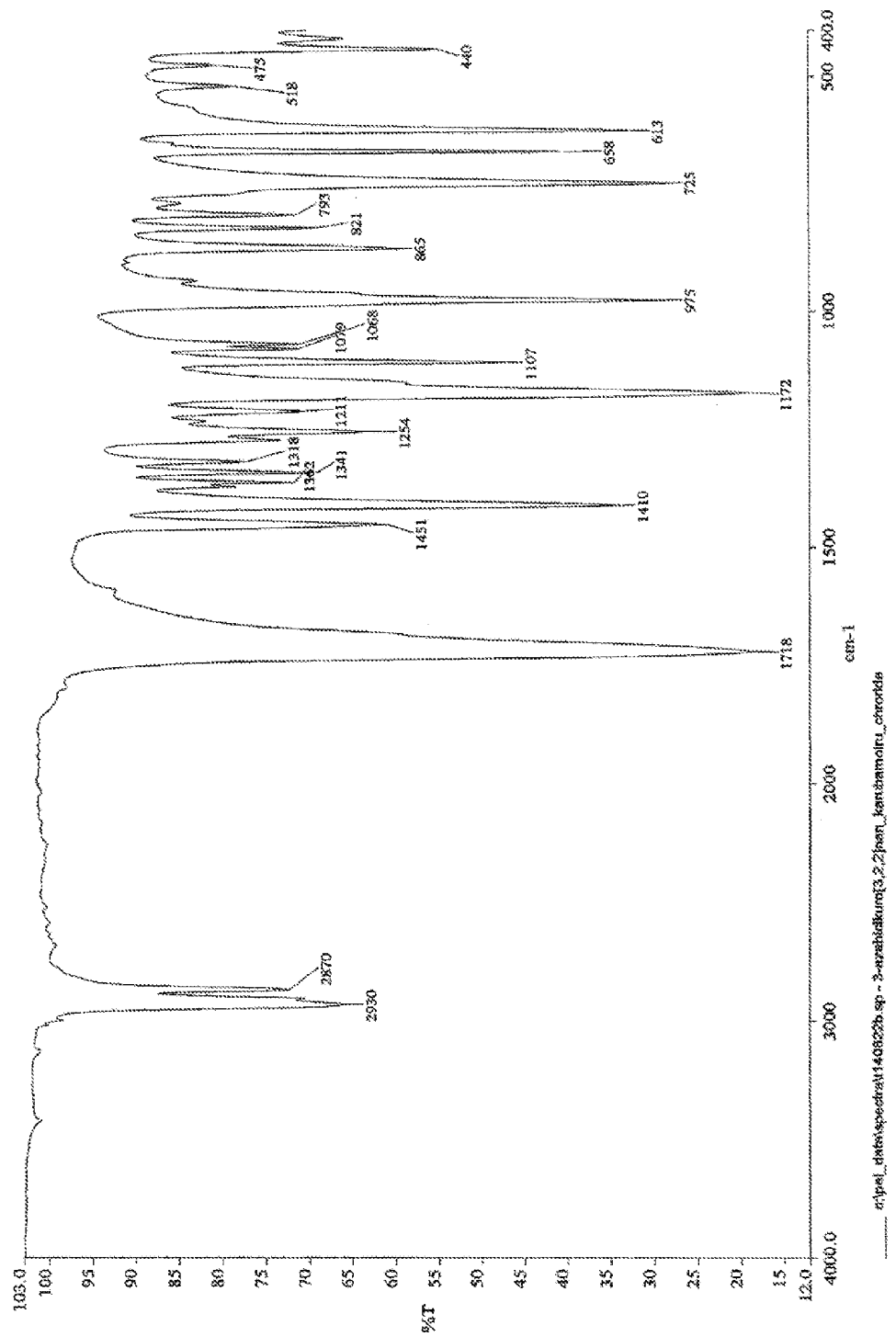
FIG. 7 shows an IR spectrum of the compound represented by formula (1) produced in Preparation Example 2.
Figure 8:
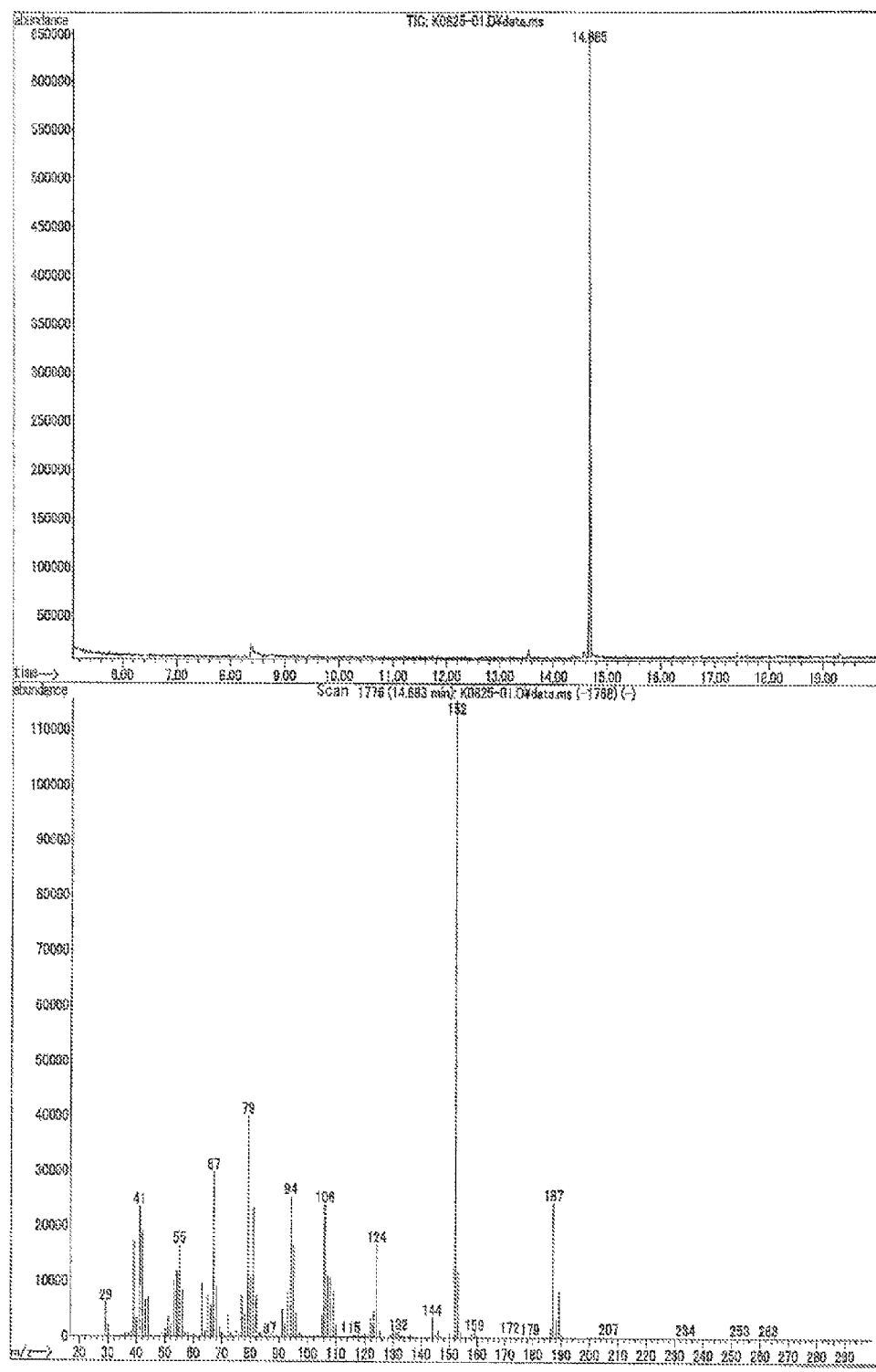
FIG. 8 shows a GC-MS spectrum of the compound represented by formula (1) produced in Preparation Example 2.

(1): 24.33 to 24.38 ppm
(2): 29.64 to 29.87 ppm
(3): 55.03 ppm, 57.53 ppm
(4): 150.03 ppm
(76.68 to 77.31 ppm is a peak derived from CDCl$_3$)
[Assignments in IR Spectrum]
In the IR spectrum shown in FIG. 7, absorption of vC=O is observed at 1718 cm$^{-1}$. No absorption (near 3400 cm$^{-1}$) of secondary amine (NH) was observed.
[Assignments in GC-MS Spectrum]
In the GC-MS spectrum shown in FIG. 8, MS molecule ion peak of 187 m/z and 189 m/z were observed with about 3:1 intensity ratio, and this was the intensity ratio characteristic of a chlorine-containing compound. It was also found that a peak of 152 m/z of a molecule ion from which a chlor group was eliminated was observed.

From these results, the substance contained in 1,4-BIC was identified as the compound having the structure of the above-described formula (1).
<Analysis Conditions 3 (1,4-BIC Purity and Analysis on the Above-Described Compound Represented by Formula (1))>
From the area value of the gas chromatogram obtained with the gas chromatograph analysis conditions shown below, 1,4-BIC purity (%) and the concentration (ppm) of the above-described compound represented by formula (1) were calculated.
Device; Q1000GC manufactured by JEOL Ltd.
Column; DB-5MS-+DG 30 m×0.25 mm×0.25 μm (DG10 m)
Oven temperature; kept for 4 minutes at 40° C., the temperature increased at 10° C./min from 40° C. to 300° C., and kept for 10 minutes at 300° C.
Injection inlet temperature; 300° C.
Detector temperature; 280° C.
Carrier Gas; helium gas (1.0 ml/min)
Ionization mode; CI (reagent gas isobutane)
Detection Method; FID
<Analysis Conditions 4 (Analysis on 1,4-BIC Trans Isomer Ratio)>
From the area value of the gas chromatogram obtained with the gas chromatograph analysis conditions shown below, the trans isomer ratio (mol %) in the 1,4-BIC was calculated.
Device; 7890A manufactured by Agilent Technologies
Column; Agilent DB-17MS
Oven temperature; kept for 4 minutes at 40° C., temperature increased at 10° C./min from 40° C. to 250° C., kept for 5 minutes at 250° C.
Injection inlet temperature; 300° C.
Detector temperature; 300° C.
Carrier Gas; helium
Retention time of trans-1,4-BIC; 20.18 min
Retention time of cis-1,4-BIC; 20.308 min
Detection Method; FID
<Physical Property Evaluation>
Storage stability test
A certain amount of 1,4-BIC was weighed and put in a glass-made sample bottle, and then the glass-made sample bottle was filled with nitrogen. Then, after the 1,4-BIC was stored in a 50° C. constant temperature oven for 3 months, appearance was observed visually. The evaluation criteria are shown below.
Excellent; No Change
Good; slightly changed
Below average; changed a little
Bad; changed
The change means yellowing and becoming whitish.
Heating and rectifying conditions, and the results are shown in Table 2.

TABLE 2

| | | | No. | | | | | | | | |
|---|---|---|---|---|---|---|---|---|---|---|---|
| | | | Ex. 1 | Ex. 2 | Ex. 3 | Ex. 4 | Ex. 5 | Ex. 6 | Ex. 7 | Ex. 8 | Ex. 9 |
| 1,4-BAC | Trans isomer ratio | mol % | B 82 | C 82 | D 82 | E 72 | E 72 | F 72 | G 93 | G 93 | H 93 |
| | 3-azabicyclo[3.2.2]nonane content | mass % | 0.61 | 0.48 | 1.23 | 0.49 | 0.49 | 1.31 | 0.69 | 0.69 | 1.38 |

TABLE 2-continued

| 1,4-BIC | | | A | B | C | D | E | F | G | H | I |
|---|---|---|---|---|---|---|---|---|---|---|---|
| | Trans isomer ratio | mol % | 82 | 82 | 82 | 72 | 72 | 72 | 93 | 93 | 93 |
| | Compound represented by formula (1) Content | ppm | 15 | 0.19 | 270 | 12 | 0.15 | 250 | 20 | 0.22 | 285 |
| | Heating time(190° C.) | Hour | 4 | 8 | 2 | 4 | 8 | 2 | 4 | 8 | 3 |
| | Rectification distillation rate | mass % | 10~95 | 10~95 | 10~95 | 10~95 | 10~95 | 10~95 | 10~95 | 10~95 | 10~95 |
| | Purity | mass % | 99.8 | 99.8 | 99.7 | 99.8 | 99.8 | 99.7 | 99.7 | 99.7 | 99.7 |
| | Storage stability | Visual observation | Excellent | Excellent | Good | Excellent | Excellent | Good | Excellent | Excellent | Good |

| | | | No. | | | | | | | | | | | |
|---|---|---|---|---|---|---|---|---|---|---|---|---|---|---|
| | | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Reference Comp. Ex. 1 |
| 1,4-BAC | | | B | B | D | E | E | F | G | G | H | I | J | Reagent |
| | Trans isomer ratio | mol % | 82 | 82 | 82 | 72 | 72 | 72 | 93 | 93 | 93 | 67 | 97 | 40 |
| | 3-azabicyclo [3.2.2] nonane content | mass % | 0.61 | 0.61 | 1.23 | 0.49 | 0.49 | 1.3 | 0.69 | 0.69 | 1.38 | 0.57 | 0.8 | n.d |
| 1,4-BIC | | | J | K | L | M | N | O | P | Q | R | S | T | U |
| | Trans isomer ratio | mol % | 82 | 82 | 82 | 72 | 72 | 72 | 93 | 93 | 93 | 67 | 97 | 42 |
| | Compound represented by formula (1) content | ppm | n.d. | 0.07 | 340 | n.d. | 0.07 | 340 | n.d. | 0.07 | 380 | 12 | 18 | n.d |
| | Heating time (190° C.) | Hour | 4 | 12 | none | 8 | 12 | none | 8 | 12 | none | 4 | 4 | 4 |
| | Rectification distillation rate | mass % | 80~90 | 10~95 | 10~95 | 80~90 | 10~95 | 10~95 | 80~90 | 10~95 | 10~95 | 10~95 | 10~95 | 10~95 |
| | Purity | mass % | 99.8 | 99.8 | 99.8 | 99.8 | 99.8 | 99.8 | 99.7 | 99.7 | 99.8 | 99.8 | 99.5 | 99.7 |
| | Storage stability | Visual observation | Bad | Below average | Bad | Bad | Below average | Bad | Bad | Below average | Bad | Bad | Excellent | Excellent | Bad |

<Synthesis and Evaluation of Thermoplastic Polyurethane Elastomer (TPU)>

Example 10

Synthesis of Prepolymer

A four-neck flask equipped with a stirrer, a thermometer, a reflux tube, and a nitrogen inlet tube was charged with 225.2 parts by mass of 1,4-BIC (A), 252.5 parts by mass of ETERNACOLL UH-100 (polycarbonatediol having a number average molecular weight of 1000 manufactured by Ube Industries, Ltd.) dehydrated in advance under reduced pressure, and 494.8 parts by mass of ETERNACOLL UH-200 (polycarbonatediol having a number average molecular weight of 2000 manufactured by Ube Industries, Ltd.), and the mixture was allowed to react in a nitrogen atmosphere at 80° C. until the isocyanate group content reached 5.70 mass %, thereby producing an isocyanate group-terminated polyurethane prepolymer (a1) (simply called prepolymer (a1) in the following).

Synthesis of Polyurethane Elastomer (A1)

A stainless steel container was charged with 900 parts by mass of prepolymer (a1) having a preadjusted temperature of 80° C. in advance, 2.66 parts by mass of IRGANOX245 (heat-resistant stabilizer manufactured by BASF), 2.22 parts by mass of Tinuvin 234 (ultraviolet absorber manufactured by BASF), 1.33 parts by mass of Adeka StabLA-72 (HALS manufactured by ADEKA), and 0.112 parts by mass of a solution in which tin octylate (catalyst, trade name: Stanoct, manufactured by API Corporation) diluted in advance with diisononyl adipate (manufactured by J-PLUS Co., Ltd.) to 4 mass %; and the mixture was stirred and mixed using a high-speed disper at 1000 rpm for about 2 minutes. Then, as a chain extender, 54.51 parts by mass of 1,4-butanediol (1,4-BD)(manufactured by Wako Pure Chemical Industries, Ltd.) having a preadjusted temperature of 80° C. was added thereto, and the mixture was stirred and mixed using a high-speed disper at 1000 rpm for about 10 minutes.

Next, the reaction mixture liquid was poured into a SUS-made vat having a preadjusted temperature of 150° C., and reaction was performed at 150° C. for 1 hour, and then at 100° C. for 23 hours, thereby producing a polyurethane elastomer (A1), Thereafter, the polyurethane elastomer (A1) was taken out from the vat, and aged for 7 days under constant temperature and humidity conditions of a room temperature of 23° C. and a relative humidity of 55%.

The produced polyurethane elastomer (A1) was cut into dice with a bale cutter, and the diced resin was ground with a grinder. The ground pellets were dried under a nitrogen flow at 80° C. for a whole day and night. Strands were extruded using a monoaxial extruder (model: SZW40-28MG, manufactured by Technovel Corporation) with a cylinder temperature in the range of 150 to 245° C., and they were cut, thereby producing polyurethane elastomer (A1) pellets. The produced pellets were further dried under a nitrogen flow at 80° C. for a whole day and night.

Next, injection molding was performed using an injection molding machine (model: NEX-140, manufactured by NISSEI PLASTIC INDUSTRIAL CO., LTD) under the following conditions setting the screw number of revolution to 80 rpm and the barrel temperature to 150 to 235° C.: a mold temperature of 20° C., an injection time of 10 seconds, an injection rate of 60 mm/s, and cooling time of 45 seconds. The produced sheet having a thickness of 2 mm was aged under constant temperature and humidity conditions of a room temperature of 23° C. and a relative humidity of 55% for 7 days, thereby producing an elastomer sheet.

Examples 11 to 15 and Comparative Examples 12 to 16

Prepolymers (b1 to t1) were synthesized based on the mixing formulation shown in Table 3 in the same manner as in Example 10, and polyurethane elastomers (B1 to T1) were produced.

Reference Comparative Example 2

Prepolymer (U1) was synthesized based on the mixing formulation shown in Table 3 using 1,4-BIC (U)(1,4-BIC produced by using commercially available 1,4-BAC) produced in Reference Comparative Example 1 in the same manner as in Example 10, and polyurethane elastomer (U1) was produced.

Evaluation

<Hardness: Shore A>

Shore A hardness was measured in accordance with "JIS K-7311 Testing methods for thermoplastic polyurethane elastomers" (1995). The results are shown in Table 3 in numeral values.

<Tensile Physical Property>

A tensile test was performed using the produced sheet in conformity with the method described in "JIS K-7311 Testing methods for thermoplastic polyurethane elastomers" (1995). The test piece was punched out with a JIS-3 dumbbell, and the tensile strength (unit: MPa) and the elongation (unit: %) were measured under the conditions of the following: a tensile tester (manufactured by Toyoseiki kogyo Co., Ltd., trade name: all-automatic rubber tensile tester TYPE: AE-CT), a bench mark distance of 20 mm, and a tensile speed of 300 mm/min. The results are shown in Table 3.

<Notched Tear Strength>

The right angle portion of the produced right angle tear test piece was given a cut having a length of 1 mm in accordance with the method described in "JIS K-7311 Testing methods for thermoplastic polyurethane elastomers" (1995). Using the test piece, the notched tear strength (unit: N/cm) was measured with a tensile tester (manufactured by Toyoseiki kogyo Co., Ltd., trade name: all-automatic rubber tensile tester TYPE: AE-CT) under the conditions of a tensile speed of 300 mm/min. The results are shown in Table 3.

<Heat-Resistant NOx Yellowing Test>

The polyurethane elastomer test piece was allowed to stand in a 90° C. hot air circulation oven for 1000 hours. Thereafter, the exposure test was conducted in conformity with the test method in JIS L-0855 (2005) with a NOx concentration of 2,000 ppm for 2 hours. Thereafter, the test piece was further allowed to stand in a 70° C., 95% a constant temperature and humidity container of for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 3.

<Appearance>

Appearance of the test piece after the test was visually observed. The evaluation criteria are shown below. The results are shown in Table 3.

Excellent; No Change
Good; slightly changed
Below average; changed a little
Bad; changed The change means yellowing, becoming whitish, tack, and deformation.

TABLE 3

| | | | | Ex. 10 | Ex. 11 | Ex. 12 | Ex. 13 | Ex. 14 | Ex. 15 |
|---|---|---|---|---|---|---|---|---|---|
| Polyisocyanate component | 1,4-BIC | | | A | B | C | D | F | G |
| | Trans isomer ratio | | mol % | 82 | 82 | 82 | 72 | 72 | 93 |
| | Compound represented by formula (1) content | | ppm | 15 | 0.19 | 270 | 12 | 250 | 20 |
| Prepolymer formation | Prepolymer | | | a1 | b1 | c1 | d1 | f1 | g1 |
| | Amount of isocyanate component | | parts by mass | 225.2 | ← | ← | ← | ← | ← |
| | Amount of polyol component | UH-100 | parts by mass | 252.5 | ← | ← | ← | ← | ← |
| | | UH-200 | parts by mass | 494.8 | ← | ← | ← | ← | ← |
| | Prepolymer total amount | | parts by mass | 972.5 | ← | ← | ← | ← | ← |
| Chain extension reaction | Prepolymer charged | | parts by mass | 900.0 | ← | ← | ← | ← | ← |
| | Chain extender | 1,4-BD | parts by mass | 54.51 | ← | ← | ← | ← | ← |
| | Catalyst | 4% Stanoct/DINA | parts by mass | 0.112 | ← | ← | ← | ← | ← |
| | Stabilizer | IRGANOX245 | parts by mass | 2.66 | ← | ← | ← | ← | ← |
| | | Tinuvin234 | parts by mass | 2.22 | ← | ← | ← | ← | ← |
| | | Adeka Stab LA-72 | parts by mass | 1.33 | ← | ← | ← | ← | ← |

TABLE 3-continued

| Polyurethane elastomer | | | A1 | B1 | C1 | D1 | F1 | G1 |
|---|---|---|---|---|---|---|---|---|
| Hardness | | Shore A | 89 | 89 | 89 | 87 | 87 | 92 |
| Tensile physical property | Strength | MPa | 38 | 40 | 39 | 45 | 43 | 30 |
| | Elongation | % | 510 | 500 | 510 | 500 | 500 | 480 |
| Notched tear strength | | N/cm | 850 | 870 | 855 | 900 | 900 | 800 |
| Appearance After heat-resistant NOx test | | Visual observation | Excellent | Excellent | Excellent | Excellent | Good | Excellent |
| After heat-resistant NOx test | Elongation | % | 490 | 480 | 460 | 470 | 450 | 440 |
| | Elongation Retention | % | 96 | 96 | 90 | 94 | 90 | 92 |
| | Notched tear strength | N/cm | 800 | 810 | 790 | 840 | 820 | 750 |
| | Notched tear strength Retention | % | 94 | 93 | 92 | 93 | 91 | 94 |

| | | | No. | | | | | |
|---|---|---|---|---|---|---|---|---|
| | | | Comp. Ex. 12 | Comp. Ex. 13 | Comp. Ex. 14 | Comp. Ex. 15 | Comp. Ex. 16 | Ref. Comp. Ex. 2 |
| Polyisocyanate component | 1,4-BIC | | J | K | L | S | T | U |
| | Trans isomer ratio | mol % | 82 | 82 | 82 | 67 | 97 | 40 |
| | Compound represented by formula (1) content | ppm | n.d. | 0.07 | 340 | 12 | 18 | n.d |
| Prepolymer formation | Prepolymer | | j1 | k1 | l1 | s1 | t1 | u1 |
| | Amount of isocyanate component | parts by mass | ← | ← | ← | ← | ← | ← |
| | Amount of polyol component UH-100 | parts by mass | ← | ← | ← | ← | ← | ← |
| | UH-200 | parts by mass | ← | ← | ← | ← | ← | ← |
| | Prepolymer total amount | parts by mass | ← | ← | ← | ← | ← | ← |
| Chain extension reaction | Prepolymer charged | parts by mass | ← | ← | ← | ← | ← | ← |
| | Chain extender 1,4-BD | parts by mass | ← | ← | ← | ← | ← | ← |
| | Catalyst 4% Stanoct/DINA | parts by mass | ← | ← | ← | ← | ← | ← |
| | Stabilizer IRGANOX245 | parts by mass | ← | ← | ← | ← | ← | ← |
| | Tinuvin234 | parts by mass | ← | ← | ← | ← | ← | ← |
| | Adeka Stab LA-72 | parts by mass | ← | ← | ← | ← | ← | ← |
| Polyurethane elastomer | | | J1 | K1 | L1 | S1 | T1 | U1 |
| Hardness | | Shore A | 89 | 89 | 89 | 83 | 97 | 75 |
| Tensile physical property | Strength | MPa | 40 | 39 | 39 | 48 | 20 | 42 |
| | Elongation | % | 510 | 500 | 500 | 480 | 450 | 350 |
| Notched tear strength | | N/cm | 850 | 830 | 830 | 850 | 600 | 800 |
| Appearance After heat-resistant NOx test | | Visual observation | Below average | Good | Bad | Below average | Below average | Bad |
| After heat-resistant NOx test | Elongation | % | 490 | 490 | 420 | 400 | 380 | 300 |
| | Elongation Retention | % | 96 | 98 | 84 | 83 | 84 | 84 |
| | Notched tear strength | N/cm | 790 | 780 | 720 | 760 | 530 | 650 |
| | Notched tear strength Retention | % | 93 | 94 | 87 | 89 | 88 | 81 |

The details of the abbreviations in Tables are shown below.

UH-100; ETERNACOLL UH-100, polycarbonatediol having a number average molecular weight of 1000 (manufactured by Ube Industries, Ltd.)

UH-200; ETERNACOLL UH-200, polycarbonatediol having a number average molecular weight of 2000 (manufactured by Ube Industries, Ltd.)

1,4-BD; 1,4-butanediol (manufactured by Wako Pure Chemical Industries, Ltd.)

DINA; diisononyl adipate (manufactured by J-PLUS Co., Ltd.)

<Synthesis and Evaluation of Thermosetting Polyurethane Elastomer (TSU)>

Example 16

Synthesis of Prepolymer

A four-neck flask equipped with a stirrer, a thermometer, a reflux tube, and a nitrogen inlet tube was charged with 101.9 parts by mass of 1,4-BIC (A), and 505.4 parts by mass of PTG2000SN (polytetramethylene ether glycol having a number average molecular weight of 2000, manufactured by Hodogaya Chemical Co., LTD.) dehydrated in advance under reduced pressure; and the mixture was stirred in a nitrogen atmosphere at 80° C. for 1 hour, and thereafter, 0.076 parts by mass of a dibutyltin dilaurate solution diluted in advance with diisononyl adipate (manufactured by J-PLUS Co., Ltd.) to 4 mass % was introduced. The reaction was continued at 80° C. until the isocyanate group content reached 3.8 mass %, thereby producing an isocyanate group-terminated polyurethane prepolymer (a2)(simply called prepolymer (a2) in the following).

Preparation of Polyurethane Elastomer (A2)

A stainless steel container was charged with 200 parts by mass of prepolymer (a2) having a preadjusted temperature of 80° C., 1.24 parts by mass of IRGANOX245 (heat-resistant stabilizer manufactured by BASF), 1.03 parts by mass of Tinuvin234 (ultraviolet absorber manufactured by BASF), 0.62 parts by mass of Adeka StabLA-72 (HALS manufactured by ADEKA), and 0.050 parts by mass of a dibutyltin dilaurate (DBTDL) solution diluted with diisononyl adipate (manufactured by J-PLUS Co., Ltd.) in advance to 4 mass %; and the mixture was stirred and mixed using a three-one motor (trade name: HEIDON FBL3000, manufactured by Shinto Scientific Co., Ltd.) at 600 rpm for about 1 minute.

Next, 7.97 parts by mass of a chain extender mixture dehydrated in advance under reduced pressure prepared by melt-mixing 1.98 parts by mass of trimethylolpropane (TMP)(manufactured by Wako Pure Chemical Industries, Ltd.) and 5.99 parts by mass of 1,4-butanediol (1,4-BD) (manufactured by Wako Pure Chemical industries, Ltd.) at 60° C. was added thereto. The mixture was fully stirred for about another 2 minutes until it was thoroughly uniform, and thereafter, vacuum defoaming was immediately performed to defoam the mixed solution. The mixture was poured while caring not to include bubbles in the sheet-type button mold to which a releasing agent (trade name: MIRAX RS-102, manufactured by Miyoshi Oil & Fat Co., Ltd.) was applied in advance and having an adjusted temperature of 100° C., and the mixture was allowed to react at 100° C. for 22 hours. Thereafter, the polyurethane elastomer was released from the mold, and the hardness was measured after 4 hours under constant temperature and humidity conditions of a room temperature of 23° C. and a relative humidity of 50%, and after being aged for further 7 days, used for physical property measurement.

Examples 17 to 21 and Comparative Examples 17 to 21

Prepolymers (b2 to t2) were synthesized in the same manner as in Example 16 based on the mixing formulation shown in Table 4, thereby producing polyurethane elastomers (B2 to T2).
Evaluation
<Hardness: Shore A>
Shore A hardness was measured in accordance with "JIS K-7311 Testing methods for thermoplastic polyurethane elastomers" (1995). The results are shown in Table 4 in numeral values.
<Tensile Physical Property>
A tensile test was performed using the produced sheet in conformity with the method described in "JIS K-7311 Testing methods for thermoplastic polyurethane elastomers" (1995). The test piece was punched out with a JIS-3 dumbbell, and the tensile strength at break (unit: MPa) and the elongation (unit: %) were measured using a tensile tester (manufactured by Toyoseiki kogyo Co., Ltd., trade name: all-automatic rubber tensile tester TYPE: AE-CT) under the following conditions: a bench mark distance of 20 mm and a tensile speed of 300 mm/min. The results are shown in Table 4.
<Heat-Resistant NOx Yellowing Test>
The polyurethane elastomer test piece was allowed to stand in a hot air circulation oven at 90° C. for 1000 hours. Thereafter, the exposure test was conducted in conformity with the test method in JIS L-0855 (2005) with a NOx concentration of 2,000 ppm for 2 hours. Thereafter, the test piece was further allowed to stand in a constant temperature and humidity container of 70° C. and 95% for 24 hours. The appearance after being allowed to stand was observed visually.
After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 4.
<Appearance>
Appearance of the test piece after the test was visually observed. The evaluation criteria are shown below. The results are shown in Table 4.
Excellent; No Change
Good; slightly changed
Below average; changed a little
Bad; changed
The change means yellowing, becoming whitish, tack, and deformation.

TABLE 4

| | | | Ex. 16 | Ex. 17 | Ex. 18 | Ex. 19 | Ex. 20 | Ex. 21 | Comp. Ex. 17 | Comp. Ex. 18 | Comp. Ex. 19 | Comp. Ex. 20 | Comp. Ex. 21 |
|---|---|---|---|---|---|---|---|---|---|---|---|---|---|
| Polyisocyanate component | 1,4-BIC Trans isomer ratio | mol % | A 82 | B 82 | C 82 | D 72 | F 72 | G 93 | J 82 | K 82 | L 82 | S 67 | T 97 |
| | Compound represented by formula (1) content | ppm | 15 | 0.19 | 270 | 12 | 250 | 20 | n.d. | 0.07 | 340 | 12 | 18 |
| Prepolymer formation | Prepolymer Amount of isocyanate component | parts by mass | a2 101.9 | b2 ↓ | c2 ↓ | d2 ↓ | f2 ↓ | g2 ↓ | j2 ↓ | k2 ↓ | L2 ↓ | s2 ↓ | t2 ↓ |
| | Amount of polyol component PTG2000SN | parts by mass | 505.4 | ↓ | ↓ | ↓ | ↓ | ↓ | ↓ | ↓ | ↓ | ↓ | ↓ |
| | Catalyst 4% DBTDL/ DINA | parts by mass | 0.0759 | ↓ | ↓ | ↓ | ↓ | ↓ | ↓ | ↓ | ↓ | ↓ | ↓ |
| | Prepolymer total amount | parts by mass | 607.3 | ↓ | ↓ | ↓ | ↓ | ↓ | ↓ | ↓ | ↓ | ↓ | ↓ |
| Chain extension reaction | Prepolymer charged | parts by mass | 200.0 | ↓ | ↓ | ↓ | ↓ | ↓ | ↓ | ↓ | ↓ | ↓ | ↓ |
| | Chain extender 1,4-BD | parts by mass | 5.99 | ↓ | ↓ | ↓ | ↓ | ↓ | ↓ | ↓ | ↓ | ↓ | ↓ |
| | TMP | parts by mass | 1.98 | ↓ | ↓ | ↓ | ↓ | ↓ | ↓ | ↓ | ↓ | ↓ | ↓ |
| | Catalyst 4% DBTDL/ DINA | parts by mass | 0.050 | ↓ | ↓ | ↓ | ↓ | ↓ | ↓ | ↓ | ↓ | ↓ | ↓ |
| | Stabilizer IRGANOX 245 | parts by mass | 1.24 | ↓ | ↓ | ↓ | ↓ | ↓ | ↓ | ↓ | ↓ | ↓ | ↓ |
| | Tinuvin234 | parts by mass | 1.03 | ↓ | ↓ | ↓ | ↓ | ↓ | ↓ | ↓ | ↓ | ↓ | ↓ |
| | Adeka Stab LA-72 | parts by mass | 0.62 | ↓ | ↓ | ↓ | ↓ | ↓ | ↓ | ↓ | ↓ | ↓ | ↓ |
| Polyurethane elastomer Hardness | | Shore A | A2 74 | B2 74 | C2 74 | D2 72 | F2 72 | G2 76 | J2 74 | K2 74 | L2 74 | S2 71 | T2 78 |
| Tensile physical property Strength | | MPa | 12 | 14 | 12 | 15 | 15 | 10 | 13 | 12 | 13 | 18 | 7 |
| Elongation | | % | 430 | 450 | 430 | 430 | 430 | 400 | 430 | 430 | 440 | 440 | 350 |
| After heat-resistant NOx test Appearance | | Visual observation | Excellent | Excellent | Excellent | Excellent | Good | Excellent | Below average | Good | Bad | Bad | Below average |
| Elongation | | % | 420 | 430 | 400 | 390 | 370 | 360 | 420 | 420 | 370 | 360 | 300 |
| Elongation Retention | | % | 98 | 96 | 93 | 91 | 86 | 90 | 98 | 98 | 84 | 82 | 86 |

The details of the abbreviations in Tables are shown below.

PTG2000SN; polytetramethylene ether glycol having a number average molecular weight of 2000, manufactured by Hodogaya Chemical Co., LTD.

TMP; trimethylolpropane (manufactured by Wako Pure Chemical Industries, Ltd.)

1,4-BD; 1,4-butanediol (manufactured by Wako Pure Chemical Industries, Ltd.)

DBTDL; dibutyltin dilaurate (manufactured by Wako Pure Chemical Industries, Ltd.)

DINA; diisononyl adipate (manufactured by J-PLUS Co., Ltd.)

<Synthesis and Evaluation of Optical Polyurethane Resin>

Example 22

48.6 parts by mass of 1,4-BAC (A), 0.098 parts by mass of dimethyltin dichloride as a catalyst, and 0.10 parts by mass of acidic phosphoric ester (ZELEC UN manufactured by Stepan), and 0.05 parts by mass of ultraviolet absorber (Biosorb 583, manufactured by KYODO CHEMICAL CO., LTD.) were mixed and dissolved at 10 to 15° C.

Thereafter, a polythiol component composed of 28.2 parts by mass of 1,2-bis(2-mercaptoethylthio)-3-propane thiol (CGST) and 21.4 parts by mass of pentaerythritoltetra(3-mercapto propionate)(PEMP, manufactured by SC organic chemical) was introduced and mixed, thereby producing a mixed homogenous liquid (polymerizable composition).

Next, the homogenous mixture was defoamed for 1 hour, and then thereafter, filtered with a 1 μm PTFE (polytetrafluoroethylene) filter, and introduced into a mold for optical member composed of a 4D glass mold and a tape.

The mold was put into an oven, and the temperature was increased gradually from 25° C. to 120° C. taking 20 hours to cause polymerization. After the completion of the polymerization, the mold was taken out from the oven, and the product was released. Annealing was further conducted at 120° C. for 3 hours, thereby producing optical polyurethane resin A3.

Examples 22 to 27 and Comparative Examples 22 to 26

Optical polyurethane resins (B3 to T3) were produced in the same manner as in Example 22 based on the mixing formulation shown in Table 5.

Evaluation

<Optical Properties>

The refraction (ne) and the Abbe's number (ve) were measured using a Pulfrich refractometer at 20° C. The results are shown in Table 5.

<Appearance>

Appearance of optical polyurethane resin was observed visually.

<Open-Hole Tensile Test>

A resin flat plate having adjusted diameter of 45 mm and thickness of 2.5 mm was drilled at two points using AUTOGRAPH AGS-J (manufactured by Shimadzu Corporation) so that the resin flat plate had a hole having a diameter of 1.6 mm at the two points. A 1.6 mm metal-made shaft was allowed to pass through the holes, and both ends of the sample were attached to a fixture. Thereafter, pulling was conducted at a rate of 5 mm/min, and the maximum test force was measured. The obtained maximum test force from which the resin pressure was deducted was regarded as an open-hole tensile strength (unit: N/mm).

<Heat-Resistant NOx Yellowing Test>

The optical polyurethane resin test piece was allowed to stand in a 90° C. hot air circulation oven for 1000 hours. Thereafter, the exposure test was conducted in conformity with the test method in JIS L-0855 (2005) with a NOx concentration of 2,000 ppm for 2 hours. Thereafter, the test piece was further allowed to stand in a constant temperature and humidity container of 70° C. and 95% for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 5.

<Appearance>

Appearance of the test piece after the test was visually observed. The evaluation criteria are shown below. The results are shown in Table 5.

Excellent; No Change
Good; slightly changed
Below average; changed a little
Bad; changed The change means yellowing, becoming whitish, tack, and deformation.

TABLE 5

| | | | No. | | | | | |
|---|---|---|---|---|---|---|---|---|
| | | | Ex. 22 | Ex. 23 | Ex. 24 | Ex. 25 | Ex. 26 | Ex. 27 |
| Polyisocyanate component | 1,4-BIC | | A | B | C | D | F | G |
| | Trans isomer ratio | mol % | 82 | 82 | 82 | 72 | 72 | 93 |
| | Compound represented by formula (1) content | ppm | 15 | 0.19 | 270 | 12 | 250 | 20 |
| Amount of isocyanate component | | parts by mass | 48.6 | ← | ← | ← | ← | ← |
| Amount of polythiol component | GST | parts by mass | 28.2 | ← | ← | ← | ← | ← |
| | PEMP | parts by mass | 21.4 | ← | ← | ← | ← | ← |
| Releasing agent | ZELEC UN | parts by mass | 0.10 | ← | ← | ← | ← | ← |
| Ultraviolet absorber | Biosorb 583 | parts by mass | 0.05 | ← | ← | ← | ← | ← |
| Catalyst | Dibutyltin dichloride | ppm | 0.098 | ← | ← | ← | ← | ← |
| Optical polyurethane resin | | | A3 | B3 | C3 | D3 | F3 | G3 |
| Refraction(ne) | | | 1.597 | 1.597 | 1.597 | 1.597 | 1.597 | 1.597 |
| Abbe's number(ve) | | | 38.6 | 38.6 | 38.6 | 38.6 | 38.6 | 38.6 |

TABLE 5-continued

| | | | | | | | | |
|---|---|---|---|---|---|---|---|---|
| Appearance | | | Transparent | Transparent | Transparent | Transparent | Transparent | Transparent |
| Tensile physical property | Open-hole Tensile test | N/mm | 579 | 588 | 569 | 608 | 608 | 539 |
| After heat-resistant NOx test | Appearance | Visual observation | Excellent | Excellent | Excellent | Good | Good | Excellent |
| | Open-hole Tensile test | N/mm | 569 | 569 | 539 | 598 | 579 | 510 |
| | Open-hole Tensile test Retention | % | 98.3 | 96.7 | 94.8 | 98.4 | 95.2 | 94.5 |

| | | | No. | | | | |
|---|---|---|---|---|---|---|---|
| | | | Comp. Ex. 22 | Comp. Ex. 23 | Comp. Ex. 24 | Comp. Ex. 25 | Comp. Ex. 26 |
| Polyisocyanate component | 1,4-BIC | | J | K | L | S | T |
| | Trans isomer ratio | mol % | 82 | 82 | 82 | 67 | 97 |
| | Compound represented by formula (1) content | ppm | n.d. | 0.07 | 340 | 12 | 18 |
| Amount of isocyanate component | | parts by mass | ← | ← | ← | ← | ← |
| Amount of polythiol component | GST | parts by mass | ← | ← | ← | ← | ← |
| | PEMP | parts by mass | ← | ← | ← | ← | ← |
| Releasing agent | ZELEC UN | parts by mass | ← | ← | ← | ← | ← |
| Ultraviolet absorber | Biosorb 583 | parts by mass | ← | ← | ← | ← | ← |
| Catalyst | Dibutyltin dichloride | ppm | ← | ← | ← | ← | ← |
| Optical polyurethane resin | | | J3 | K3 | L3 | S3 | T3 |
| Refraction(ne) | | | 1.597 | 1.597 | 1.597 | 1.597 | 1.597 |
| Abbe's numher(ve) | | | 38.6 | 38.6 | 38.6 | 38..6 | 38.6 |
| Appearance | | | Transparent | Transparent | Transparent | Transparent | Cloudy |
| Tensile physical property | Open-hole Tensile test | N/mm | 569 | 569 | 539 | 637 | 441 |
| After heat-resistant NOx test | Appearance | Visual observation | Below average | Good | Bad | Below average | Bad |
| | Open-hole Tensile test | N/mm | 559 | 559 | 500 | 559 | 392 |
| | Open-hole Tensile test Retention | % | 98.3 | 98.3 | 92.7 | 87.7 | 88.9 |

The details of the abbreviations in Tables are shown below.

PEMP; pentaerythritoltetra(3-mercaptopropionate), manufactured by SC organic chemical Co., Ltd.

GST; 1,2-bis(2-mercaptoethylthio)-3-propane thiol

<Synthesis and Evaluation of Aqueous Polyurethane Resin (PUD)>

Synthesis Example 1

Synthesis of Polyoxyethylene Side Chain-Containing Diol

A four-neck flask equipped with a stirrer, a thermometer, a reflux tube, and a nitrogen inlet tube was charged with 1000 parts by mass of methoxypolyethylene glycol having a number average molecular weight of 1000 (manufactured by TOHO Chemical Industry Co., Ltd.) and 1682 parts by mass of 1,6-hexamethylene diisocyanate (trade name: TAKENATE-700, manufactured by Mitsui Chemicals, Inc.), and the mixture was allowed to react in a nitrogen atmosphere at 90° C. for 9 hours. The produced reaction solution was subjected to thin-film distillation to remove unreacted 1,6-hexamethylene diisocyanate, thereby producing polyoxyethylene group-containing monoisocyanate. Then, a four-neck flask equipped with a stirrer, a thermometer, a reflux tube, and a nitrogen inlet tube was charged with 82.5 parts by mass of diethanol amine, and 917.5 parts by mass of the above-described polyoxyethylene group-containing monoisocyanate was gradually dropped therein in a nitrogen atmosphere while cooling air so that the reaction temperature does not exceed 70° C. After the dropping was completed, the mixture was stirred for about 1 hour in a nitrogen atmosphere at 70° C., and it was confirmed that the isocyanate group disappeared, thereby producing polyoxyethylene side chain-containing diol.

Example 28

A four-neck flask equipped with a stirrer, a thermometer, a reflux tube, and a nitrogen inlet tube was charged with 38.6 parts by mass of polyoxyethylene side chain-containing diol synthesized in Synthesis Example 1, 120.2 parts by mass of ETERNACOLL UH-100 (polycarbonatediol having a number average molecular weight of 1000 manufactured by Ube Industries, Ltd.) dehydrated in advance under reduced pressure, 120.2 parts by mass of ETERNACOLL UH-200 (polycarbonatediol having a number average molecular weight of 2000 manufactured by Ube Industries, Ltd.), 89.78 parts by mass of methyl ethyl ketone, and 3.4 parts by mass of IRGANOX 245 (heat-resistant stabilizer manufactured by BASF), and the mixture was stirred.

Next, 57.6 parts by mass of 1,4-BAC (A) was introduced thereto and the mixture was allowed to react at 75° C. for 2 hours, thereby producing an isocyanate group-terminated prepolymer.

Next, the reaction solution was cooled to 50° C., and 134.7 parts by mass of acetone was introduced thereto. Furthermore, the mixture was cooled to 30° C., and then 742.63 parts by mass of ion-exchange water was gradually added to disperse the isocyanate group-terminated prepolymer in water. Chain extension with 31.87 parts by mass of a 20 mass % aqueous solution of hexamethylene diamine was performed, and furthermore, acetone was distilled off, thereby producing an aqueous dispersion of aqueous polyurethane resin A4 having a solid content of 34.6 mass %.

Examples 29 to 33 and Comparative Examples 27 to 31

Aqueous polyurethane resins (B4 to T4) were produced in the same manner as in Example 28 based on the mixing formulation shown in Table 6.

Evaluation

<Production of Aqueous Polyurethane Film>

The aqueous polyurethane resin was poured onto a polypropylene-made substrate so that the film thickness after drying was 200 μm, and moisture content was dried at room temperature for 24 hours. Thereafter, heating was conducted at 110° C. for 1 hour, thereby completely volatilizing water. After cooling to room temperature, the film was released from the substrate, thereby producing an aqueous polyurethane film.

<Tensile Test of Aqueous Polyurethane Film>

Tensile test was conducted using a tensile tester (Manufactured by INTESCO co., Ltd., model: type 205) set in a laboratory at 23° C. and a relative humidity of 55%. To be more specific, 1.60 tensile test was conducted using a test piece punched out with a JIS4 dumbbell with conditions of a distance between chucks of 20 mm and a tensile speed of 300 mm/min. The tensile strength at break (unit: MPa) and elongation (unit: %) of the polyurethane film were measured in this manner.

<Heat-Resistant NOx Yellowing Test>

A polyurethane film test piece was allowed to stand in a 90° C. hot air circulation oven for 1000 hours. Thereafter, in conformity with the test method in JIS L-0855 (2005), the exposure test was conducted with a NOx concentration of 2,000 ppm for 2 hours. Thereafter, the test piece was further allowed to stand in a constant temperature and humidity container of 70° C. and 95% for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 6.

<Appearance>

Appearance of the test piece after the test was visually observed. The evaluation criteria are shown below. The results are shown in Table 6.

Excellent; No Change
Good; slightly changed
Below average; changed a little
Bad; changed The change means yellowing, becoming whitish, tack, and deformation.

TABLE 6

| | | | | Ex. 28 | Ex. 29 | Ex. 30 | Ex. 31 | Ex. 32 | Ex. 33 |
|---|---|---|---|---|---|---|---|---|---|
| Polyisocyanate component | | 1,4-BIC | | A | B | C | D | F | G |
| | | Trans isomer ratio | mol % | 82 | 82 | 82 | 72 | 72 | 93 |
| | | Compound represented by formula (1) content | ppm | 15 | 0.19 | 270 | 12 | 250 | 20 |
| Prepolymer formation | Amount of isocyanate component | | parts by mass | 57.6 | ← | ← | ← | ← | ← |
| | Amount of polyol component | UH-100 | parts by mass | 120.2 | ← | ← | ← | ← | ← |
| | | UH-200 | parts by mass | 120.2 | ← | ← | ← | ← | ← |
| | | Polyoxyethylene chain-containing diol | parts by mass | 38.6 | ← | ← | ← | ← | ← |
| | Stabilizer | IRGANOX245 | parts by mass | 3.4 | ← | ← | ← | ← | ← |
| | Solvent | Methyl ethyl ketone | parts by mass | 89.78 | ← | ← | ← | ← | ← |
| Chain extension reaction | Solvent | Acetone | parts by mass | 134.7 | ← | ← | ← | ← | ← |
| | | Ion-exchange water | parts by mass | 742.6 | ← | ← | ← | ← | ← |
| | Chain extender | 20% HAD aqueous solution | parts by mass | 31.87 | ← | ← | ← | ← | ← |
| Aqueous polyurethane resin | | | | A4 | B4 | C4 | D4 | F4 | G4 |
| Solid content concentration | | | mass % | 34.6 | 34.6 | 34.5 | 34.5 | 34.5 | 34.5 |
| Viscosity (25° C.) | | | mPa·s | 10 | 12 | 11 | 12 | 12 | 10 |
| Tensile physical property | Strength | | MPa | 40 | 40 | 38 | 44 | 44 | 35 |
| | Elongation | | % | 540 | 550 | 540 | 570 | 570 | 520 |
| After heat-resistant NOx test | Appearance | | Visual observation | Excellent | Excellent | Excellent | Excellent | Good | Excellent |
| | Elongation | | % | 540 | 540 | 520 | 530 | 510 | 490 |
| | Elongation Retention | | % | 100 | 98 | 96 | 93 | 89 | 94 |

| | | | | Comp. Ex. 27 | Comp. Ex. 28 | Comp. Ex. 29 | Comp. Ex. 30 | Comp. Ex. 31 |
|---|---|---|---|---|---|---|---|---|
| Polyisocyanate component | | 1,4-BIC | | J | K | L | S | T |
| | | Trans isomer ratio | mol % | 82 | 82 | 82 | 67 | 97 |
| | | Compound represented by formula (1) content | ppm | n.d. | 0.07 | 340 | 12 | 18 |
| Prepolymer formation | Amount of isocyanate component | | parts by mass | ← | ← | ← | ← | ← |
| | Amount of polyol component | UH-100 | parts by mass | ← | ← | ← | ← | ← |
| | | UH-200 | parts by mass | ← | ← | ← | ← | ← |
| | | Polyoxyethylene chain-containing diol | parts by mass | ← | ← | ← | ← | ← |
| | Stabilizer | IRGANOX245 | parts by mass | ← | ← | ← | ← | ← |
| | Solvent | Methyl ethyl ketone | parts by mass | ← | ← | ← | ← | ← |

TABLE 6-continued

| | | | | | | | | |
|---|---|---|---|---|---|---|---|---|
| Chain extension reaction | Solvent | Acetone | parts by mass | ← | ← | ← | ← | ← |
| | | Ion-exchange water | parts by mass | ← | ← | ← | ← | ← |
| | Chain extender | 20% HAD aqueous solution | parts by mass | ← | ← | ← | ← | ← |
| Aqueous polyurethane resin | | | | J4 | K4 | L4 | S4 | T4 |
| Solid content concentration | | | mass % | 34.6 | 34.5 | 34.6 | 34.5 | 34.5 |
| Viscosity (25° C.) | | | mPa · s | 12 | 10 | 12 | 10 | 10 |
| Tensile physical property | Strength | | MPa | 41 | 40 | 40 | 46 | 27 |
| | Elongation | | % | 550 | 540 | 540 | 570 | 440 |
| After heat-resistant NOx test | Appearance | | Visual observation | Below average | Good | Bad | Bad | Below average |
| | Elongation | | % | 540 | 540 | 460 | 480 | 370 |
| | Elongation Retention | | % | 98 | 100 | 85 | 84 | 84 |

The details of the abbreviations in Tables are shown below.

UH-100; ETERNACOLL UH-100, polycarbonatediol having a number average molecular weight of 1000 (manufactured by Ube industries, Ltd.)

UH-200; ETERNACOLL UH-200, polycarbonatediol having a number average molecular weight of 2000 (manufactured by Ube industries, Ltd.)

HDA; hexamethylenediamine

<Synthesis and Evaluation of Polyurethane Resin Solution>

Example 34

A reactor equipped with anchor wings, a thermometer, and a water-cooling condenser, and capable of continuous stirring torque measurement was charged with 46.53 parts by mass of ETERNACOLL UH-100 (polycarbonatediol having a number average molecular weight of 1000 manufactured by Ube industries, Ltd.) dehydrated in advance under reduced pressure, 91.17 parts by mass of ETERNACOLL UH-200 (polycarbonatediol having a number average molecular weight of 2000 manufactured by Ube Industries, Ltd.), and 53.68 parts by mass of 1,4-BIC (A) in a nitrogen atmosphere, and the temperature was increased at a stirring rate of 200 rpm to 80° C.

Next, reaction was performed at 80° C. for 1 hour, and then as a catalyst, 0.019 parts by mass of a solution in which dibutyltin dilaurate (DBTDL) was diluted in advance with N,N-dimethylformamide (DMF) to 10 mass % was added.

Reaction was further performed at the same temperature for 2 hours, and then thereafter, reaction was performed until the isocyanate group concentration reached 8.09 mass %, thereby producing an isocyanate group-terminated urethane prepolymer (a5).

Next, after the isocyanate group-terminated urethane prepolymer (a5) was cooled to 50° C., 765.53 parts by mass of DMF, which was dehydrated in advance with molecular sieves 4 A immersed therein, was gradually added with a stirring rate of 300 rpm so that the isocyanate group-terminated urethane prepolymer (a5) concentration reached 20 mass %, thereby dissolving the isocyanate group-terminated urethane prepolymer (a5).

Thereafter, the DMF solution of the isocyanate group-terminated urethane prepolymer (a2) was again heated to 80° C. or less. 27.43 parts by mass of ethylene glycol (EG)(special grade, manufactured by Wako Pure Chemical Industries, Ltd.) diluted to 40 mass % with DMF, and 0.38 mass % of a DBTDL solution diluted to 10 mass % with DMF were introduced thereto. After reaction at 80° C. for 6 hours, 1.44 parts by mass of EG diluted to 40 mass % with DMF was introduced thereto. The mixture was allowed to react further at 80° C. for 1 hour.

Furthermore, 6.1 parts by mass (solid content 0.61 parts by mass) of IRGANOX245 (heat-resistant stabilizer manufactured by BASF), 5.1 parts by mass (solid content 0.51 parts by mass) of Tinuvin234 (HALS manufactured by BASF), and 3.0 parts by mass (solid content 0.30 parts by mass) of Adeka StabLA-72 (manufactured by ADEKA, ultraviolet absorber), each of which dissolved in DMF to be 10 mass % were introduced, thereby producing a polyurethane resin solution (A5). The polyurethane resin had a solid content concentration of 20 mass %.

Examples 35 to 39 and Comparative Examples 32 to 36

Polyurethane resin solutions (B5 to T5) were synthesized in the same manner as in Example 34 based on the mixing formulation shown in Table 7.

Evaluation

<Polyurethane Resin Solution Viscosity>

Using E-type viscometer (manufactured by TOKI Sangyo Co., Ltd., trade name: TOKIMEC TV-30 VISCOMETER), the viscosity (unit: Pa·s) of the polyurethane resin solution was measured at a revolving rate of 0.1 rpm and a temperature of 25° C. with a rotor having a size of 1°34'×R24. The amount of the sample for the measurement was about 1 to 1.2 mL.

<Polyurethane Film Production>

The polyurethane resin solution was applied on a glass plate so that the film thickness after drying was 100 μm, and thereafter, in a nitrogen atmosphere, the pressure was reduced at 60° C. for 3 hours, thereby distilling off DMF, and producing a polyurethane film.

<Tensile Test of Polyurethane Film>

Tensile test was conducted using a tensile tester (Manufactured by INTESCO co., Ltd., model: type 205) set in a laboratory at 23° C. and a relative humidity of 55%. To be more specific, tensile test was conducted using a film test piece having a size of 60 mm in the tensile direction and a width of 10 mm with conditions of a distance between chucks of 30 mm and a tensile speed of 300 mm/min. The tensile strength at break (unit: MPa) and elongation (unit: %) of the polyurethane film were measured in this manner.

<Heat-Resistant NOx Yellowing Test>

A polyurethane film test piece was allowed to stand in a 90° C. hot air circulation oven for 1000 hours. Thereafter, the exposure test was conducted with a NOx concentration of 2,000 ppm for 2 hours in conformity with the test method in JIS L-0855 (2005). Thereafter, the test piece was further allowed to stand in a constant temperature and humidity container of 70° C. and 95% for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 7.

<Appearance>

Appearance of the test piece after the test was visually observed. The evaluation criteria are shown below. The results are shown in Table 7.

Excellent; No Change
Good; slightly changed
Below average; changed a little
Bad; changed The change means yellowing, becoming whitish, tack, and deformation.

TABLE 7

|  |  |  | No. | | | | | | |
| --- | --- | --- | --- | --- | --- | --- | --- | --- | --- |
|  |  |  | Ex. 33 | Ex. 35 | Ex. 36 | Ex. 37 | Ex. 38 | Ex. 39 | Comp. Ex. 32 |
| Polyisocyanate component | 1,4-BIC |  | A | B | C | D | F | G | J |
|  | Trans isomer ratio | mol % | 82 | 82 | 82 | 72 | 72 | 93 | 82 |
|  | Compound represented by formula (1) content | ppm | 15 | 0.19 | 270 | 12 | 250 | 20 | n.d. |
| Prepolymer formation | Prepolymer |  | a5 | b5 | c5 | d5 | f5 | g5 | j5 |
|  | Amount of isocyanate component | parts by mass | 53.68 | ← | ← | ← | ← | ← | ← |
|  | Amount of polyol component | UH-100 | parts by mass | 46.53 | ← | ← | ← | ← | ← | ← |
|  |  | UH-200 | parts by mass | 91.17 | ← | ← | ← | ← | ← | ← |
|  | Catalyst | 10% DBTDL/DMF | parts by mass | 0.019 | ← | ← | ← | ← | ← | ← |
| Chain extension reaction | Solvent | DMF | parts by mass | 765.5 | ← | ← | ← | ← | ← | ← |
|  | Chain extender (Dividedly added) | Ethylene glycol | parts by mass | 10.97 | ← | ← | ← | ← | ← | ← |
|  |  | Ethylene glycol | parts by mass | 0.58 | ← | ← | ← | ← | ← | ← |
|  | Catalyst | 10% DBTDL/DMF | parts by mass | 0.38 | ← | ← | ← | ← | ← | ← |
|  | Solvent | DMF | parts by mass | 17.3 | ← | ← | ← | ← | ← | ← |
|  | Stabilizer | IRGANOX 245 | parts by mass | 0.61 | ← | ← | ← | ← | ← | ← |
|  |  | Tinuvin234 | parts by mass | 0.51 | ← | ← | ← | ← | ← | ← |
|  |  | LA-72 | parts by mass | 0.30 | ← | ← | ← | ← | ← | ← |
|  | Solvent | DMF | parts by mass | 12.78 | ← | ← | ← | ← | ← | ← |
| Polyurethane solution |  |  | A5 | B5 | C5 | D5 | F5 | G5 | J5 |
| Solid content concentration |  | mass % | 20 | 20 | 20 | 20 | 20 | 20 | 20 |
| Viscosity of solution (25° C.) |  | Pa · s | 88 | 87 | 88 | 80 | 80 | 100 | 88 |
| Polyurethane film |  |  | A6 | B6 | C6 | D6 | F6 | G6 | J6 |
| Tensile physical property | Strength | MPa | 62 | 60 | 55 | 55 | 55 | 53 | 61 |
|  | Elongation | % | 700 | 690 | 670 | 760 | 760 | 580 | 690 |
| After heat-resistant NOx test | Appearance | Visual observation | Excellent | Excellent | Excellent | Excellent | Good | Excellent | Below average |
|  | Elongation | % | 640 | 630 | 610 | 680 | 640 | 450 | 630 |
|  | Elongation Retention | % | 91 | 91 | 91 | 89 | 84 | 78 | 91 |

|  |  |  | No. | | | |
| --- | --- | --- | --- | --- | --- | --- |
|  |  |  | Comp. Ex. 33 | Comp. Ex. 34 | Comp. Ex. 35 | Comp. Ex. 36 |
| Polyisocyanate component | 1,4-BIC |  | K | L | S | T |
|  | Trans isomer ratio | mol % | 82 | 82 | 67 | 97 |
|  | Compound represented by formula (1) content | ppm | 0.07 | 340 | 12 | 18 |
| Prepolymer formation | Prepolymer |  | k5 | l5 | s5 | t5 |
|  | Amount of isocyanate component | parts by mass | ← | ← | ← | ← |
|  | Amount of polyol component | UH-100 | parts by mass | ← | ← | ← | ← |
|  |  | UH-200 | parts by mass | ← | ← | ← | ← |
|  | Catalyst | 10% DBTDL/DMF | parts by mass | ← | ← | ← | ← |

TABLE 7-continued

| | | | | | | | |
|---|---|---|---|---|---|---|---|
| Chain extension reaction | Solvent | DMF | parts by mass | ← | ← | ← | ← |
| | Chain extender (Dividedly added) | Ethylene glycol | parts by mass | ← | ← | ← | ← |
| | | Ethylene glycol | parts by mass | ← | ← | ← | ← |
| | Catalyst | 10% DBTDL/DMF | parts by mass | ← | ← | ← | ← |
| | Solvent | DMF | parts by mass | ← | ← | ← | ← |
| | Stabilizer | IRGANOX 245 | parts by mass | ← | ← | ← | ← |
| | | Tinuvin234 | parts by mass | ← | ← | ← | ← |
| | | LA-72 | parts by mass | ← | ← | ← | ← |
| | Solvent | DMF | parts by mass | ← | ← | ← | ← |
| Polyurethane solution | | | | K5 | L5 | S5 | T5 |
| Solid content concentration | | | mass % | 20 | 20 | 20 | 20 |
| Viscosity of solution (25° C.) | | | Pa·s | 87 | 88 | 70 | 200 |
| Polyurethane film | | | | K6 | L6 | S6 | T6 |
| Tensile physical property | | Strength | MPa | 60 | 50 | 48 | 35 |
| | | Elongation | % | 680 | 600 | 850 | 400 |
| After heat-resistant NOx test | | Appearance | Visual observation | Good | Bad | Bad | Below average |
| | | Elongation | % | 610 | 500 | 610 | 300 |
| | | Elongation Retention | % | 90 | 83 | 72 | 75 |

The details of the abbreviations in Tables are shown below.

UH-100; ETERNACOLL UH-100, polycarbonatediol having a number average molecular weight of 1000 (manufactured by Ube industries, Ltd.)

UH-200; ETERNACOLL UH-200, polycarbonatediol having a number average molecular weight of 2000 (manufactured by Ube Industries, Ltd.)

DBTDL; dibutyltin dilaurate (manufactured by Wako Pure Chemical industries, Ltd.)

DMF; N,N-dimethylformamnide (manufactured by Wako Pure Chemical Industries, Ltd. Organic synthesis grade)

<Synthesis of Polyisocyanate Composition>

Example 40

17.1 parts by mass of TMP introduced into a dropping funnel was heated with a ribbon heater and dissolved. Then, a four-neck flask equipped with a stirrer, a thermometer, a reflux tube, and a nitrogen inlet tube was charged with 200 parts by mass of 1,4-BIC (A), and the temperature was increased while stirring in a nitrogen atmosphere to 75° C. Then, the dissolved TMP was dropped thereto taking for about 60 minutes. After the completion of dropping, the temperature was increased to 80° C., and reaction was continued until the isocyanate group concentration reached a calculated value. The produced reaction solution was allowed to pass through a thin-film distillation device (degree of vacuum 50 Pa, temperature 150° C.) to remove unreacted 1,4-BIC (A), and furthermore, ethyl acetate was added so that the solid content concentration was 75 mass %, thereby producing a polyisocyanate composition (A6).

The produced polyisocyanate composition (A6) had an isocyanate group concentration of 11.2%, a viscosity of 2300 mPa·s (25° C.), and a solid content concentration of 75.2%.

Examples 41 to 45 and Comparative Examples 37 to 41

Polyisocyanate compositions (B6 to T6) were produced in the same manner as in Example 40 based on the mixing formulation shown in Table 8.

<Synthesis and Evaluation of Two-Part Curing Polyurethane Resin>

To 341.3 parts by mass of acrylic polyol (OLESTER Q666 manufactured by Mitsui Chemicals, inc. hydroxyl number: 60 mgKOH/g) as a main component, 1.47 parts by mass of IRGANOX245 (heat-resistant stabilizer manufactured by BASF), 1.23 parts by mass of Tinuvin234 (ultraviolet absorber manufactured by BASF), and 0.74 parts by mass of Adeka StabLA-72 (HALS manufactured by ADEKA) were mixed and dissolved.

Thereafter, 150 parts by mass of the polyisocyanate composition (A6) produced in Example 40 was blended thereto, and furthermore, as a catalyst, 300 ppm of dibutyltin dilaurate relative to the solid content of the polyisocyanate composition (A6) was added thereto. Furthermore, butyl acetate was added thereto so that the solid content of acrylic polyol and polyisocyanate composition (A6) was 50 mass %, and the mixture was stirred at 23° C. for 180 seconds.

Next, the mixture liquid was applied on a glass substrate for hardness measurement, a polycarbonate substrate for adherence measurement, and a polypropylene substrate for tensile physical property measurement, and thereafter, cured by heat at 120° C. for 3 minutes. Further heating was conducted at 40° C. for 48 hours, thereby producing a polyurethane resin coating (A7) having a coating layer thickness of about 40 μm.

Examples 47 to 51 and Comparative Examples 42 to 46

Polyurethane resin coatings (B7 to T7) were produced in the same manner as in Example 46 based on the mixing formulation shown in Table 8.

Example 52

Cold/hot two-stage phosgenation method was performed under pressure using 1,5-diaminopentane as the ingredient.

That is, a pressurized reactor with jacket equipped with an electromagnetic induction stirrer, an automatic pressure regulating valve, a thermometer, a nitrogen inlet line, a phosgene inlet line, a condenser, and a material feed pump was charged with 2000 parts by mass of o-dichlorobenzene. Then, 2300 parts by mass of phosgene was added from the phosgene inlet line, and stirring was started. Cold water was allowed to go through the reactor jacket so that the internal temperature was kept to about 10° C. Then, a solution in which 400 parts by mass of 1,5-diaminopentane was dissolved in 2600 parts by mass of orthodichlorobenzene was fed with a feed pump taking 60 minutes, and cold phosgenation was started at 30° C. or less and normal pressure. After the completion of the feed, a light-brown white slurry was formed in the pressurized reactor.

Next, while increasing the temperature of the internal liquid of the reactor taking 60 minutes to 160° C., a pressure was applied to 0.25 MPa, and further, hot phosgenation was performed with a pressure of 0.25 MPa and a reaction temperature of 160° C. for 90 minutes. In the middle of the hot phosgenation, 1100 parts by mass of phosgene was added. Through the process of the hot phosgenation, the internal liquid of the pressurized reactor turned into a pale-brown transparent liquid. After completion of the hot-phosgenation reaction, nitrogen gas was introduced at 100 to 140° C. with a flow rate of 100 L/hour for degassing.

Next, after the solvent orthodichlorobenzene was distilled off under reduced pressure, 1,5-pentamethylene diisocyanate (hereinafter referred to as 1,5-PDI) was distilled away also under reduced pressure.

Next, the distilled 1,5-PDI was introduced into a four-neck flask equipped with a stirrer, a thermometer, a reflux tube, and a nitrogen inlet tube, and while introducing nitrogen, heated at 190° C. for 3 hours under normal pressure.

Next, the 1,5-PDI after the heat treatment was introduced into a glass-made flask, and using a distillation column (manufactured by Sibata Scientific Technology Ltd., trade name: distillation column K type) equipped with a distillation tube filled with four elements of packing (manufactured by Sumitomo Heavy Industries Ltd., trade name: Sumitomo/Sulzer Labo Packing EX), and a reflux ratio control timer, and using a rectifying device equipped with a condenser, rectification was performed with further refluxing under conditions of 127 to 132° C. and 2.7 KPa, thereby producing 480 parts by mass of 1,5-PDI.

The produced 1,5-PDI had a purity measured by gas chromatography of 99.9%.

A four-neck flask equipped with a stirrer, a thermometer, a reflux tube, and a nitrogen inlet tube was charged with 500 parts by mass of the above-described 1,5-PDI, and 50.0 parts by mass of trimethylolpropane (abbreviation: TMP) as a low molecular-weight polyol (equivalent ratio (NCO/OH)=5.8). The temperature was increased to 75° C. in a nitrogen atmosphere, and after confirming that trimethylolpropane was dissolved, the mixture was allowed to react at 83° C. until the isocyanate group concentration reached a calculated value (theoretical amount of unreacted isocyanate group. Ref. Table 1).

Next, the temperature of the reaction solution was decreased to 55° C., and thereafter, 350 parts by mass of an extraction solvent mixture (n-hexane/ethyl acetate=90/10 (mass ratio)) was added, and stirring was performed for 10 minutes. The mixture was allowed to stand for 10 minutes, and thereafter the extraction solvent layer was removed. The same extraction operation was repeated for 4 times.

Thereafter, the extraction solvent remained in the reaction solution was removed from the produced reaction solution while heating to 80° C. under reduced pressure, thereby producing a polyisocyanate composition.

Thereafter, a polyurethane resin coating (U8) was produced in the same manner as in Example 46 based on the mixing formulation shown in Table 8, using the produced polyisocyanate composition (1,5-PDI/TMP adduct) and the polyisocyanate composition (A6) produced in the above-described Example 40.

Evaluation

<Coating Hardness>

According to JIS-K5600-5-6 (1995), the pencil hardness at the time when a surface of the coating applied on the glass substrate was damaged was evaluated as coating hardness. The results are shown in Table 8.

<Adherence>

Adherence between the coating and the polycarbonate substrate was evaluated in conformity with ASTM D3359 (2007). The results are shown in Table 8.

In the Table, 5B represents that the coating peeled off by 0%, 3B represents that the coating peeled off by 5 to 15%, and 1B represents that the coating peeled off by 35 to 65%.

<Tensile Physical Property>

The coating was peeled off from the polypropylene substrate. The produced coating was punched out with a dumbbell to give a size of a width of 1 cm and a length of 10 cm, thereby producing a test sample. The tensile test was conducted using a tension and compression tester (Manufactured by INTESCO co., Ltd., Model205N) at 23° C., a tensile speed of 5 mm/min, and a distance between chucks of 50 mm for the test sample. The coating tensile strength at break (unit: MPa) and elongation (unit: %) were measured in this manner.

<Heat-Resistant NOx Yellowing Test>

The coating test piece, which was peeled off from the polypropylene substrate, was allowed to stand in a 90° C. hot air circulation oven for 1000 hours. Thereafter, the exposure test was conducted with a NOx concentration of 2,000 ppm for 2 hours in conformity with the test method in JIS L-0855 (2005). Thereafter, the test piece was further allowed to stand in a constant temperature and humidity container of 70° C. and 95% for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 8.

<Appearance>

Appearance of the test piece after the test was visually observed. The evaluation criteria are shown below. The results are shown in Table 8.

Excellent; No Change
Good; slightly changed
Below average; changed a little
Bad; changed The change means yellowing, becoming whitish, tack, and deformation.

TABLE 8

| | | | Ex. 40 | Ex. 41 | Ex. 42 | Ex. 43 | Ex. 44 | Ex. 45 | Ex. 40 | Comp. Ex. 37 | Comp. Ex. 38 | Comp. Ex. 39 | Comp. Ex. 40 | Comp. Ex. 41 |
|---|---|---|---|---|---|---|---|---|---|---|---|---|---|---|
| Polyisocyanate | 1,4-BIC Trans isomer | mol % | A 82 | B 82 | C 82 | D 72 | F 72 | G 93 | A 82 | J 82 | K 82 | L 82 | S 67 | T 97 |
| | Compound represented by formula (1) content | ppm | 15 | 0.19 | 270 | 12 | 250 | 20 | 15 | n.d. | 0.07 | 340 | 12 | 18 |
| TMP modification | Polyisocyanate composition Amount of polyisocyanate | parts by mass | A6 200.0 | B6 ↓ | C6 ↓ | D6 ↓ | F6 ↓ | G6 ↓ | A6 ↓ | J6 ↓ | K6 ↓ | L6 ↓ | S6 ↓ | T6 ↓ |
| | TMP | parts by mass | 17.1 | ↓ | ↓ | ↓ | ↓ | ↓ | ↓ | ↓ | ↓ | ↓ | ↓ | ↓ |
| | Isocyanate group concentration | mass % | 11.2 | ↓ | ↓ | ↓ | ↓ | ↓ | ↓ | ↓ | ↓ | ↓ | ↓ | ↓ |
| | Solid content concentration | mass % | 75.2 | ↓ | ↓ | ↓ | ↓ | ↓ | ↓ | ↓ | ↓ | ↓ | ↓ | ↓ |
| | Viscosity@25° C. | mPa·s | 2300 | ↓ | ↓ | ↓ | ↓ | ↓ | ↓ | ↓ | ↓ | ↓ | ↓ | ↓ |

| | | | Ex. 46 | Ex. 47 | Ex. 48 | Ex. 49 | Ex. 50 | Ex. 51 | Ex. 52 | Comp. Ex. 42 | Comp. Ex. 43 | Comp. Ex. 44 | Comp. Ex. 45 | Comp. Ex. 46 |
|---|---|---|---|---|---|---|---|---|---|---|---|---|---|---|
| Coating formation | Polyisocyanate composition type Amount of polyisocyanate composition used | parts by mass | A6 150 | B6 ↓ | C6 ↓ | D6 ↓ | F6 ↓ | G6 ↓ | A6 75.00 | J6 ↓ | K6 ↓ | L6 ↓ | S6 ↓ | T6 ↓ |
| | 1,5-PDI-TMP adduct | parts by mass | — | — | — | — | — | — | 41.79 | — | — | — | — | — |
| | Polyol OLESTER | parts by mass | 341.3 | ↓ | ↓ | ↓ | ↓ | ↓ | 341.3 | ↓ | ↓ | ↓ | ↓ | ↓ |

TABLE 8-continued

| component Stabilizer | Q666 IRGANOX245 | mass parts by mass | 1.47 | ↓ | ↓ | ↓ | ↓ | ↓ | ↓ | ↓ | ↓ | ↓ |
|---|---|---|---|---|---|---|---|---|---|---|---|---|
| | Tinuvin234 | mass parts by mass | 1.23 | ↓ | ↓ | ↓ | ↓ | 1.37 | ↓ | ↓ | ↓ | ↓ |
| | LA-72 | mass parts by mass | 0.74 | ↓ | ↓ | ↓ | ↓ | 1.15 | ↓ | ↓ | ↓ | ↓ |
| | | | | | | | | 0.69 | | | | |
| Coating | | | A7 | B7 | C7 | D7 | F7 | G7 | U8 | J7 | K7 | L7 | S7 | T7 |
| Coating hardness | | | H | H | H | H | H | F | F | H | H | F | H | HB |
| Adhesion | | | 5B | 5B | 5B | 5B | 5B | 5B | 5B | 5B | 5B | 5B | 5B | 5B |
| Tensile physical property | Strength | MPa | 45 | 43 | 42 | 48 | 48 | 41 | 38 | 44 | 44 | 42 | 50 | 35 |
| | Elongation | % | 5.8 | 5.8 | 5.7 | 6.2 | 6.2 | 5.0 | 8.0 | 5.6 | 5.8 | 5.5 | 6.4 | 4.3 |
| After heat-resistant NOx test | Appearance | Visual observation | Excellent | Excellent | Excellent | Excellent | Excellent | Excellent | Excellent | Below average | Good | Bad | Excellent | Below average |
| | Coating hardness | | H | H | H | H | F | F | F | H | H | B | B | B |
| | Elongation | % | 5.2 | 5.2 | 5.1 | 5.4 | 5.2 | 4.4 | 7.3 | 4.9 | 5.2 | 4.5 | 5.1 | 3.6 |
| | Elongation Retention | % | 90 | 90 | 89 | 87 | 84 | 88 | 91 | 88 | 90 | 82 | 80 | 84 |

The details of the abbreviations in Tables are shown below.

TMP; trimethylolpropane (manufactured by Wako Pure Chemical Industries, Ltd.)

<Preparation and Evaluation of Polyurethane Foam>

Example 53

Based on the mixing formulation of Table 9, EP-950P (polyether polyol, manufactured by Mitsui Chemicals, Inc.), triethanol amine (TEOA)(manufactured by Mitsui Chemicals, Inc.), diethanol amine (DEOA)(manufactured by Mitsui Chemicals, Inc.), ion-exchange water, 33LV (amine catalyst, manufactured by Air Products and Chemicals, Inc.), Niax A1 (amine catalyst, manufactured by Momentive Performance Materials Inc.), UL-28 (amine catalyst, manufactured by Momentive Performance Materials Inc.), Stanoct (tin octylate, manufactured by API Corporation), Y10366 (silicone-made foam stabilizer, manufactured by Momentive Performance Materials Inc.), Tinuvin765 (HALS manufactured by BASF), and JP-308; tris(2-ethylhexyl)phosphite (manufactured by JOHOKU CHEMICAL CO., LTD) were weighed, and stirred to be mixed until becoming homogenous, thereby preparing a resin premix. Then, the produced resin premix was adjusted to 23° C.

Thereafter, 151.9 parts by mass of 1,4-BAC (A) was added to the resin premix, and the mixture was stirred for 15 seconds with a hand mixer (number of revolution 5000 rpm) to prepare a polyurethane foam composition, and immediately after the preparation, the polyurethane foam composition was put into a wooden box right away to form a foam. A polyurethane foam (A8) was produced in this manner.

Examples 54 to 58 and Comparative Examples 47 to 51

Polyurethane foams (B8 to T8) were prepared in the same manner as in Example 53 based on the mixing formulation shown in Table 9. Foams were produced in Examples 54 to 58 and Comparative Examples 47 to 50. Meanwhile, in Comparative Example 51, cells were collapsed during foaming, and a foam was not produced.

Evaluation

<Shrinkage>

The polyurethane foams were allowed to stand for 2 days in a room having a temperature of 23° C. and a relative humidity of 55%, and the polyurethane foams after they were allowed to stand were visually observed for presence or absence of shrinkage. Those foams with no shrinkage were evaluated as Excellent, and those foams with shrinkage was evaluated as BAD. The results are shown in Table 9.

<Apparent Density>

A rectangular parallelepiped having a size of 10×10×5 cm was cut out from a center portion (core) of the polyurethane foam after shrinkage evaluation to prepare a measurement sample, and thereafter, the apparent density (unit: $kg/m^3$) of the measurement sample was measured in conformity with JIS K7222 (2005). The results are shown in Table 9.

<Foam Hardness 25% CLD>

The foam hardness (unit: $N/314\ cm^2$) was measured in conformity with method D described in JIS K-6400-2 (2012). The results are shown in Table 9.

<Air Flow Value>

The polyurethane foam after the shrinkage evaluation was cut into a sheet having a thickness of 10 mm, and then thereafter the sheet was crushed (crush conditions: polyurethane foam passes through two rollers (space 0.2 mm)) to produce an air flow value measurement sample, and thereafter, the air flow value (unit: $cc/cm^2/s$) of the air flow value measurement sample was measured in conformity with method A described in JIS K6400-7 (2004). The results are shown in Table 9.

<Tensile Physical Property>

The tensile strength (unit: kPa) and elongation (unit: %) were measured by the method described in JIS K-6400 (2004). The results are shown in Table 9.

<Heat-Resistant NOx Yellowing Test>

The polyurethane foam test piece was allowed to stand in a 80° C. hot air circulation oven for 1000 hours. Thereafter, the exposure test was conducted with a NOx concentration of 2,000 ppm for 2 hours in conformity with the test method in JIS L-0855 (2005). Thereafter, the test piece was further allowed to stand in a constant temperature and humidity container of 70° C. and 95% for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 9.

<Appearance>

Appearance of the test piece after the test was visually observed. The evaluation criteria are shown below. The results are shown in Table 9.

Excellent; No Change

Good; slightly changed

Below average; changed a little

Bad; changed

The change means yellowing, becoming whitish, tack, and deformation.

TABLE 9

| | | | Ex. 53 | Ex. 54 | Ex. 55 | Ex. 56 | Ex. 57 | Ex. 58 | Comp. Ex. 47 | Comp. Ex. 48 | Comp. Ex. 49 | Comp. Ex. 50 | Comp. Ex. 51 |
|---|---|---|---|---|---|---|---|---|---|---|---|---|---|
| Polyisocyanate component | 1,4-BIC | mol % | A 82 | B 82 | C 82 | D 72 | F 72 | G 93 | J 82 | K 82 | L 82 | S 67 | T 97 |
| | Trans isomer ratio | | | | | | | | | | | | |
| | Compound represented by formula (1) content | ppm | 15 | 0.19 | 270 | 12 | 250 | 20 | n.d. | 0.07 | 340 | 12 | 18 |
| Resin premix preparation | Amount of isocyanate component | parts by mass | 151.9 | ↓ | ↓ | ↓ | ↓ | ↓ | ↓ | ↓ | ↓ | ↓ | ↓ |
| | Amount of active hydrogen compound | EP-950P | parts by mass | 350.0 | | | | | | | | | | |
| | | TEOA | parts by mass | 7.0 | | | | | | | | | | |
| | | DEOA | parts by mass | 17.5 | | | | | | | | | | |
| | Foaming agent | Ion-exchange water | parts by mass | 7.0 | | | | | | | | | | |
| | Catalyst | 33LV | parts by mass | 1.8 | | | | | | | | | | |
| | | UL-28 | parts by mass | 0.5 | | | | | | | | | | |
| | | Stanoct | parts by mass | 1.1 | | | | | | | | | | |
| | Foam stabilizer | Y10366 | parts by mass | 3.50 | | | | | | | | | | |
| | | Tinuvin765 | parts by mass | 4.20 | | | | | | | | | | |
| | Stabilizer | JP-308 | parts by mass | 3.50 | | | | | | | | | | |
| Polyurethane foam | Shrinkage | | A8 Excellent | B8 Excellent | C8 Excellent | D8 Excellent | F8 Excellent | G8 Excellent | J8 Excellent | K8 Excellent | L8 Excellent | S8 Good | T8 —(Collapse) |
| | Apparent density | kg/m² | 52 | 52 | 52 | 49 | 49 | 55 | 52 | 57 | 52 | 48 | — |
| | Hardness (25% CLD) | N/100 cm² | 4.3 | 4.3 | 4.3 | 4 | 4 | 4.5 | 4.3 | 3.4 | 3.4 | 3.8 | — |
| | Air flow value | cc/cm²/s | 80 | 82 | 81 | 65 | 65 | 85 | 79 | 77 | 75 | 55 | — |
| | Tensile physical property | Strength | MPa | 92 | 88 | 90 | 95 | 95 | 85 | 90 | 91 | 92 | 95 | — |
| | | Elongation | % | 95 | 90 | 92 | 98 | 98 | 88 | 93 | 92 | 92 | 100 | — |
| | Appearance | Visual observation | Excellent | Excellent | Excellent | Excellent | Good | Excellent | Below average | Good | Bad | Bad | — |
| | After heat-resistant NOx test | Elongation | % | 78 | 75 | 73 | 78 | 75 | 68 | 75 | 75 | 66 | 75 | — |
| | | Elongation Retention | % | 82 | 83 | 79 | 80 | 77 | 77 | 81 | 82 | 72 | 75 | — |

The details of the abbreviations in Tables are shown below.

EP-950P; polyether polyol (manufactured by Mitsui Chemicals, Inc.)

TEOA; triethanol amine (manufactured by Mitsui Chemicals, Inc.)

DEOA; diethanol amine (manufactured by Mitsui Chemicals, Inc.)

33LV; amine catalyst (manufactured by Air Products and Chemicals, Inc.)

Niax A1; amine catalyst (manufactured by Momentive Performance Materials Inc.)

UL-28; amine catalyst (manufactured by Momentive Performance Materials Inc.)

Stanoct; tin octylate (manufactured by API Corporation)

Y110366; silicone foam stabilizer (manufactured by Momentive Performance Materials Inc.)

Tinuvin765; hindered amine light stabilizer (HALS) (Manufactured by BASF)

JP-308; tris(2-ethylhexyl)phosphite (manufactured by JOHIOKU CHEMICAL CO., LTD)

<Preparation and Evaluation Polyurethane Fiber>

Synthesis of Prepolymer (a9)

A four-neck flask equipped with a stirrer, a thermometer, a reflux tube, and a nitrogen inlet tube was charged with 24.9 parts by mass of 1,4-BIC (A) and 100.0 parts by mass of PEG2000U (polyethylene glycol having a number average molecular weight of 2000, manufactured by NOF CORPORATION) dehydrated in advance under reduced pressure, and the mixture was stirred in a nitrogen atmosphere at 80° C. for 1 hour. A solution, in which 0.015 parts by mass of bismuth octylate (catalyst, trade name: NEOSTANN U-600, manufactured by Nitto Kasei) was diluted with DINA (manufactured by J-PLUS Co., Ltd.) to 4 mass %, was further added, and the mixture was allowed to react so that the isocyanate group content reached 5.23 mass %, thereby producing an isocyanate group-terminated polyurethane prepolymer (a9)(simply called prepolymer (a9) in the following).

Synthesis of Polyurethane Elastomer (A9)

A stainless steel container was charged with 100 parts by mass of prepolymer (a9) having a preadjusted temperature of 80° C., 1.06 parts by mass of GA-80 (heat-resistant stabilizer manufactured by Sumitomo Chemical Co., Ltd.), 0.32 parts by mass of Tinuvin234 (ultraviolet absorber manufactured by BASF), and 0.32 parts by mass of Adeka StabLA-72 (HALS manufactured by ADEKA), and the mixture was stirred and mixed using a high-speed disper at 1000 rpm for about 2 minutes. Then, as a chain extender, 5.34 parts by mass of 1,4-BD having a preadjusted temperature of 80° C., 0.013 parts by mass of a solution in which bismuth octylate (catalyst, trade name: NEOSTANN U-600, manufactured by Nitto Kasei) was diluted with DINA (manufactured by J-PLUS Co., Ltd.) to 4 mass %, and the mixture was stirred and mixed using a high-speed disper at 1000 rpm for about 10 minutes.

Next, the reaction mixture liquid was poured into a SUS-made vat having a preadjusted temperature of 150° C., and reaction was performed at 150° C. for 1 hour, and then at 100° C. for 23 hours, thereby producing a polyurethane elastomer (A9).

Thereafter, the polyurethane elastomer (A9) was taken out from the vat, and aged under constant temperature and humidity conditions of a room temperature of 23° C. and a relative humidity of 55% for 7 days.

The produced polyurethane elastomer (A9) was cut into dice with a bale cutter, and the diced resin was ground with a grinder. The ground pellets were dried under a nitrogen flow at 80° C. for a whole day and night. Strands were extruded using a monoaxial extruder (model: SZW40-28MG, manufactured by Technovel Corporation) with a cylinder temperature in the range of 150 to 245° C., and they were cut, thereby producing polyurethane elastomer (A9) pellets. The produced pellets were dried under a nitrogen flow at 80° C. for a whole day and night.

The molten resin extruded for measurement of sear viscosity in accordance with JIS K 7199 (1999) was wound up mechanically, thereby producing polyurethane fiber (A9).

To be specific, the polyurethane elastomer (A9) pellets were dried under reduced pressure at 80° C. for 15 hours. Using a capillary rheometer (CAPIROGRAPH 1C manufactured by Toyo Seiki Seisaku-sho), a barrel (internal diameter: 9.55 mm) was charged with the dried pellets, and the dried pellets were melted at 220° C. for 3 minutes as preliminary heating, and thereafter extruded at a piston rate of 5 mm/min. The molten resin extruded from the nozzle (diameter 1 mm, length 10 mm) of the distal end of the barrel was wound using a filament winding machine (manufactured by Imoto Machinery Co., Ltd.), thereby winding up a roll having a diameter of 90 mm at 700 rpm.

Examples 60 to 64 and Comparative Examples 52 to 56

Polyurethane fiber (B9 to T9) was produced in the same manner as in Example 59 based on the mixing formulation shown in Table 10.

<Spinning Characteristics>

The average diameter of the filament, effective spinning time (net spinning time excluding the time while stopping the winding based on, for example, filament breakage) for 10 minutes, the number of filament breakage, and the degree of the filament agglutination after the winding were evaluated based on the following criteria.

The filament can be taken out quickly from the winding roll . . . Excellent

Slight agglutination observed but filament could be taken out . . . Below average The filaments agglutinated from each other, and filament could not be taken out . . . Bad <Heat-Resistant NOx Yellowing Test>, The produced polyurethane fiber in an amount of about 3 g was wound around the sample holder described in JIS L-0855 (2005), and allowed to stand in a 90° C. hot air circulation oven for 1000 hours. Thereafter, the exposure test was conducted with a NOx concentration of 2,000 ppm for 2 hours in conformity with the test method in JIS L-0855 (2005). Thereafter, the test piece was further allowed to stand in a constant temperature and humidity container of 80° C. and 95% for 24 hours. The appearance after being allowed to stand was observed visually.

<Appearance>

Appearance of the test piece after the test was visually observed. The evaluation criteria are shown below. The results are shown in Table 10.

Excellent; No Change

Good; slightly changed

Below average; changed a little

Bad; changed

The change means yellowing, becoming whitish, tack, and deformation.

TABLE 10

|  |  |  |  | No. | | | | | |
|---|---|---|---|---|---|---|---|---|---|
|  |  |  |  | Ex. 59 | Ex. 60 | Ex. 61 | Ex. 62 | Ex. 63 | Ex. 64 |
| Polyisocyanate component | 1,4-BIC |  |  | A | B | C | D | F | G |
|  | Trans isomer ratio | mol % |  | 82 | 82 | 82 | 72 | 72 | 93 |
|  | Compound represented by formula (1) content | ppm |  | 15 | 0.19 | 270 | 12 | 250 | 20 |
| Prepolymer formation | Prepolymer |  |  | a9 | b9 | c9 | d9 | f9 | g9 |
|  | Amount of isocyanate component |  | Parts by mass | 24.9 | ← | ← | ← | ← | ← |
|  | Amount of polyol component | PEG2000U | Parts by mass | 100.0 | ← | ← | ← | ← | ← |
|  | Catalyst | 4% U-600/DINA | Parts by mass | 0.015 | ← | ← | ← | ← | ← |
|  | Prepolymer total amount |  | Parts by mass | 124.9 | ← | ← | ← | ← | ← |
| Chain extension reaction | Amount of Prepolymer used |  | Parts by mass | 100.0 | ← | ← | ← | ← | ← |
|  | Chain extender | 1,4-BD | Parts by mass | 5.34 | ← | ← | ← | ← | ← |
|  | Catalyst | 4% U-600/DINA | Parts by mass | 0.013 | ← | ← | ← | ← | ← |
|  | Stabilizer | GA-80 | Parts by mass | 1.06 | ← | ← | ← | ← | ← |
|  |  | Tinuvin234 | Parts by mass | 0.32 | ← | ← | ← | ← | ← |
|  |  | Adeka Stab LA-72 | Parts by mass | 0.32 | ← | ← | ← | ← | ← |
| Polyurethane elastomer |  |  |  | A9 | B9 | C9 | D9 | F9 | G9 |
| Hardness |  |  | Shore A | 85 | 85 | 85 | 83 | 83 | 87 |
| Polyurethane fiber |  |  |  | A9 | B9 | C9 | D9 | F9 | G9 |
| Spinning | Breakage |  | Times | 0 | 0 | 0 | 0 | 2 | 3 |
|  | Agglutination status |  |  | Excellent | Excellent | Excellent | Excellent | Good | Excellent |
| After heat-resistant NOx test | Appearance |  | Visual observation | Excellent | Excellent | Excellent | Excellent | Good | Excellent |

|  |  |  |  | No. | | | | |
|---|---|---|---|---|---|---|---|---|
|  |  |  |  | Comp. Ex. 52 | Comp. Ex. 53 | Comp. Ex. 54 | Comp. Ex. 55 | Comp. Ex. 56 |
| Polyisocyanate component | 1,4-BIC |  |  | J | K | L | S | T |
|  | Trans isomer ratio | mol % |  | 82 | 82 | 82 | 67 | 97 |
|  | Compound represented by formula (1) content | ppm |  | n.d. | 0.07 | 340 | 12 | 18 |
| Prepolymer formation | Prepolymer |  |  | j9 | k9 | l9 | s9 | t9 |
|  | Amount of isocyanate component |  | Parts by mass | ← | ← | ← | ← | ← |
|  | Amount of polyol component | PEG2000U | Parts by mass | ← | ← | ← | ← | ← |
|  | Catalyst | 4% U-600/DINA | Parts by mass | ← | ← | ← | ← | ← |
|  | Prepolymer total amount |  | Parts by mass | ← | ← | ← | ← | ← |
| Chain extension reaction | Amount of Prepolymer used |  | Parts by mass | ← | ← | ← | ← | ← |
|  | Chain extender | 1,4-BD | Parts by mass | ← | ← | ← | ← | ← |

TABLE 10-continued

| | | | | | | | | |
|---|---|---|---|---|---|---|---|---|
| Catalyst | 4% U-600/DINA | Parts by mass | ← | ← | ← | ← | ← |
| Stabilizer | GA-80 | Parts by mass | ← | ← | ← | ← | ← |
| | Tinuvin234 | Parts by mass | ← | ← | ← | ← | ← |
| | Adeka Stab LA-72 | Parts by mass | ← | ← | ← | ← | ← |
| Polyurethane elastomer | | | J9 | K9 | L9 | S9 | T9 |
| Hardness | | Shore A | 85 | 85 | 85 | 80 | 90 |
| Polyurethane fiber | | | J9 | K9 | L9 | S9 | T9 |
| Spinning | Breakage | Times | 0 | 0 | 0 | 3 | >10 |
| | Agglutination status | | Below average | Good | Excellent | Below average | Excellent |
| After heat-resistant NOx test | Appearance | Visual observation | Excellent | Excellent | Bad | Bad | Below average |

<Preparation of Thermosetting Polyurethane Urea>

Example 65

A reaction vessel equipped with a nitrogen inlet tube, a thermometer, a vacuum line, and a stirrer was charged with 280.2 parts by mass of 1,4-BIC (A), 331.3 parts by mass of polytetramethylene ether glycol (trade name: PolyTHF1000S, manufactured by BASF Japan) having a number average molecular weight of 1000, 244.8 parts by mass of polytetramethylene ether glycol having a number average molecular weight of 2000 (trade name: PolyTHF2000S, manufactured by BASF Japan), 2.57 parts by mass of IRGANOX245 (heat-resistant stabilizer manufactured by BASF), 1.71 parts by mass of Tinuvin234 (ultraviolet absorber manufactured by BASF), and 1.28 parts by mass of Tinuvin765 (HALS manufactured by BASF), and the mixture was stirred in a nitrogen atmosphere at 80 to 85° C. for 1 hour. Furthermore, 0.011 parts by mass of a solution in which dibutyltin dilaurate was diluted with diisononyl adipate (manufactured by J-PLUS Co., Ltd.) to 4 mass % was introduced thereto. Thereafter, stirring was performed at 80° C., and reaction was performed until the isocyanate group content reached 15.14 mass %. Then, BYK088 (antifoaming agent manufactured by BYK Japan KK) was added, and the stirring was continued for 10 minutes. Thereafter, defoaming was performed under vacuum, thereby producing an isocyanate group-terminated prepolymer.

Thereafter, a reaction vessel equipped with a nitrogen inlet tube, a thermometer, a vacuum line, and a stirrer was charged with 123.75 parts by mass of 4,4'-methylenebis[N-(1-methylpropyl)cyclohexaneamine](trade name: CLEARLINK1000, manufactured by Dorf Ketal Chemicals) and 14.27 parts by mass of 4,4'-methylenebis(cyclohexylamine) (trade name: WONDAMINE HM, manufactured by New Japan Chemical co., ltd.), and the airspace portion in the container was sufficiently replaced with nitrogen, and thereafter the mixture was stirred at 20 to 35° C. for about 15 minutes. Thereafter, defoaming was performed under vacuum, thereby producing a low molecular-weight active hydrogen group-containing component (amine curing agent).

Then, using two small precision gear pumps, the isocyanate group-terminated prepolymer heated to 60° C. and the low molecular-weight active hydrogen group-containing component (amine curing agent) of room temperature were separately fed into one static mixer (SM632 type: number of elements=32, internal diameter=7 mm, total length=241 mm) so that the isocyanate group-terminated prepolymer and the low molecular-weight active hydrogen group-containing component were mixed homogenously by passing through the static mixer.

The flow rates of the two liquids were set in accordance with the mixing formulation shown in Table 11. The mixture liquid discharged from the tip end portion of the static mixer was poured into a mold heated to a temperature of 60° C. and having a thickness of 2 mm, and the mixture was allowed to react at 60° C. for 5 minutes. Thereafter, the cured product was taken out from the mold, and after further performing reaction at 60° C. for 24 hours, aged under constant temperature and humidity conditions of 23° C. and a relative humidity of 50% for 7 days, thereby producing a thermosetting polyurethane urea resin sheet (A10)(molded article).

Examples 66 to 70 and Comparative Examples 57 to 61

Thermosetting polyurethane urea resin sheets (B10 to T10) were produced in the same manner as in Example 65 based on the mixing formulation shown in Table 11.

<Hardness: Shore D>

Shore D hardness was measured in accordance with "JIS K-7311 Testing methods for thermoplastic polyurethane elastomers" (1995). The results are shown in Table 11 in numeral values.

<Tensile Physical Property>

A tensile test was performed using the produced sheet in conformity with the method described in "JIS K-7311 Testing methods for thermoplastic polyurethane elastomers" (1995). A test piece was punched out with a JIS-3 dumbbell, and the tensile strength (unit: MPa) and the elongation (unit: %) were measured using a tensile tester (manufactured by Toyoseiki kogyo Co., Ltd., trade name: all-automatic rubber tensile tester TYPE: AE-CT) under the conditions of a bench mark distance of 20 mm and a tensile speed of 300 mm/min. The results are shown in Table 11.

<Heat-Resistant NOx Yellowing Test>

The thermosetting polyurethane urea test piece was placed on a SUS-made mirror plate and allowed to stand in a 80° C. hot air circulation oven for 1000 hours. After the completion of the test, the test piece was aged in a constant temperature room of 23° C. and 50% RH for 2 days, and then removed from the mirror plate. Thereafter, the exposure test was conducted with a NOx concentration of 2,000 ppm for 2 hours in conformity with the test method in JIS L-0855 (2005). Thereafter, the test piece was further allowed to stand in a constant temperature and humidity container of 70° C. and 95% for 24 hours. The appearance after being allowed to stand was observed visually.

After further drying the test piece under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 11.

<Appearance>

Appearance of the test piece after the test was visually observed. The evaluation criteria are shown below. The results are shown in Table 11.

Excellent; No Change
Good; slightly changed
Below average; changed a little
Bad; changed The change means yellowing, becoming whitish, tack, and deformation.

TABLE 11

|  |  |  |  | No. | | | | | |
|---|---|---|---|---|---|---|---|---|---|
|  |  |  |  | Ex. 65 | Ex. 66 | Ex. 67 | Ex. 68 | Ex. 69 | Ex. 70 |
| Polyisocyanate component |  | 1,4-BIC |  | A | B | C | D | F | G |
|  |  | Trans isomer ratio | mol % | 82 | 82 | 82 | 72 | 72 | 93 |
|  |  | Compound represented by formula (1) content | ppm | 15 | 0.19 | 270 | 12 | 250 | 20 |
| Prepolymer formation | Prepolymer |  |  | a10 | b10 | c10 | d10 | f10 | g10 |
|  | Amount of isocyanate component |  | Parts by mass | 280.2 | ← | ← | ← | ← | ← |
|  | Amount of polyol component | PolyTHF1000 | Parts by mass | 331.3 | ← | ← | ← | ← | ← |
|  |  | PolyTHF2000 | Parts by mass | 244.8 | ← | ← | ← | ← | ← |
|  | Catalyst | 4% DBTDL/DINA | Parts by mass | 0.011 | ← | ← | ← | ← | ← |
|  | Stabilizer | IRGANOX245 | Parts by mass | 2.57 | ← | ← | ← | ← | ← |
|  |  | Tinuvin765 | Parts by mass | 1.28 | ← | ← | ← | ← | ← |
|  |  | Tinuvin234 | Parts by mass | 1.71 | ← | ← | ← | ← | ← |
|  | Prepolyer total amount |  | Parts by mass | 862.0 | ← | ← | ← | ← | ← |
| Chain extender reaction | Amount of Prepolymer used |  | Parts by mass | 862.0 | ← | ← | ← | ← | ← |
|  | Chain extender | ClearLink1000 | Parts by mass | 123.75 | ← | ← | ← | ← | ← |
|  |  | WONDAMINEHM | Parts by mass | 14.27 | ← | ← | ← | ← | ← |
| Polyurethane urea |  |  |  | A10 | B10 | C10 | D10 | F10 | G10 |
| Hardness |  |  | shoreD | 55 | 55 | 55 | 53 | 53 | 57 |
| Tensile physical property |  | Strength | MPa | 38 | 38 | 39 | 37 | 37 | 38 |
|  |  | Elongation | % | 520 | 500 | 470 | 530 | 500 | 480 |
| After heat-resistant NOx test |  | Appearance | Visual observation | Excellent | Excellent | Excellent | Good | Good | Excellent |
|  |  | Elongation | % | 500 | 470 | 420 | 440 | 450 | 450 |
|  |  | Elongation Retention | % | 96 | 94 | 89 | 83 | 90 | 94 |

|  |  |  |  | No. | | | | |
|---|---|---|---|---|---|---|---|---|
|  |  |  |  | Comp. Ex. 57 | Comp. Ex. 58 | Comp. Ex. 59 | Comp. Ex. 60 | Comp. Ex. 61 |
| Polyisocyanate component |  | 1,4-BIC |  | J | K | L | S | T |
|  |  | Trans isomer ratio | mol % | 82 | 82 | 82 | 67 | 97 |
|  |  | Compound represented by formula (1) content | ppm | n.d. | 0.07 | 340 | 12 | 18 |
| Prepolymer formation | Prepolymer |  |  | j10 | k10 | l10 | s10 | t10 |
|  | Amount of isocyanate component |  | Parts by mass | ← | ← | ← | ← | ← |
|  | Amount of polyol component | PolyTHF1000 | Parts by mass | ← | ← | ← | ← | ← |
|  |  | PolyTHF2000 | Parts by mass | ← | ← | ← | ← | ← |

TABLE 11-continued

| | | | | | | | | |
|---|---|---|---|---|---|---|---|---|
| | Catalyst | 4% DBTDL/DINA | Parts by mass | ← | ← | ← | ← | ← |
| | Stabilizer | IRGANOX245 | Parts by mass | ← | ← | ← | ← | ← |
| | | Tinuvin765 | Parts by mass | ← | ← | ← | ← | ← |
| | | Tinuvin234 | Parts by mass | ← | ← | ← | ← | ← |
| | Prepolyer total amount | | Parts by mass | ← | ← | ← | ← | ← |
| Chain extender reaction | Amount of Prepolymer used | | Parts by mass | ← | ← | ← | ← | ← |
| | Chain extender | ClearLink1000 | Parts by mass | ← | ← | ← | ← | ← |
| | | WONDAMINEHM | Parts by mass | ← | ← | ← | ← | ← |
| Polyurethane urea | | | | J10 | K10 | L10 | S10 | T10 |
| Hardness | | | shoreD | 55 | 55 | 55 | 52 | 59 |
| Tensile physical property | | Strength | MPa | 39 | 38 | 38 | 34 | 30 |
| | | Elongation | % | 510 | 500 | 420 | 560 | 320 |
| After heat-resistant NOx test | | Appearance | Visual observation | Below average | Good | Bad | Bad | Excellent |
| | | Elongation | % | 480 | 470 | 360 | 360 | 250 |
| | | Elongation Retention | % | 94 | 94 | 86 | 64 | 78 |

<Synthesis and Evaluation of Moisture Permeable Polyurethane Elastomer (TPU)>

Example 71

Synthesis of Prepolymer

A four-neck flask equipped with a stirrer, a thermometer, a reflux tube, and a nitrogen inlet tube was charged with 228.7 parts by mass of 1,4-BIC (A), and 683.5 parts by mass of PEG2000U (polyethylene glycol having a number average molecular weight of 2000, manufactured by NOF CORPORATION) dehydrated in advance under reduced pressure, and the mixture was stirred in a nitrogen atmosphere at 80° C. for 1 hour. Thereafter, 0.110 parts by mass of a solution in which bismuth octylate (catalyst, trade name: NEOSTANN U-600, manufactured by Nitto Kasei) was diluted with DINA (manufactured by J-PLUS Co., Ltd.) to 4 mass % in advance was added. Reaction was then performed at 80° C. until the isocyanate group content reached 7.7 mass %, thereby producing an isocyanate group-terminated polyurethane prepolymer (a1)(simply called prepolymer (a11) in the following).

Preparation of Polyurethane Elastomer (A11)

A stainless steel container was charged with 900 parts by mass of the prepolymer (a11) having a preadjusted temperature of 80° C., 9.92 parts by mass of IRGANOX245 (heat-resistant stabilizer manufactured by BASF), 2.95 parts by mass of Tinuvin234 (ultraviolet absorber manufactured by BASF), and 2.95 parts by mass of Adeka StabLA-72 (HALS manufactured by ADEKA), and the mixture was stirred and mixed using a high-speed disper at 1000 rpm for about 2 minutes. Then, as a chain extender, 71.72 parts by mass of 1,4-BD having a preadjusted temperature of 80° C. was added thereto, and the mixture was stirred and mixed using a high-speed disper at 1000 rpm for about 10 minutes.

Next, the reaction mixture liquid was poured into a SUS-made vat having a preadjusted temperature of 150° C., and reaction was performed at 150° C. for 1 hour, and then at 100° C. for 23 hours, thereby producing a polyurethane elastomer (A11).

Thereafter, the polyurethane elastomer (A11) was removed from the vat, and aged under constant temperature and humidity conditions of a room temperature of 23° C. and a relative humidity of 55% for 7 days.

The produced polyurethane elastomer (A11) was cut into dice with a bale cutter, and the diced resin was ground with a grinder. The ground pellets were dried under a nitrogen flow at 80° C. for a whole day and night. Strands were extruded using a monoaxial extruder (model: SZW40-28MG, manufactured by Technovel Corporation) with a cylinder temperature in the range of 150 to 245° C., and they were cut, thereby producing polyurethane elastomer (A11) pellets. The produced pellets were further dried under nitrogen flow at 80° C. for a whole day and night.

Next, injection molding was performed using an injection molding machine (model: NEX-140, manufactured by NISSEI PLASTIC INDUSTRIAL CO., LTD.) under the following conditions setting the screw number of revolution to 80 rpm and the barrel temperature to 150 to 235° C.: a mold temperature of 20° C., injection time of 10 seconds, an injection rate of 60 mm/s, and cooling time of 45 seconds. The produced sheet having a thickness of 2 mm was aged under constant temperature and humidity conditions of a room temperature of 23° C. and a relative humidity of 55% for 7 days, thereby producing an elastomer sheet.

Meanwhile, a film having a thickness of 20 μm was formed/molded with a monoaxial extruder equipped with T-die from the produced pellets, at a screw number of revolution of 20 rpm and a cylinder temperature in the range of 200 to 250° C.

The produced film (thickness 20 μm) was aged under constant temperature and humidity conditions of a room temperature of 23° C. and a relative humidity of 50% for 7 days.

Evaluation

<Hardness: Shore A>

Shore A hardness was measured using the elastomer sheet in accordance with "JIS K-7311 Testing methods for thermoplastic polyurethane elastomers" (1995). The results are shown in Table 12.

<Tensile Physical Property>

A tensile test was performed using the produced elastomer sheet in accordance with the method described in "JIS K-7311 Testing methods for thermoplastic polyurethane elastomers" (1995). The test piece was punched out with a JIS-3 dumbbell, and the tensile strength at break (unit: MPa) and the elongation (unit: %) were measured using a tensile tester (manufactured by Toyoseiki kogyo Co., Ltd., trade name: all-automatic rubber tensile tester TYPE: AE-CT) under the following conditions: a bench mark distance of 20 mm and a tensile speed of 300 mm/min. The results are shown in Table 12.

<Water Vapor Permeability of Film (Unit: $g/m^2 \cdot 24$ h))>

Measurements were conducted in accordance with the method described in "JIS L-1099 testing methods for water vapor permeability of textiles" (2012) method A-1 (calcium chloride method) and method B-2 (alternative method 1 to the potassium acetate method). Thereafter, the values are converted for 24 hours. The results are shown in Table 12.

<Softening Temperature of Film (Unit: ° C.)>

Using a thermo mechanical analyzer (manufactured by Seiko Instruments, model: TMA/6600), the softening temperature of the 20 μm thick polyurethane elastomer film was measured in accordance with the method described in JIS K7196. The results are shown in Table 12.

1,3-bis(isocyanatomethyl)cyclohexane (TAKENATE 600, manufactured by Mitsui Chemicals, Inc.), 215.3 parts by mass of PTG1000 (polytetramethylene ether glycol having a number average molecular weight of 1000 manufactured by Hodogaya Chemical Co., LTD.) dehydrated in advance under reduced pressure, and 215.1 parts by mass of PTG2000SN (polytetramethylene ether glycol having a number average molecular weight of 2000, manufactured by Hodogaya Chemical Co., LTD.), and the mixture was stirred in a nitrogen atmosphere at 80° C. for 1 hour. Thereafter, 0.124 parts by mass of a solution in which tin octylate (catalyst, trade name: Stanoct, manufactured by API Corporation) was diluted in advance with DINA (manufactured by J-PLUS Co., Ltd.) to 4 mass % was added. Then, reaction was performed at 80° C. until the isocyanate group content reached 17.7 mass %, thereby producing an isocyanate group-terminated polyurethane prepolymer (a12)(simply called prepolymer (a12) in the following).

Preparation of Polyurethane Elastomer (A12)

A stainless steel container was charged with 835.7 parts by mass of the prepolymer (a12) having a preadjusted temperature of 80° C., 2.98 parts by mass of IRGANOX245 (heat-resistant stabilizer manufactured by BASF), 2.48 parts

TABLE 12

| | | | No. Ex. 71 |
|---|---|---|---|
| Polyisocyanate component | 1,4-BIC | | A |
| | Trans isomer ratio | mol % | 82 |
| | Compound represented by formula (1) content | ppm | 15 |
| Prepolymer formation | Prepolymer | | a11 |
| | Amount of isocyanate component | parts by mass | 228.7 |
| | Amount of polyol component | PEG2000 | parts by mass | 683.5 |
| | Catalyst | 4% U-600/DINA | parts by mass | 0.110 |
| | Prepolymer total amount | | parts by mass | 972.5 |
| Chain extension reaction | Prepolymer charged | | parts by mass | 900.0 |
| | R[NCO]/[OH] | | | 1.05 |
| | Chain extender | 1,4-BD | parts by mass | 71.72 |
| | Stabilizer | IRGANOX245 | parts by mass | 9.92 |
| | | Tinuvin234 | parts by mass | 2.95 |
| | | Adeka Stab LA-72 | parts by mass | 2.95 |
| Polyurethane elastomer | | | A11 |
| Hardness | | Shore A | 86 |
| Tensile physical property | Strength | MPa | 45 |
| | Elongation | % | 700 |
| Moisture permeability A-1 method | | g/m2 · 24 h | 6800 |
| Moisture permeability B-1 method | | g/m2 · 24 h | 130000 |
| TMA softening temperature | | ° C. | 170 |

<Synthesis and Evaluation of Polyurethane Elastomer (TPU) for Eyewear Frame>

Example 72

Synthesis of Prepolymer

A four-neck flask equipped with a stirrer, a thermometer, a reflux tube, and a nitrogen inlet tube was charged with 324.2 parts by mass of 1,4-BIC (A), 81.0 parts by mass of by mass of Tinuvin234 (ultraviolet absorber manufactured by BASF), and 1.49 parts by mass of Adeka StabLA-72 (HALS manufactured by ADEKA), and the mixture was stirred and mixed using a high-speed disper at 1000 rpm for about 2 minutes. Then, as a chain extender, 157.3 parts by mass of 1,4-BD having a preadjusted temperature of 80° C. was added, and the mixture was stirred and mixed using a high-speed disper at 1000 rpm for about 10 minutes.

Next, the reaction mixture liquid was poured into a SUS-made vat having a preadjusted temperature of 120° C., and reaction was performed at 1200° C. for 24 hours, thereby producing a polyurethane elastomer (A12).

Thereafter, the polyurethane elastomer (A12) was removed from the vat, and aged under constant temperature and humidity conditions of a room temperature of 23° C. and a relative humidity of 55% for 7 days.

The produced polyurethane elastomer (A12) was cut into dice with a bale cutter, and the diced resin was ground with a grinder. The ground pellets were dried under a nitrogen flow at 80° C. for a whole day and night. Strands were extruded using a monoaxial extruder (model: SZW40-28MG manufactured by Technovel Corporation) with a cylinder temperature in the range of 150 to 245° C. range, and they were cut, thereby producing polyurethane elastomer (A12) pellets. The produced pellets were further dried under nitrogen flow at 80° C. for a whole day and night.

Next, injection molding was performed using an injection molding machine (model: NEX-140, manufactured by NISSEI PLASTIC INDUSTRIAL CO., LTD.) under the following conditions setting the screw number of revolution to 80 rpm and the barrel temperature to 150 to 235° C.: a mold temperature of 20° C., an injection time of 10 seconds, an injection speed of 60 minis, and cooling time of 30 seconds. The produced sheet having a thickness of 2 mm was aged under constant temperature and humidity conditions of a room temperature of 23° C. and a relative humidity of 55% for 7 days, thereby producing an elastomer sheet.

Examples 73 to 75 and Comparative Examples 62 to 63

Prepolymers (a13 to 112) were synthesized in the same manner as in Example 72 based on the mixing formulation shown in Table 13, and polyurethane elastomers (A13 to L12) were produced.

Evaluation

<Hardness: Shore A>

Shore A hardness was measured in accordance with "JIS K-7311 Testing methods for thermoplastic polyurethane elastomers" (1995). The results are shown in Table 13 in numeral values.

<Tensile Physical Property>

A tensile test was performed using the produced sheet in conformity with the method described in "JIS K-7311 Testing methods for thermoplastic polyurethane elastomers" (1995). The test piece was punched out with a JIS-3 dumbbell, and the tensile strength at break (unit: MPa) and the elongation (unit: %) were measured using a tensile tester (manufactured by Toyoseiki kogyo Co., Ltd., trade name: all-automatic rubber tensile tester TYPE: AE-CT) under the following conditions: a bench mark distance of 20 mm and a tensile speed of 300 mm/min. The results are shown in Table 13.

<Izod Impact Test>

Measurements were performed at −30° C. based on the method described in conformity with "JIS K-7110 plastics—Determination of Izod impact strength" (1999), with notch and without notch (type A). The results are shown in Table 13.

<Temperature of Deflection Under Load>

Measurement was performed in conformity with method B in "JIS K7191-2 Plastics—Determination of temperature of deflection under load—Part 2: Plastics and ebonite plastic" (2007). The results are shown in Table 13.

<Parallel Light Transmittance (Unit: %), Haze>

The total luminous transmittance and haze (in conformity with JIS K7105 (light source: $D_{65}$)) of the 2 mm thick polyurethane elastomer sheet were measured using Haze Meter (manufactured by Nippon Denshoku Industries Co., Ltd., model: NDH 2000). The results are shown in Table 13.

<Solvent Resistance>

The injection sheet was punched out with a dumbbell into a size of 3×7 cm, was immersed in ethanol (manufactured by Wako Pure Chemical Industries, Ltd.), and allowed to stand at 23° C.×50% RH for 72 hours. The weight change rate before and after the immersion was shown in Table 13 as swelling rate.

<Heat-Resistant NOx Yellowing Test>

The polyurethane elastomer test piece was allowed to stand in a 90° C. hot air circulation oven for 1000 hours. Thereafter, the exposure test was conducted with a NOx concentration of 2,000 ppm for 2 hours in conformity with the test method in JIS L-0855 (2005). Thereafter, the test piece was further allowed to stand in a constant temperature and humidity container of 70° C. and 95% for 24 hours. The appearance after being allowed to stand was observed visually.

After further drying under reduced pressure at 60° C. for 24 hours, breaking elongation was measured in accordance with the above-described tensile test method. The elongation retention (unit: %) was calculated by dividing the breaking elongation after the test by the breaking elongation before the test, and multiplying the result by 100. The results are shown in Table 13.

<Appearance>

Appearance of the test piece after the test was visually observed. The evaluation criteria are shown below. The results are shown in Table 13.

Excellent; No Change

Good; slightly changed

Below average; changed a little

Bad; changed

The change means yellowing, becoming whitish, tack, and deformation.

TABLE 13

| | | | No. | | | | | |
|---|---|---|---|---|---|---|---|---|
| | | | Ex. 72 | Ex. 73 | Ex. 74 | Ex. 75 | Comp. Ex. 62 | Comp. Ex. 63 |
| Polyisocyanate component | 1,4-BIC | | A | A | A | A | K | L |
| | Trans isomer ratio | mol % | 82 | 82 | 82 | 82 | 82 | 82 |
| | Compound represented by formula (1) content | ppm | 15 | 15 | 15 | 15 | 0.07 | 340 |

TABLE 13-continued

| | | | | Ex. 72 | Ex. 73 | Ex. 74 | Ex. 75 | Comp. Ex. 62 | Comp. Ex. 63 |
|---|---|---|---|---|---|---|---|---|---|
| Prepolymer formation | Prepolymer | | | a12 | a13 | a14 | a15 | k12 | l12 |
| | Amount or isocyanate component | 1,4-BIC | Parts by mass | 324.2 | 156.8 | 423 | 300 | 324.2 | 324.2 |
| | | 1,3-BIC | Parts by mass | 81.0 | — | — | 75.0 | 81.0 | 81.0 |
| | | NBDI | Parts by mass | — | 166.6 | — | — | — | — |
| | Amount of polyol component | PTG1000 | Parts by mass | 215.3 | 213.0 | — | — | 215.3 | 215.3 |
| | | PTG2000SN | Parts by mass | 215.1 | 212.7 | — | — | 215.1 | 215.1 |
| | | PCL210 | Parts by mass | — | — | 215.3 | — | — | — |
| | | UH-200D | Parts by mass | — | — | 215.0 | 466.8 | — | — |
| | Catalyst | 4% Stanoct/DINA | Parts by mass | 0.124 | 0.124 | 0.124 | 0.124 | 0.124 | 0.124 |
| | Prepolymer total amount | | Parts by mass | 835.7 | 749.2 | 853.4 | 841.9 | 835.7 | 835.7 |
| Chain extension reaction | Prepolymer charged | | Parts by mass | 835.7 | 749.2 | 853.4 | 841.9 | 835.7 | 835.7 |
| | R[NCO]/[OH] | | | 1.01 | 1.01 | 1.01 | 1.01 | 1.01 | 1.01 |
| | Chain extender | 1,4-BD | Parts by mass | 157.3 | 243.9 | — | 151.0 | 157.3 | 157.3 |
| | | 1,3-PD | Parts by mass | — | — | 139.8 | — | — | — |
| | Stabilizer | IRGANOX 245 | Parts by mass | 2.98 | 2.98 | 2.98 | 2.98 | 2.98 | 2.98 |
| | | Tinuvin234 | Parts by mass | 2.48 | 2.48 | 2.48 | 2.48 | 2.48 | 2.48 |
| | | Adeka Stab LA-72 | Parts by mass | 1.49 | 1.49 | 1.49 | 1.49 | 1.49 | 1.49 |
| Polyurethane elastomer | | | | A12 | A13 | A14 | A15 | K12 | L12 |
| Hardness | | | Shore D | 60 | 60 | 60 | 60 | 59 | 58 |
| Tensile physical property | Strength | | MPa | 40 | 38 | 33.5 | 42 | 37 | 28 |
| | Elongation | | % | 550 | 520 | 510 | 570 | 450 | 440 |
| Izod impact test −30° C. | Notched | | kJ/m2 | N.B. | N.B. | N.B. | N.B. | 82 | 56 |
| | Not Notched | | kJ/m2 | N.B. | N.B. | N.B. | N.B. | N.B. | N.B. |
| Temperature of deflection under load | | | ° C. | 58 | 58 | 59 | 62 | 56 | 52 |
| Total luminous transmittance | | | % | 91 | 90 | 91 | 91 | 89 | 88 |
| | Haze | | | 1.2 | 1.3 | 1.8 | 1.2 | 2.1 | 4.2 |
| Solvent resistance | Degree of swelling 3 days after immersion (Weight change rate) | Ethanol | wt % | 6.5 | 5.4 | 3.4 | 3.1 | 6 | 15 |
| After heat-resistant NOx test | Appearance | | Visual observation | Excellent | Excellent | Excellent | Excellent | Good | Bad |
| | Elongation | | % | 530 | 500 | 470 | 560 | 400 | 380 |
| | Elongation Retention | | % | 96 | 96 | 92 | 98 | 89 | 86 |

The details of the abbreviations in Tables are shown below.

NBDI; norbornane diisocyanate trade name: Cosmonate NBDI (manufactured by Mitsui Chemicals, Inc.)

PTG1000; polytetramethylene ether glycol having number average molecular weight of 1000 (manufactured by Hodogaya Chemical Co., LTD.)

PTG2000SN; polytetramethylene ether glycol having a number average molecular weight of 2000 (manufactured by Hodogaya Chemical Co., LTD.)

PCL210; poly (caprolactone) diol having a number average molecular weight of 1000, trade name: PLACCEL 210 (manufactured by Daicel Corporation.)

UH-200D; polycarbonatediol having a number average molecular weight of 2000 trade name: ETERNACOLL UH-200D (manufactured by Ube Industries, Ltd.)

1,4-BD; 1,4-butanediol (manufactured by Wako Pure Chemical Industries, Ltd.)

1,3-PD; 1,3-propanediol (manufactured by Wako Pure Chemical Industries, Ltd.)

<Synthesis and Evaluation of Optical Polyurethane Resin for Eyewear Lens>

Example 76

Synthesis of Prepolymer

A four-neck flask equipped with a stirrer, a thermometer, a reflux tube, and a nitrogen inlet tube was charged with 450.5 parts by mass of 1,4-BIC (A), 114.8 parts by mass of UH-50 (polycarbonatediol having a number average molecular weight of 500 manufactured by Ube Industries, Ltd.) dehydrated in advance under reduced pressure, and 141.7 parts by mass of BPX-11 (polyol in which 2 mol of propylene oxide was added to bisphenol A, manufactured by ADEKA), and reaction was performed in a nitrogen atmosphere at 80° C. for 5 hours until the isocyanate group content reached 20.1 mass %, thereby producing an isocyanate group-terminated polyurethane prepolymer (a16)(simply called prepolymer (a16) in the following).

Preparation of Polyurethane (A16)

A stainless steel container was charged with 707.1 parts by mass of the prepolymer (a16) having a preadjusted temperature of 80° C., 4.97 parts by mass of IRGANOX245 (heat-resistant stabilizer manufactured by BASF), 0.99 parts by mass of Tinuvin234 (ultraviolet absorber manufactured by BASF), 0.99 parts by mass of Adeka StabLA-72 (HALS manufactured by ADEKA), and an anthraquinone blueing agent solution (blueing agent (trade name: Plast Blue 8514, manufactured by ARIMOTO CHEMICAL CO., LTD.) diluted with DINA to 0.1 mass %): the anthraquinone blueing agent solution was added so that the whole mixture liquid contained Plast Blue in an amount of 0.6 ppm. The mixture was stirred and mixed using a high-speed disper at 1000 rpm for about 2 minutes. Then, as a chain extender, a mixture solution of 103.5 parts by mass of 1,4-BD having a preadjusted temperature of 80° C. and 182.4 parts by mass of BPX-11 was added thereto, and the mixture was stirred and mixed using a high-speed disper at 1000 rum for about 10 minutes.

Next, the reaction mixture liquid was poured into a SUS-made vat having a preadjusted temperature of 120° C., and reaction was performed at 120° C. for 24 hours, thereby producing a polyurethane (A16).

Thereafter, the polyurethane (A16) was removed from the vat, and aged under constant temperature and humidity conditions of a room temperature of 23° C. and a relative humidity of 55% for 7 days.

The produced polyurethane (A16) was cut into dice with a bale cutter, and the diced resin was ground with a grinder. The ground pellets were dried under a nitrogen flow at 80° C. for a whole day and night. Strands were extruded using a monoaxial extruder (model: SZW40-28MG, manufactured by Technovel Corporation) with a cylinder temperature in the range of 150 to 245° C., and they were cut, thereby producing polyurethane (A16) pellets. The produced pellets were further dried under nitrogen flow at 80° C. for a whole day and night.

Next, injection molding was performed using an injection molding machine (model: NEX-140, manufactured by NISSEI PLASTIC INDUSTRIAL CO., LTD.) under the following conditions setting the screw number of revolution to 80 rpm and the barrel temperature to 150 to 235° C.: a mold temperature of 20° C., injection time of 10 seconds, an injection rate of 60 mm/s, and cooling time of 30 seconds. The produced sheet having a thickness of 2 mm was aged under constant temperature and humidity conditions of a room temperature of 23° C. and a relative humidity of 55% for 7 days, thereby producing a polyurethane sheet.

Examples 77 and 78 and Comparative Examples 64 and 65

Prepolymers (a17 to 113) were synthesized in the same manner as in Example 76 based on the mixing formulation shown in Table 14, and polyurethane (A14 to L13) were produced.

Evaluation

<Hardness: Shore A>

Shore A hardness was measured in accordance with "JIS K-7311 Testing methods for thermoplastic polyurethane elastomers" (1995). The results are shown in Table 14 in numeral values.

<Izod Impact Test>

Measurements were performed at −30° C. based on the method described in conformity with "JIS K-7110 plastics—Determination of Izod impact strength" (1999), with notch and without notch (type A). The results are shown in Table 14.

<Temperature of Deflection Under Load>

Measurement was performed in conformity with method B in "JIS K7191-2 Plastics—Determination of temperature of deflection under load—Part 2: Plastics and ebonite plastic" (2007). The results are shown in Table 14.

<Optical Properties>

The refraction (ne) and the Abbe's number (ve) were measured using a Pulfrich refractometer at 20° C. The results are shown in Table 14.

<Parallel Light Transmittance (Unit: %), Haze>

The total luminous transmittance and haze (in conformity with JIS K7105 (light source: $D_{65}$)) of the 2 mm thick polyurethane elastomer sheet were measured using Haze Meter (manufactured by Nippon Denshoku Industries Co., Ltd., model: NDH 2000). The results are shown in Table 14.

<Solvent Resistance>

The injection sheet was punched out with a dumbbell into a size of 3×7 cm, was immersed in ethanol (manufactured by Wako Pure Chemical Industries, Ltd.), and allowed to stand at 23° C.×50% RH for 72 hours. The weight change rate before and after the immersion is shown in Table 14 as swelling rate.

<Heat-Resistant NOx Yellowing Test>

The polyurethane elastomer test piece was allowed to stand in a 90° C. hot air circulation oven for 1000 hours. Thereafter, in conformity with the test method in JIS L-0855 (2005), the exposure test was conducted with a NOx concentration of 2,000 ppm for 2 hours. Thereafter, the test piece was further allowed to stand in a constant temperature and humidity container of 70° C. and 95% for 24 hours. The appearance after being allowed to stand was observed visually. The results are shown in Table 14.

<Appearance>

Appearance of the test piece after the test was visually observed. The evaluation criteria are shown below. The results are shown in Table 14.

Excellent; No Change
Good; slightly changed
Below average; changed a little
Bad; changed The change means yellowing, becoming whitish, tack, and deformation.

TABLE 14

| | | | Ex. 76 | Ex. 77 | Ex. 78 | Comp. Ex. 64 | Comp. Ex. 65 |
|---|---|---|---|---|---|---|---|
| Polyisocyanate component | 1,4-BIC | | A | A | A | K | L |
| | Trans isomer ratio | mol % | 82 | 82 | 82 | 82 | 82 |
| | Compound represented by formula (1) content | ppm | 15 | 15 | 15 | 0.07 | 340 |

TABLE 14-continued

| | | | | Ex. 76 | Ex. 77 | Ex. 78 | Comp. Ex. 64 | Comp. Ex. 65 |
|---|---|---|---|---|---|---|---|---|
| Prepolymer formation | Prepolymer | | | a16 | a17 | a18 | k13 | l13 |
| | Amount of isocyanate component | 1,4-BIC | Parts by mass | 450.5 | 316.5 | 509.5 | 316.5 | 316.5 |
| | | 1,3-BIC | Parts by mass | — | 316.5 | — | 316.5 | 316.5 |
| | | NBDI | Parts by mass | — | — | 137.8 | — | — |
| | Amount of polyol component | UH-50 | Parts by mass | 114.8 | 81.4 | 81.5 | 81.4 | 81.4 |
| | | BPX-11 | Parts by mass | 141.7 | — | — | — | — |
| | Catalyst | 4% Stanoct/DINA | Parts by mass | 0.124 | — | — | — | — |
| | Prepolymer total amount | | Parts by mass | 707.1 | 714.4 | 728.8 | 714.4 | 714.4 |
| Chain extension reaction | Prepolymer charged | | Parts by mass | 707.1 | 714.4 | 728.8 | 714.4 | 714.4 |
| | R[NCO]/[OH] | | | 1.01 | 1.01 | 1.01 | 1.01 | 1.01 |
| | Chain extender | 1,4-BD | Parts by mass | 103.5 | 278.7 | 264.3 | 278.7 | 278.7 |
| | | BPX-11 | Parts by mass | 182.4 | — | — | — | — |
| | Stabilizer | IRGANOX245 | Parts by mass | 4.97 | 4.97 | 4.97 | 4.97 | 4.97 |
| | | Tinuvin234 | Parts by mass | 0.99 | 0.99 | 0.99 | 0.99 | 0.99 |
| | | Adeka Stab LA-72 | Parts by mass | 0.99 | 0.99 | 0.99 | 0.99 | 0.99 |
| | Additive | Plast Blue 8514 | ppm | 0.60 | 0.60 | 0.60 | 0.60 | 0.60 |
| Polyurethane | | | | A16 | A17 | A18 | K13 | L13 |
| Hardness | | | Shore D | 80 | 80 | 80 | 78 | 77 |
| Izod impact test −30° C. | | Notched | kJ/m2 | 21 | 35 | 15 | 10 | 6 |
| | | Not Notched | kJ/m2 | 70 | 52 | 40 | 35 | 28 |
| Temperature of deflection under load | | | ° C. | 83 | 80 | 85 | 78 | 75 |
| | Refraction | | | 1.59 | 1.56 | 1.57 | 1.58 | 1.57 |
| | Abbe's number | | | 55 | 53 | 55 | 51 | 50 |
| Total luminous transmittance | | | % | 91 | 91 | 91 | 89 | 87 |
| | Haze | | | 0.9 | 1.0 | 1.0 | 1.8 | 2.8 |
| Solvent resistance | Degree of swelling 3 days after immersion (Weight change rate) | Ethanol | wt % | 3.5 | 2.9 | 2.7 | 5.3 | 7.1 |
| After heat-resistant NOx test | Appearance | | Visual observation | Excellent | Excellent | Excellent | Good | Bad |

The details of the abbreviations in Tables are shown below, 1,3-BIC; 1,3-bis(isocyanatomethyl)cyclohexane trade name: TAKENATE 600 (manufactured by Mitsui Chemicals, Inc.)

NBDI; norbornane diisocyanate trade name: Cosmonate NBDI (manufactured by Mitsui Chemicals, Inc.)

1,4-BD; 1,4-butanediol (manufactured by Wako Pure Chemical Industries, Ltd.)

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The 1,4-bis(isocyanatomethyl)cyclohexane, polyisocyanate composition, polyurethane resin, and molded article of the present invention can be used in a wide variety of applications including elastomers (polyurethane solution, aqueous polyurethane, heat melt molding (slush molding, rotational molding) urethane powder, thermoplastic urethane elastomers (TPU), thermosetting urethane elastomer (TSU), spray molding urethane, melt spinning or dry spinning method elastic fiber), paints (mainly solution-based, powder-based curing agent: adduct, allophanate, biuret, urethodione, polyisocyanurate, iminooxadiazinedione and a mixture thereof), industrial or hot melt adhesive, sealing material, polyurethane foam, gel, and furthermore, can be used in the eyewear material, eyewear frame, and lens of the present invention.

The invention claimed is:

1. A 1,4-bis(isocyanatomethyl)cyclohexane composition comprising 1,4-bis(isocyanatomethyl)cyclohexane and a compound represented by formula (1) below, wherein:
the 1,4-bis(isocyanatomethyl)cyclohexane contains a trans isomer of 1,4-bis(isocyanatomethyl)cyclohexane and a cis isomer of 1,4-bis(isocyanatomethyl)cyclohexane, and comprises 70 mol % or more and 95 mol % or less of the trans isomer relative to a total amount of the cis isomer and the trans isomer, and the 1,4-bis(isocyanatomethyl)cyclohexane composition contains 0.1 ppm or more and 300 ppm or less of the compound represented by formula (1) below:

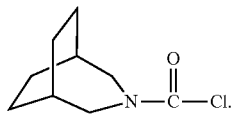

(1)

2. The 1,4-bis(isocyanatomethyl)cyclohexane composition according to claim 1, wherein the 1,4-bis(isocyanatomethyl)cyclohexane comprises 80 mol % or more and 93 mol % or less of the trans isomer relative to a total amount of the cis isomer and the trans isomer.

3. A polyisocyanate composition produced by modifying the 1,4-bis(isocyanatomethyl)cyclohexane composition according to claim 1,
and comprising at least one functional group of (a) to (e) below:
(a) an isocyanurate group obtained by trimerizing the 1,4-bis(isocyanatomethyl)cyclohexane,
(b) an allophanate group obtained by allowing the 1,4-bis(isocyanatomethyl)cyclohexane and a monoalcohol to react, and then further subjecting them to an allophanate-forming reaction,
(c) a biuret group obtained by allowing the 1,4-bis(isocyanatomethyl)cyclohexane to react with at least one selected from the group consisting of water, tertiary alcohol and secondary amine, and then further subjecting them to a biuretization reaction,
(d) a urethane group obtained by allowing the 1,4-bis(isocyanatomethyl)cyclohexane to react with a polyol component, and
(e) a urea group obtained by allowing the 1,4-bis(isocyanatomethyl)cyclohexane to react with water and/or a polyamine component.

4. A polyurethane resin produced by allowing a polyisocyanate component to react with an active hydrogen group-containing component, wherein the polyisocyanate component comprises the 1,4-bis(isocyanatomethyl)cyclohexane composition according to claim 1,
and/or
a polyisocyanate-modified composition produced by modifying the 1,4-bis(isocyanatomethyl)cyclohexane composition according to claim 1, and comprising at least one functional group of (a) to (e) below:
(a) an isocyanurate group obtained by trimerizing the 1,4-bis(isocyanatomethyl)cyclohexane,
(b) an allophanate group obtained by allowing the 1,4-bis(isocyanatomethyl)cyclohexane and a monoalcohol to react, and then further subjecting them to an allophanate-forming reaction,
(c) a biuret group obtained by allowing the 1,4-bis(isocyanatomethyl)cyclohexane to react with at least one selected from the group consisting of water, tertiary alcohol and secondary amine, and then further subjecting them to a biuretization reaction,
(d) a urethane group obtained by allowing the 1,4-bis(isocyanatomethyl)cyclohexane to react with a polyol component, and
(e) a urea group obtained by allowing the 1,4-bis(isocyanatomethyl)cyclohexane to react with water and/or a polyamine component.

5. A molded article produced from the polyurethane resin according to claim 4.

6. Fiber produced from the polyurethane resin according to claim 4.

7. A fabric obtained by using the fiber according claim 6 in at least a part thereof.

8. Nonwoven fabric obtained by using the polyurethane resin according to claim 4 in at least a part thereof.

9. Film produced from the polyurethane resin according to claim 4.

10. A sheet produced from the polyurethane resin according to claim 4.

11. Apparel obtained by using the fiber according claim 6 in at least a part thereof.

12. Apparel obtained by using the fabric according claim 7 in at least a part thereof.

13. Apparel obtained by using the nonwoven fabric according claim 8 in at least a part thereof.

14. Apparel obtained by using the film according claim 9 in at least a part thereof.

15. Apparel obtained by using the sheet according claim 10 in at least a part thereof.

16. Apparel according to claim 11, which is at least one selected from the group consisting of swimwear, compression wear, and underwear.

17. Apparel according to claim 12, which is at least one selected from the group consisting of swimwear, compression wear, and underwear.

18. Apparel according to claim 13, which is at least one selected from the group consisting of swimwear, compression wear, and underwear.

19. Apparel according to claim 14, which is at least one selected from the group consisting of swimwear, compression wear, and underwear.

20. Apparel according to claim 15, which is at least one selected from the group consisting of swimwear, compression wear, and underwear.

* * * * *